(12) United States Patent
Califorrniaa

(10) Patent No.: US 10,245,075 B2
(45) Date of Patent: Apr. 2, 2019

(54) NONDESTRUCTIVE MEANS OF ECTOPIC PREGNANCY MANAGEMENT

(71) Applicant: Eurica Califorrniaa, Haleiwa, HI (US)

(72) Inventor: Eurica Califorrniaa, Haleiwa, HI (US)

( * ) Notice: Subject to any disclaimer, the term of this patent is extended or adjusted under 35 U.S.C. 154(b) by 1018 days.

(21) Appl. No.: 14/214,897

(22) Filed: Mar. 15, 2014

(65) Prior Publication Data

US 2014/0221735 A1 Aug. 7, 2014

Related U.S. Application Data

(60) Provisional application No. 61/801,720, filed on Mar. 15, 2013.

(51) Int. Cl.
*A61B 17/435* (2006.01)
*A61G 11/00* (2006.01)
(Continued)

(52) U.S. Cl.
CPC ............ *A61B 17/435* (2013.01); *A61B 17/42* (2013.01); *A61G 11/00* (2013.01); *C12M 21/06* (2013.01);
(Continued)

(58) Field of Classification Search
CPC ................ A61G 11/00; A61G 2210/90; A61G 2203/20; A61G 2203/46; C12M 21/06; A61B 17/435; A61B 17/42
See application file for complete search history.

(56) References Cited

U.S. PATENT DOCUMENTS 4,574,000 A 3/1986 Hunter
4,734,097 A 3/1988 Tanabe et al.
(Continued)

OTHER PUBLICATIONS

Wallace, "Transplantations of ectopic pregnancy from fallopian tube to cavity of uterus," Surgery, Gynecology and Obstetrics, vol. 24, Jan.-Jun. 1917, pp. 578-579.*
(Continued)

*Primary Examiner* — Christine H Matthews
*Assistant Examiner* — Joshua Daryl D Lannu
(74) *Attorney, Agent, or Firm* — Boies, Schiller & Flexner LLP

(57) ABSTRACT

In a nondestructive means of ectopic pregnancy management, a baby is delivered with the gestational sac intact and then submerged in an incubator containing ventilating fluid; the baby is placed in an absorbable transfer capsule and transcervically transferred to the uterine cavity; the capsule dissolves after a period of time to leave the gestational sac abutted to the endometrium so the baby can reattach. To maintain the baby's life support, the means includes fluidic ventilators and ventilation catheters to perfuse the gestational sac with ventilating fluid during such times as delivery, incubation, transfer, and reimplantation. Advantageously, the transfer capsule protects the baby during transfer and serves as a convenient vehicle for placing devices such as the ventilation catheter in the uterus along with the baby. An exemplary transfer capsule is flexible like a soft contact lens; hydrates with a solution containing nutrients and factors to promote the biomechanical interactions of implantation; and, being based on a hyaluronan hydrogel, dissolves in the uterine cavity to provide the baby and mother with hyaluronan which is known to benefit implantation. Hard shell absorbable transfer capsules are also provided for when structural support is needed.

67 Claims, 17 Drawing Sheets

(51) Int. Cl.
*A61B 17/42* (2006.01)
*C12M 3/00* (2006.01)
(52) U.S. Cl.
CPC ...... *A61G 2203/20* (2013.01); *A61G 2203/46* (2013.01); *A61G 2210/90* (2013.01)

(56) References Cited

U.S. PATENT DOCUMENTS

| | | | | |
|---|---|---|---|---|
| 4,850,957 | A | * | 7/1989 | Summers ................. A61B 1/12 418/48 |
| 5,225,346 | A | * | 7/1993 | Matsumiya ............ C12M 23/14 383/102 |
| 5,981,826 | A | | 11/1999 | Ku et al. |
| 6,010,448 | A | | 1/2000 | Thompson |
| 6,387,413 | B1 | * | 5/2002 | Miyata .................... A61L 15/28 424/548 |
| 6,694,175 | B1 | | 2/2004 | Califorrniaa |
| 6,710,126 | B1 | | 3/2004 | Hirt et al. |
| 7,121,998 | B1 | * | 10/2006 | Califorrniaa ............ A01N 1/02 600/22 |
| 8,021,321 | B2 | | 9/2011 | Zawacki |
| 8,262,730 | B2 | | 9/2012 | Thomas et al. |
| 8,292,798 | B2 | | 10/2012 | Califorrniaa |
| 2008/0058758 | A1 | * | 3/2008 | Ranchod ............. A61M 25/007 604/508 |
| 2008/0077174 | A1 | * | 3/2008 | Mische ................. A61F 5/0089 606/198 |
| 2008/0097143 | A1 | * | 4/2008 | Califorrniaa ............ A01N 1/02 600/22 |
| 2010/0286471 | A1 | * | 11/2010 | Matsubara ............. A61G 11/00 600/22 |
| 2011/0156315 | A1 | * | 6/2011 | Khinast ..................... A61J 3/00 264/334 |

OTHER PUBLICATIONS

Califorrniaa, "Thermoregulation of Human Embryos and Hatchlings in a Prenidial Incubator Using Infrared Microthermography," Trends in Reproductive Biology, vol. 1, 2005, pp. 63-67.
Hu et al., "Regulation of Silk Material Structure by Temperature-Controlled Water Vapor Annealing," Biomacromolecules, vol. 12, No. 5, 2011, pp. 1686-1696.
Um et al., "Electro-Spinning and Electro-Blowing of Hyaluronic Acid," Biomacromolecules, vol. 5, No. 4, 2004, pp. 1428-1436.
Safi et al., "Study of Electrospinning of Sodium Alginate, Blended Solutions of Sodium Alginate/Poly(Vinyl Alcohol) and Sodium Alginate/Poly(Ethylene Oxide)," Journal of Applied Polymer Science, vol. 104, No. 5, 2007, pp. 3245-3255.
Lee et al., "Preparation of Atactic Poly(Vinyl Alcohol)/Sodium Alginate Blend Nanowebs by Electrospinning," Journal of Applied Polymer Science, vol. 106, No. 2, 2007, pp. 1337-1342.
Hay et al., "Microbial Alginate Production, Modification and its Applications," Microbial Biotechnology, vol. 6, No. 6, 2013, pp. 637-650.
Sabra et al., "Bacterial Alginate: Physiology, Product Quality and Process Aspects," Applied Microbial Biotechnology, vol. 56, Nos. 3-4, 2001, pp. 315-325.
Misic et al., "Novel Starch-Based PVA Thermoplastic Capsules for Hydrophilic Lipid-Based Formulations," Journal of Pharmaceutical Science, vol. 101, No. 12, 2012, pp. 4516-4528.
Rindlav-Westling et al., "Crystallinity and Morphology in Films of Starch, Amylose and Amylopectin Blends," Biomacromolecules, vol. 3, No. 1, 2002, pp. 84-91.
Zhai et al., "Syntheses of PVA/Starch Grafted Hydrogels by Irradiation," Carbohydrate Polymers, vol. 50, No. 2, 2002, pp. 295-303.
Quraishi et al., "Transport of Sugars Across Human Placental Membranes Measured by Light Scattering," Placenta, vol. 20, Nos. 2-3, 1999, pp. 167-174.
Tuuli et al., "Review: Oxygen and Trophoblast Biology—A Source of Controversy," Placenta, vol. 32, Suppl. 2, 2011, pp. S109-S118.
Challier et al., "In Vitro Perfusion of Human Placenta. V. Oxygen Consumption," American Journal of Obstetrics and Gynecology, vol. 126, No. 2, 1976, pp. 261-265.
Quilligan et al., "Oxygen Tension in the Intervillous Space," American Journal of Obstetrics and Gynecology, vol. 88, No. 5, 1964, pp. 572-577.
Hwang et al., "Evaluation of the Paratrend Multi-Analyte Sensor for Potential Utilization in Long-Duration Automated Cell Culture Monitoring," Biomedical Microdevices, vol. 6, No. 3, 2004, pp. 241-249.
Soydemir et al., "Adapting In Vitro Dual Perfusion of the Human Placenta to Soluble Oxygen Tensions Associated with Normal and Pre-Eclamptic Pregnancy," Laboratory Investigation, vol. 91, No. 2, 2011, pp. 181-189.
Schoberer et al., "Fifty Years of Work on the Artificial Placenta: Milestones in the History of Extracorporeal Support of the Premature Newborn," Artificial Organs, vol. 36, No. 6, 2012, pp. 512-516.
Larqué et al., "Placental Transfer of Fatty Acids and Fetal Implications," The American Journal of Clinical Nutrition, vol. 94, Suppl., 2011, pp. 1908S-1913S.
Magnusson-Olsson et al., "Effect of Maternal Triglycerides and Free Fatty Acids on Placental LPL in Cultured Primary Trophoblast Cells and in a Case of Maternal LPL Deficiency," American Journal of Physiology—Endocrinology, and Metabolism, vol. 293, No. 1, 2007, pp. E24-E30.
Lager, "Cytokines and Lipids in Pregnancy: Effects on Developmental Programming and Placental Nutrient Transport," Ph.D. Thesis, University of Gothenburg, Sweden, 2010.
Sadler, Langman's Essential Medical Embryology, Lippinott, Williams & Wilkins (Philadelphia, PA): 2005, pp. 138-139.
Catholics United for Faith, "A Catholic Approach to Tubal Pregnancies," Lay Witness Magazine, Jan.-Feb. 2004.
Cone, Jr., History of the Care and Feeding of the Premature Infant, Boston: Little, Brown, 1985, pp. 21-22.
Tauber et al., "Polymer Electrospinning as a Novel Technique to Create a PVA Contact Lens," American Society of Cataract and Refractive Surgery/American Society of Ophthalmic Administrators, ASCRS/ASOA 2008 (Apr. 4-9), Abstract #P-179.
Merriam-Webster's Collegiate Dictionary, 11th ed., Springfield, MA: Merriam-Webster, 2008; pabulum (def. 1), p. 888.
Dorland's Illustrated Medical Dictionary, 32nd ed., Philadelphia, PA: Saunders, 2011; age, p. 37; exudate, p. 665; gestation period, see under period, pp. 1415-1416; hemotroph, p. 843; histotroph, p. 864; plasma (def. 1), p. 1456; pregnancy (def. 2), p. 1509-1510; teratogen, p. 1883; transudate, p. 1956.
Barrett, "Boston IVF Web Site Inquiry," Personal Communication, Jul. 7, 2004.
Clark, "Embryo transfer in vivo," Journal of the National Medical Association, vol. 74, No. 8, 1982, pp. 721-724.
Gaither et al., "Follow-up of live extra-uterine pregnancies," Journal of the National Medical Association, vol. 66, No. 1, 1974, pp. 69-70 and 52.
Shettles, "Tubal embryo successfully transferred in utero," American Journal of Obstetrics and Gynecology, vol. 163, No. 6, Part 1, 1990, 2026-2027.
Moll et al., "The flow resistance of the spiral artery and the related intervillous space in the rhesus monkey placenta," Pflügers Archiv—European Journal of Physiology, vol. 377, No. 3, 1978, pp. 225-228.
Merriam-Webster, Dictionary (online), deliver, https://www.merriam-webster.com/dictionary/deliver (accessed Apr. 10, 2017).
GE Healthcare, "This New Ultrasound Scanner Gives Doctors an Improved Look into the World of an Unborn Child," The Pulse on Health, Science & Tech, Sep. 15, 2014, http://newsroom.gehealthcare.com/ultrasound-scanner-doctors-improved-world-unborn-child/ (accessed Apr. 8, 2017).
Fylstra et al., "Ectopic pregnancy not within the (distal) fallopian tube: etiology, diagnosis, and treatment," American Journal of Obstetrics and Gynecology, Apr., vol. 206, No. 4, 2012, pp. 289-299.
Scutiero et al., "Primary ovarian pregnancy and its management," Journal of the Society of Laparoendoscopic Surgeons, Jul.-Sep., vol. 16, No. 3, 2012, pp. 492-494.

(56) References Cited

OTHER PUBLICATIONS

Fadhlaoui et al., "Ruptured intramural pregnancy with myometrial invasion treated conservatively," Case Reports in Obstetrics and Gynecology, vol. 2011, Article ID 965910, 2011, pp. 1-3.
Wikipedia (Lotus birth), https://en.wikipedia.org/wiki/Lotus_birth (accessed Aug. 16, 2018).
Harness, "10 births that set world records," TopTenz, Nov. 28, 2017, https://www.toptenz.net/10-births-set-world-records.php (accessed Aug. 16, 2018).
Tsunoda et al., "Effect of various procedures on the viability of mouse embryos containing half the normal number of blastomeres," Journal of Reproduction and Fertility, vol. 69, No. 1, Sep. 1983, pp. 315-322.
Cosby et al., "Microencapsulation of single, multiple, and zona pellucida-free mouse preimplantation embryos in sodium alginate and their development in vitro," Journal of Reproduction and Fertility, vol. 90, No. 1, Sep. 1990, pp. 19-24.
Adaniya et al., "First pregnancies and livebirths from transfer of sodium alginate-encapsulated embryos in a rodent model," Fertility and Sterility, vol. 59, No. 3, Mar. 1993, pp. 652-656.
Cowan et al., "The egg-embryo chamber for intraabdominal culture," Fertility and Sterility, vol. 38, No. 5, Nov. 1982, pp. 616-620.
Wartield et al., "Transfer of bovine demi-embryos with and without the zona pellucida," Journal of Animal Science, vol. 65, No. 3, Sep. 1987, pp. 756-761.
Adaniya et al., "Encapsulation of mammalian embryos," In: Cell Encapsulation Technology and Therapeutics, Kühtreiber et al., eds., Birkhäuser Boston, 1999, pp. 300-306.
Willadsen, "A method for culture of micromanipulated sheep embryos and its use to produce monozygotic twins," Nature, vol. 277, No. 5694, Jan. 1979, pp. 298-300.

\* cited by examiner

VF - Ventilating fluid
B - Baby

AA - Alluvia anterioris
AP - Alluvia posterioris
B - Baby

FB Formal Body

Adapted from: Sadler, Langman's Essential Medical Embryology, Lippinott, Williams & Wilkins (Philadelphia, PA): 2005; Fig. 11.5, pp. 138-139.

Risk of Birth Defects Being Induced
(Susceptibility to Teratogens)

Sequential Stages of Fluidic Ventilation

Adapted from: Tuuli et al., Placenta, Vol. 32, Suppl. 2, 2011, pp. S109-S118; Fig. 1, p. S110.

Intervillous Oxygen Tension Measurements During Pregnancy

Adapted from: Soydemir et al., Laboratory Investigation, Vol. 91, No. 2, 2011, pp. 181-189; Fig. 1(b), p. 183.

(Art of Soydemir et al.)

NONDESTRUCTIVE MEANS OF ECTOPIC PREGNANCY MANAGEMENT

BACKGROUND OF THE INVENTION

1. Field of Invention

The invention relates to incubators for babies (current US class/subclass 600/22), more specifically to incubators for babies before they are ready to breathe air, and especially to incubators for babies before reimplantation. More generally, the invention relates to a nondestructive means of ectopic pregnancy management. The overall scope of the invention relates to methods, apparatus, and compositions of matter for transferring a baby from an ectopic site to a uterine cavity for continued pregnancy, without harming the mother or baby.

2. Incorporated Teachings

The following of my teachings are incorporated herein by way of reference: U.S. application Ser. No. 13/649,848, filed Oct. 11, 2012, for a method of thermoregulation within an incubator for babies before implantation, now U.S. Pat. No. 9,056,039; U.S. application Ser. No. 11/549,972, filed Oct. 16, 2006, now U.S. Pat. No. 8,292,798, for an incubator for babies before implantation; U.S. application Ser. No. 10/908,861, filed May 30, 2005, now U.S. Pat. No. 7,121,998, for a vented microcradle for prenidial incubator; U.S. application Ser. No. 10/079,955, filed Feb. 19, 2002, now U.S. Pat. No. 6,694,175, for a method of monitoring the body temperature of human embryos and hatchlings; and, Califorrniaa, "Thermoregulation of Human Embryos and Hatchlings in a Prenidial Incubator Using Infrared Microthermography," Trends in Reproductive Biology, Vol. 1, 2005, pp. 63-67.

3. Prior Art

The word ectopic is derived from Greek meaning "out of place" (Gr. ek- out of +topos place). An ectopic pregnancy is one in which the baby has implanted "out of place." In other words, rather than implanting in the uterine cavity, where the baby belongs, the baby has implanted somewhere else, for example, in a fallopian tube. Except in relatively rare cases, the baby cannot survive in the ectopic site. In most cases, only the baby will die; but in other cases the mother will also die without intervention.

In this disclosure, pregnancy transfer means a nondestructive transfer of a baby from one pregnancy site to another; ectopic pregnancy transfer means more specifically a nondestructive transfer of the baby from an ectopic pregnancy site to another pregnancy site, which is preferably the uterine cavity.

In this disclosure, any transfer of an infant out of the mother's body is called delivery, regardless of prematurity. Transfer of the infant to the mother's uterus is called implantation, as is the process of attachment; it is also called reimplantation to indicate a previous implantation or a procedure involving what would normally be post-implantation development.

The prior art largely views ectopic pregnancy transfer as infeasible.

According to Catholics United for Faith: "There is a case that took place in 1915 in which a doctor, in the process of removing a tumor from a uterus, discovered an early tubal pregnancy. The operation on the tumor had left an incision in the uterus. The doctor transferred the embryo to the uterus through the incision. The embryo implanted, and the mother eventually gave birth to a healthy baby. The same hospital allowed further attempts at embryo transferal. Only a very small percentage were successfully implanted and born. Of those, the majority did not live very long. Most died between the ages of six and 12 years. With such low odds of the birth of a healthy baby, it is rare nowadays for medical professionals to consider embryo transferal. Recently a doctor at a Catholic fertility institute attempted three embryo transferals with none surviving to birth." See Catholics United for Faith, "A Catholic Approach to Tubal Pregnancies," Lay Witness Magazine, January-February, 2004.

Thus, although many have dreamed of an ability to save a baby in an ectopic pregnancy by reimplanting the baby in the uterus, doctors largely regard this approach as infeasible. Instead, in view of the limitations of the prior art, the accepted approach to ectopic pregnancy management has been one of destructive removal, either surgically or by drugs.

4. Statement of the Necessity

The prior art teaches a destructive management of ectopic pregnancy, bringing tragedy to infants and their families.

But it is worth noting that an abdominal ectopic pregnancy sometimes results in a healthy term delivery by cesarean section. Of particular interest is the most common case called a secondary abdominal pregnancy, which occurs when a baby breaches the fallopian tube in a case of tubal pregnancy and then reimplants inside the abdominal cavity. Given this natural example of successful reimplantation, it is reasonable to believe new technologies will make reimplantation a viable option of pregnancy management.

What is needed is a nondestructive means of ectopic pregnancy management.

BRIEF SUMMARY OF THE INVENTION

The invention satisfies the above-stated needs.

It is an object of the invention to provide a nondestructive means of ectopic pregnancy management, including methods, apparatus, and compositions of matter, whereby a baby's gestational needs are satisfied without harm to the mother.

The inventive methods include: delivering a baby from an ectopic pregnancy site;
  incubating the baby in a fluidic incubator; enclosing the baby in an absorbable transfer capsule; and, implanting the baby in a uterine cavity.

The inventive apparatus includes: fluidic ventilators; fluidic incubators; ventilation catheters and other fluidic accessory devices; absorbable transfer capsules; and, chorionic spacers.

Absorbable devices according to the invention, in particular absorbable transfer capsules, comprise at least one absorbable material. Preferred compositions of matter for such materials contain glycoprotein or hyaluronan.

The invention teaches the critical importance of fluidic ventilation, especially of an anterior aspect of the gestational sac. Related teachings include ensuring abutment of the gestational sac to the endometrium, especially the anterior aspect of the gestational sac, and maintaining the fluidic patency of the intervillous space.

The invention teaches transcervical reimplantation over uterine incision, and teaches preference for orienting the baby in the uterus in a posterior fundal position.

Additional methods, apparatus, and compositions of matter are taught in the detailed description to follow.

Key limitations of the prior art overcome by the invention are that the baby had to be transferred to the uterine cavity shortly after delivery (due to lack of the inventive incubator); without external protection (due to lack of the inventive transfer capsule); without supplementary life support in the uterus to assist reimplantation (due to lack of the inventive ventilator and its associated ventilation catheter); and, without ensuring the fluidic patency of the intervillous space against compression by the uterus (due to lack of the inventive chorionic spacer).

In contrast to the present invention, it also appears the prior art neglected to ensure abutment of the anterior aspect of the gestational sac to the endometrium in a preferred orientation within the uterine cavity, such as the posterior fundal position.

According to the invention, the baby is delivered from an ectopic pregnancy site with the gestational sac intact and is then submerged within a fluidic incubator, which contains a liquid media for the baby's life support called ventilating fluid.

The incubator operates to satisfy the needs of the baby who is not yet ready to breathe air, including the most critical needs of thermoregulation and fluidic ventilation. Advantageously, this gives the operator time to prepare the mother for reimplantation, to check on the baby's health status, and to repair any damage to the gestational sac.

The baby is then placed inside an absorbable transfer capsule and transferred to the uterine cavity. Compared to bare transfer, encapsulated transfer is advantageous because it protects the baby from insult; it shelters the baby from a passing maternal inflammatory response provoked by disturbance of the endometrium; and, it serves as a convenient vehicle for placing life support devices in the uterus along with the baby to provide supplementary assistance.

FIG. 13 is most descriptive of the invention, showing an embodiment of a transcervical reimplantation according to the invention. In this example, a baby B is transferred to the uterine cavity UC with the benefit of an absorbable transfer capsule ATC, ventilation catheter CTH, and chorionic spacer CS. The catheter CTH is connected to an external fluidic ventilator 21 to maintain a circulation of a ventilating fluid over the gestational sac. The ventilating fluid is a liquid media to provide the baby with life support by perfusing the outside of the gestational sac, which presents an exchange surface for the baby to receive vital substances and remove wastes in a process called fluidic ventilation. The outward facing surface of the gestational sac is the chorionic plate; on it grow numerous chorionic villi in the form of trunks with numerous branches to immensely increase the surface area of the exchange. The void between the villi is known as the intervillous space. To maintain a fluidic patency of the intervillous space against compression forces, the chorionic spacer CS maintains a predetermined distance between the chorionic plate and the wall of the capsule ATC and later the wall of the endometrium ENDO once the capsule dissolves.

Referring to FIG. 13, according to the exemplary embodiment, in a first step K4 the cervix CER is dilated and the baby B is transcervically transferred to the uterine cavity UC while protected inside the capsule ATC. In a second step K5, the cervix CER is closed. In a third step K6, the baby B continues to be fluidically ventilated in the uterus by means of the catheter CTH while still inside the capsule. In a fourth step K7, the absorbable transfer capsule ATC dissolves to leave the baby's bare gestational sac abutted to the endometrium ENDO. In a fifth step K8, the baby B reattaches to the uterus U while receiving supplementary life support from the ventilator 21 via the catheter CTH, and the chorionic spacer CS maintains the fluidic patency of the intervillous space despite compression from the uterus.

According to the invention, absorbable transfer capsules are typically scheduled to degrade within minutes, hours, days, or weeks of being introduced into the uterine cavity to leave the baby's bare gestational sac abutted to the endometrial lining of the uterine cavity. FIGS. 9 and 26 show examples of respective hard and soft shell varieties of the inventive absorbable transfer capsule ATC. Referring to FIG. 9, an example of the hard shell variety is like a plastic Easter egg with joinable halves in which to enclose the baby; this example provides structural support when needed. Referring to FIG. 26, an example of the soft shell variety is like a squeeze-type coin purse of the rubbery variety; it has flexible walls 62 to enclose the baby like a coin purse; this variety is typically formed of a hydrous polymer. An exemplary embodiment of an absorbable transfer capsule of the soft shell variety is flexible like a soft contact lens; hydrates with a solution containing nutrients and factors to promote the biomechanical interactions of implantation; and, being based on a hyaluronan hydrogel, dissolves in the uterine cavity to provide the baby and mother with hyaluronan which is known to benefit implantation.

To sum up, the two key life support functions performed by life support systems and methods according to the invention are fluidic ventilation and its interrelated function of thermoregulation. The invention further provides protection from insult and disease, as well as a convenient vehicle for transferring the baby to the mother's body.

Babies do not breathe air during gestation. Instead, their needs of respiration, feeding, hydration, warmth, and waste removal are accomplished by means of fluidic ventilation. Referring to FIG. 1A, according to the process of fluidic ventilation a baby B is fluidically ventilated by perfusing the gestational sac with a ventilating fluid VF. The ventilating fluid is a liquid media containing vital substances for the baby's growth and respiration and it also provides a medium for the baby's waste removal. By virtue of its ambient temperature and flow rate in contact with the gestational sac, the ventilating fluid also serves a thermoregulatory role by maintaining the baby's temperature and by dissipating the heat produced by the baby's body.

Given the paramount importance of fluidic ventilation for babies before they are ready to breathe air, it is easy to see why fluidic ventilators are at the heart of the inventive life support systems; for by providing fluidic ventilation, the inventive ventilators operate to maintain the baby's life support, whether in the incubator, transfer capsule, or mother.

Referring to FIG. 1B, an anterior aspect of the gestational sac, here called the alluvia anterioris AA, is that aspect in physiological communication with the umbilical cord, and a remaining posterior aspect is here called the alluvia posterioris AP. Since a greater load of life support is handled by the anterior via the umbilical cord, the operator is taught the superior importance of ventilating the anterior. Similarly, the operator is taught to ensure abutment of the anterior to the endometrium, including in a preferred posterior fundal position.

FIG. 28 is a graph of the sequential stages of fluidic ventilation provided for the baby by the mother over the natural course of gestation, here called maternal ventilation. By analogy to the sequential stages of maternal ventilation, the invention teaches the operator to employ a ventilating fluid having a development-specific composition and oxygen tension to ventilate the baby by means of a fluidic ventilator, so as to emulate or supplement the maternal provision.

To perform a nondestructive pregnancy transfer the operator is taught that the baby needs thermoregulation and fluidic ventilation, as well as protection from insult and disease. The invention satisfies these needs, and further provides a convenient transfer vehicle in the form of the absorbable transfer capsule, to provide the nondestructive means of ectopic pregnancy transfer.

In lexical usage, to implant means either to implant or reimplant, but to reimplant generally emphasizes a previous implantation. In a procedural context, implanting means the act of transfer to the mother as well as the process of attachment to the maternal body.

According to the invention, pregnancy transfer includes the overall process of performing an infant's delivery, incubation, and (re)implantation. A baby scheduled for implantation is said to be implantable. But even when transfer to the mother is not indicated, the invention provides incubators for both the ongoing and hospice care of babies before they are ready to breathe air.

These and other objects and advantages of the present invention will be appreciated in view of the detailed description to follow.

BRIEF SUMMARY OF THE SEVERAL VIEWS OF THE DRAWING

FIG. 1A shows the baby's gestational sac being fluidically ventilated with a ventilating fluid VF to supply vital substances and remove wastes for the baby's life support.

FIG. 1B indicates an anterior aspect of the gestational sac, here called the alluvia anterioris AA, versus a posterior aspect of the gestational sac, here called the alluvia posterioris AP. The anterior is distinguished as that aspect in physiological communication with the umbilical cord; the remainder is the posterior.

FIG. 2A shows the formal aspect of the baby's whole body; this is the "baby" part of the conceptus, also called the formal body FB.

FIG. 2B shows the peripheral aspect of the baby's whole body; this is literally the "spacesuit" part of the conceptus, here called a fluidic spacesuit, and more formally speaking an alluvial spacesuit S, also called the peripheral body.

Though both aspects are part of the baby's body as a whole, calling the formal body the "baby" part emphasizes that this aspect of the conceptus persists as the baby; in contrast, the peripheral aspect, though part of the baby during gestation, is ultimately discarded at birth once the umbilical cord is cut.

Figure 2A:
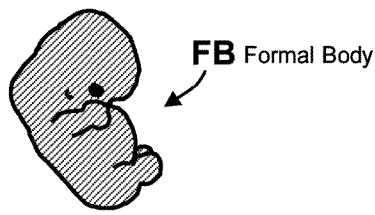
FIGS. 2A-2B are side cross-sectional views showing what are here called the formal and peripheral aspects, respectively, of the baby of FIG. 1A. From fertilization until the umbilical cord is cut at birth, the baby's whole body is emphasized by use of the term conceptus.
Figure 2B:
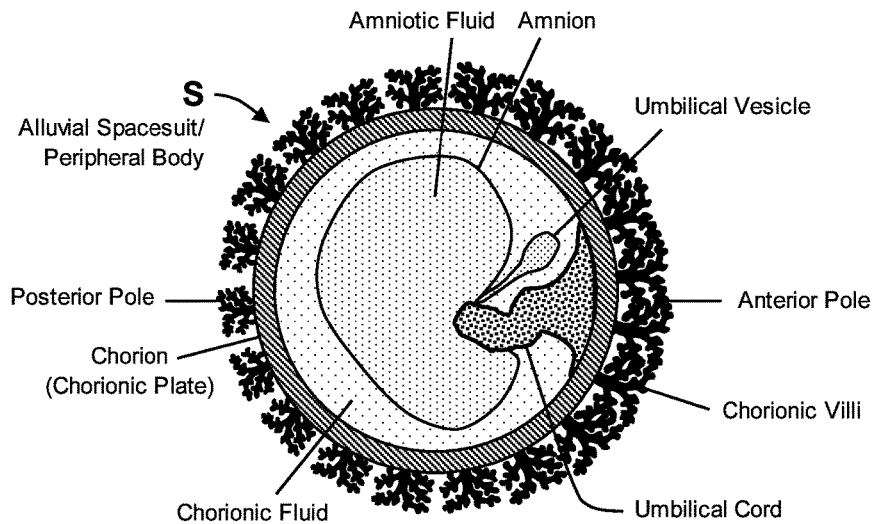

At the stage depicted in FIG. 2B, the gestational sac is formed by the chorionic plate and chorionic villi. Prior to implantation it was formed by the chorion alone since as yet no villi had grown on it. Later it will also include the amnion after it fuses with the chorion. The intervillous space, located between the chorionic plate and the wall of the uterus, is the space in which maternal fluid circulates between the villi to provide the baby with life support by supplying vital substances and removing wastes in the process called fluidic ventilation.

Figure 3A:
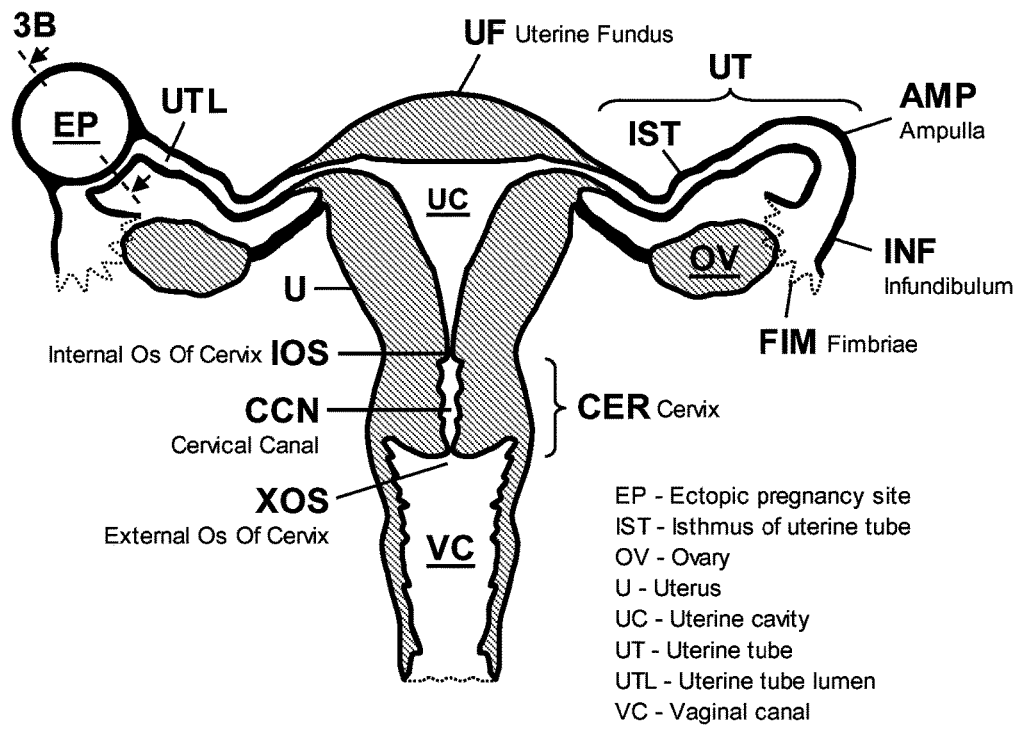
Figure 3B:
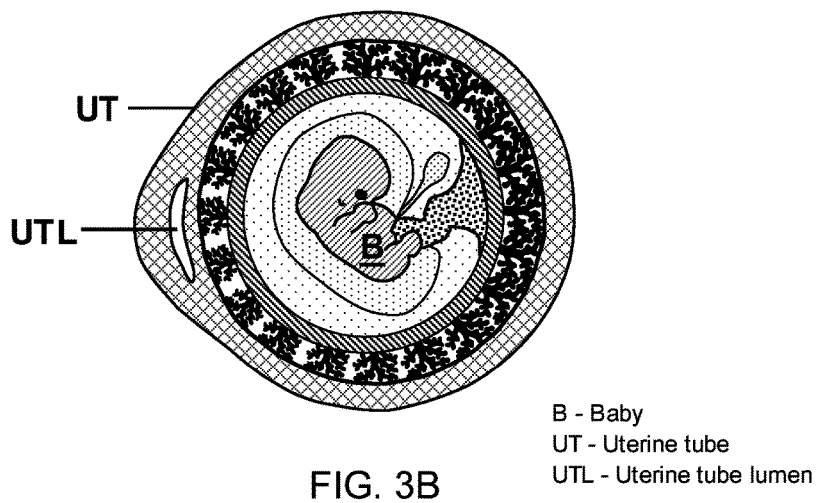

FIGS. 3A-3B show a typical situation of ectopic pregnancy, known specifically as a tubal pregnancy, and more specifically as an ampullar pregnancy.

FIG. 3A is a frontal cross-sectional view of a mother's reproductive tract indicating an ectopic pregnancy EP situated in one of her two uterine tubes UT (fallopian tubes).

FIG. 3B is a cross-sectional view of the ectopic pregnancy EP taken about a line 3B in FIG. 3A, which shows a baby B implanted and growing inside the uterine tube UT.

Figure 4:
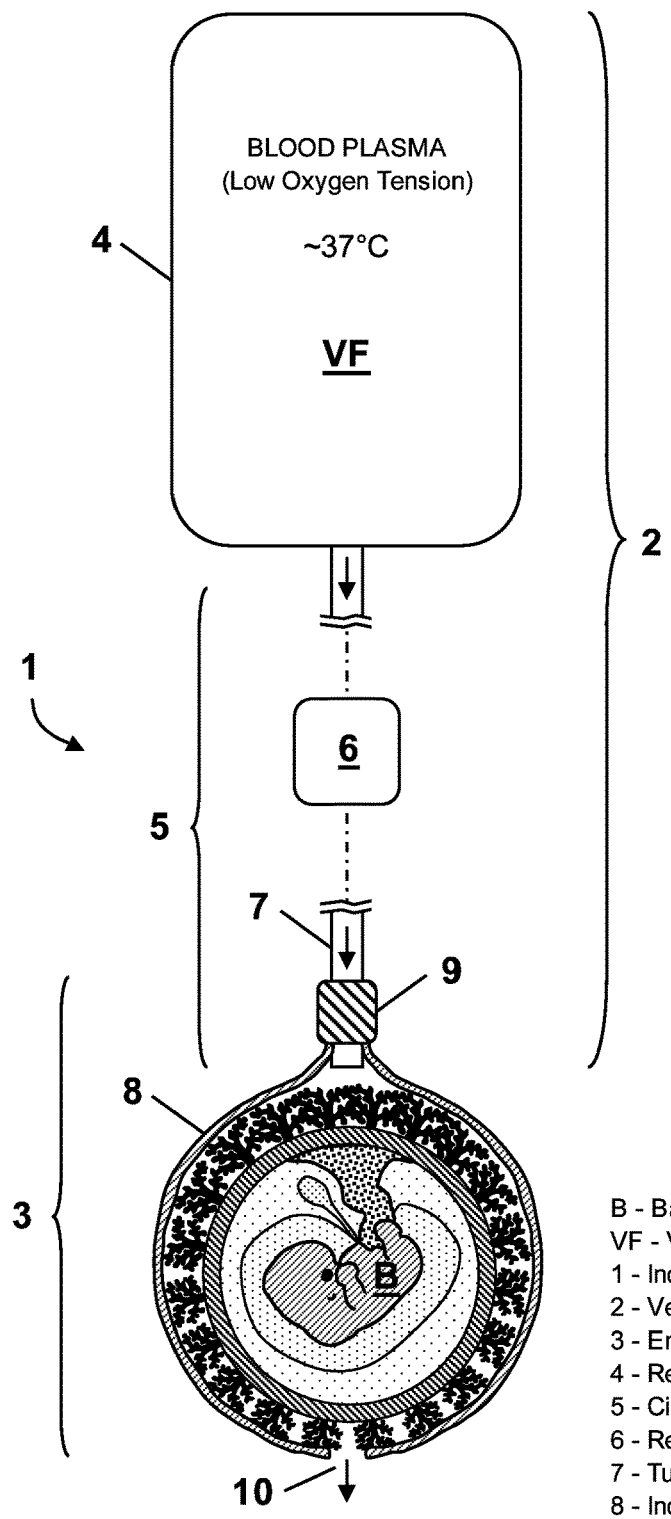

FIG. 4 is a side cross-sectional view of an exemplary embodiment of a fluidic incubator 1 according to the invention, more formally called an alluvial incubator.

Figure 5:
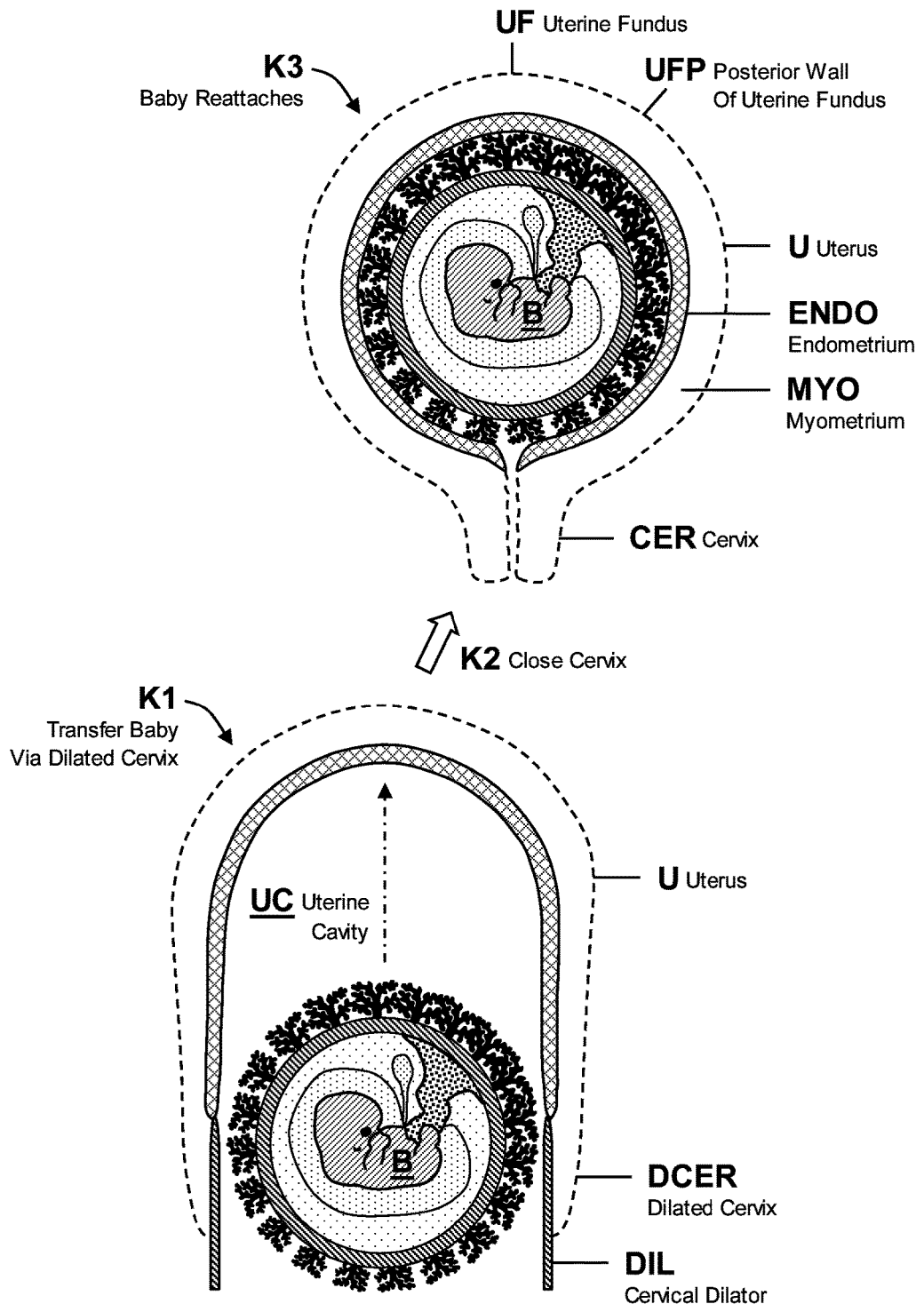

FIG. 5 is a median cross-sectional view of a transcervical reimplantation according to the invention. This example depicts what is here called bare transfer, in contrast to encapsulated transfer, since the baby is bare rather than encapsulated.

Figure 6:
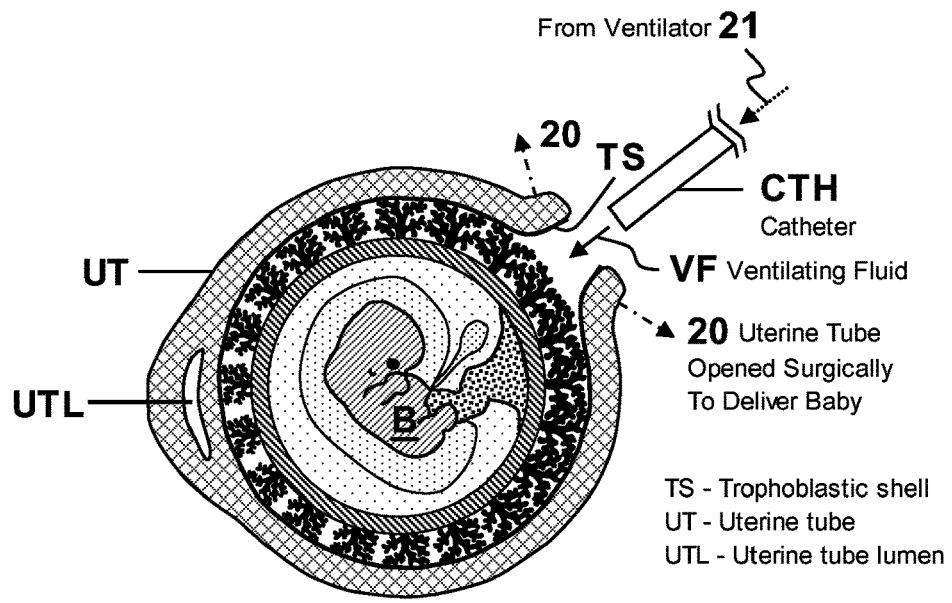

FIG. 6 shows the baby B of FIG. 3B being delivered from the uterine tube UT and receiving in situ ventilation according to the invention.

Figure 7:
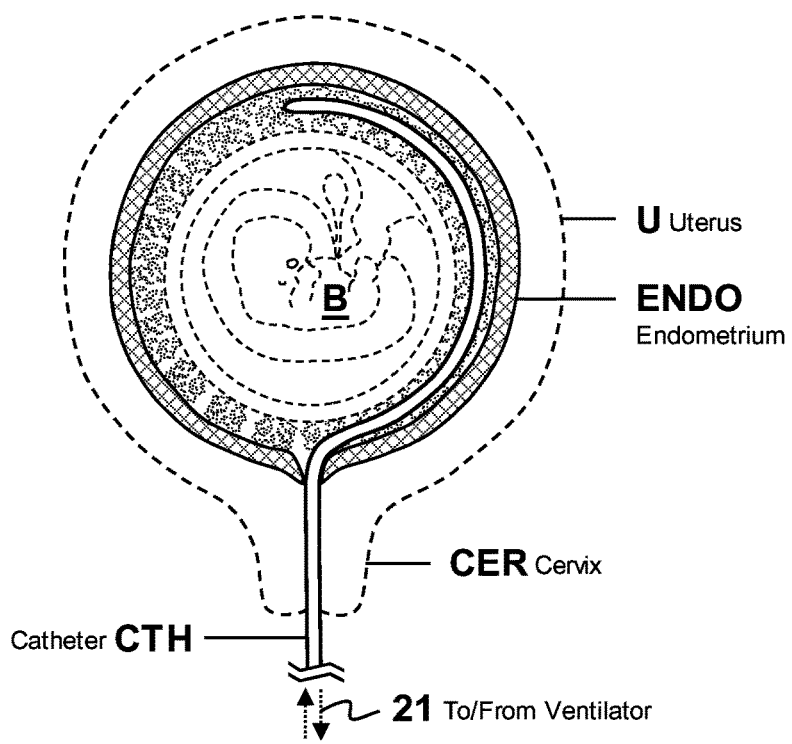

FIG. 7 is a median cross-sectional view of a baby B in the uterus U receiving in utero ventilation according to the invention.

Figure 8:
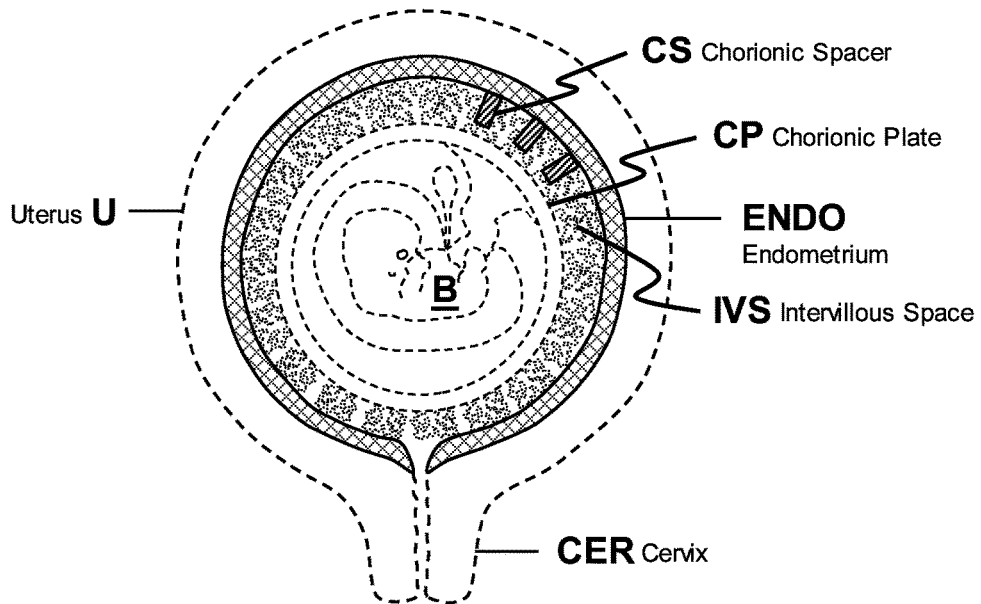

FIG. 8 is a median cross-sectional view of a baby B in the uterus U having the benefit of a chorionic spacer CS according to the invention.

Figure 9:
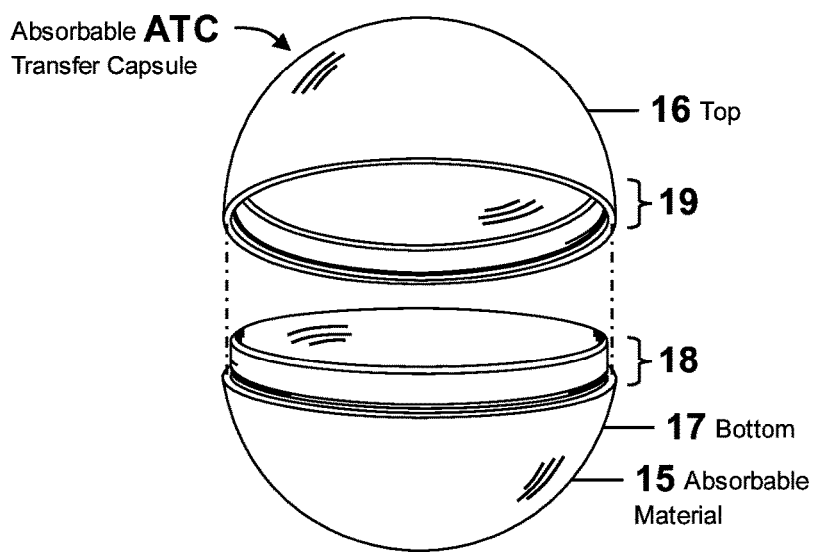

FIG. 9 is a side perspective exploded view of an exemplary embodiment of an absorbable transfer capsule ATC according to the invention. This example depicts a hard shell type capsule structure for enclosing a baby, likened to closing the halves of a plastic Easter egg.

Figure 10:
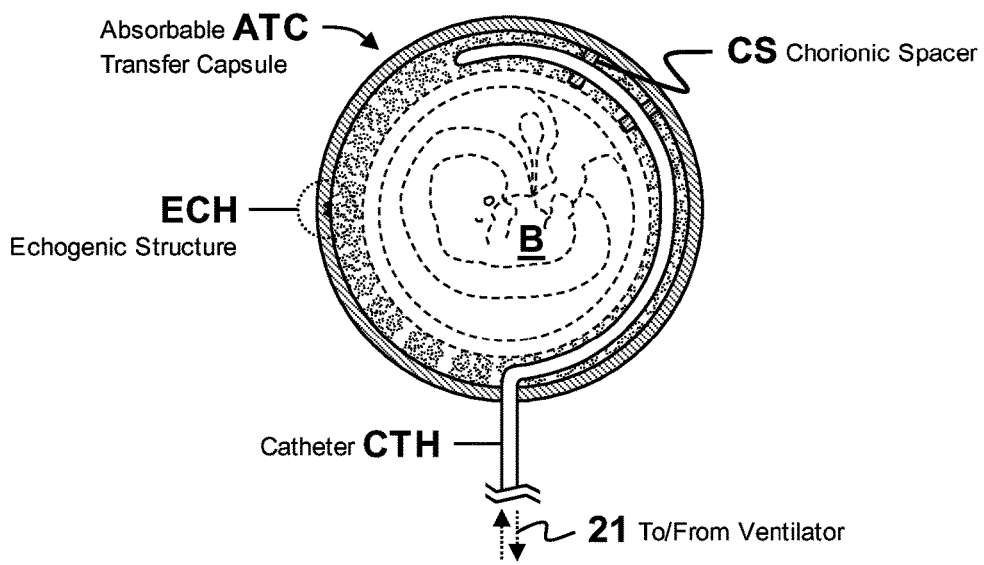

FIG. 10 is a side cross-sectional view of a baby B receiving in situ ventilation within an absorbable transfer capsule ATC according to the invention, and which capsule is being used as a vehicle for placing a ventilation catheter CTH and chorionic spacer CS in the uterus with the baby.

Figure 11:
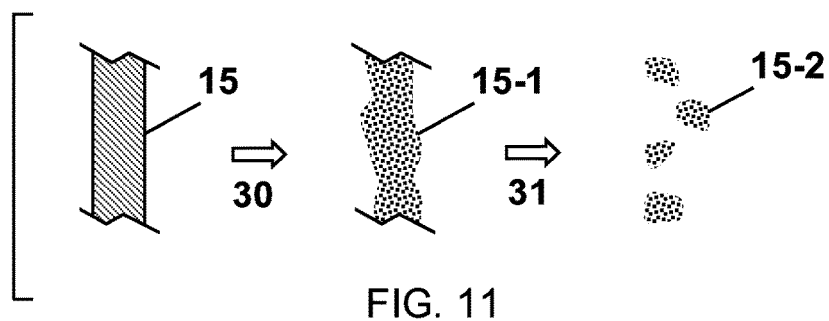
Figure 12:
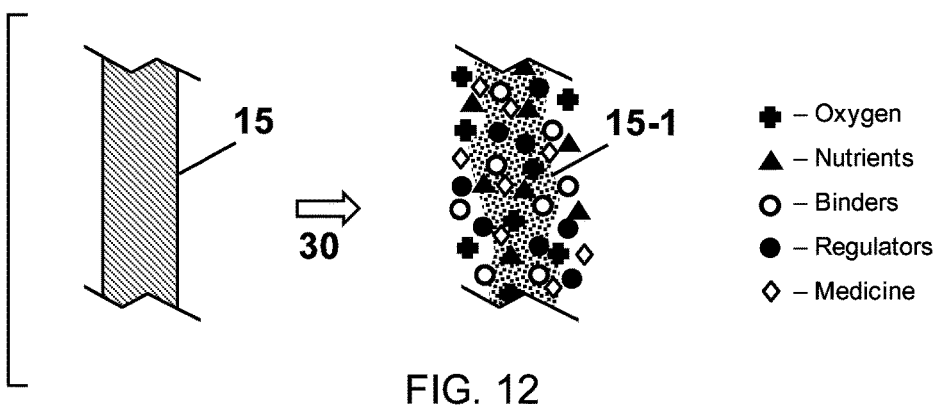

FIGS. 11 and 12 are side cross-sectional views of wall sections of an absorbable transfer capsule showing a dissolving and absorption of an absorbable material 15 forming capsule walls.

Figure 13:
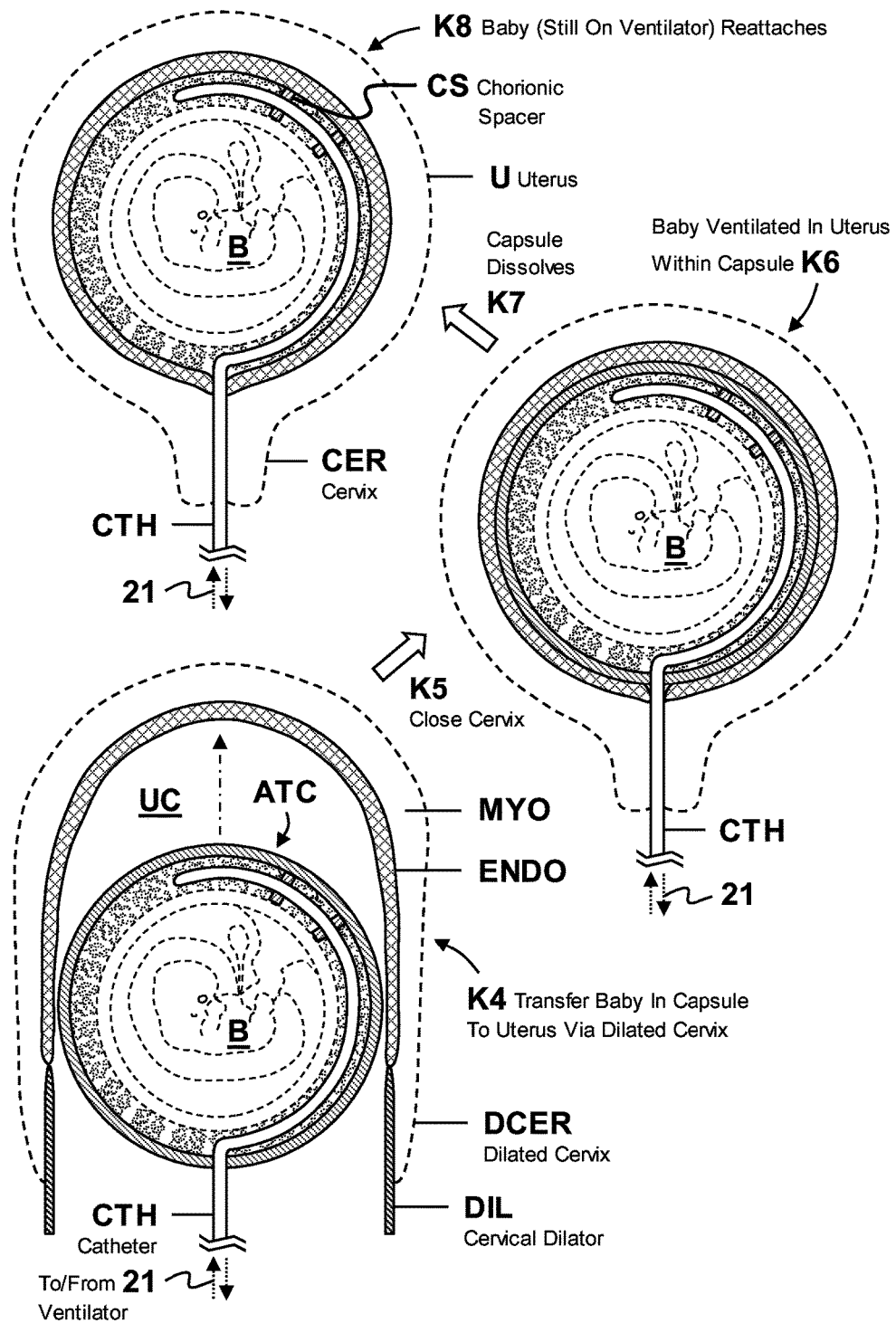

FIG. 13 is a median cross-sectional view of a transcervical reimplantation using an absorbable transfer capsule ATC according to the invention. This figure, depicting encapsulated transfer, is most descriptive of the invention. Cf FIG. 5, showing bare transfer.

Figure 14:
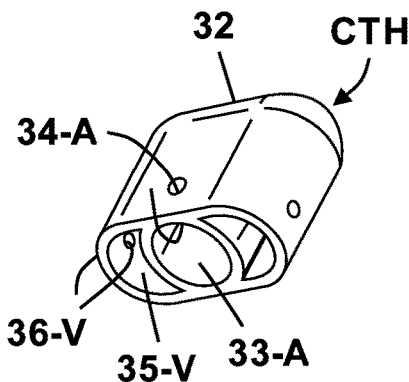

FIG. 14 is a perspective view of a distal section of an exemplary ventilation catheter CTH according to the invention.

Figure 15:
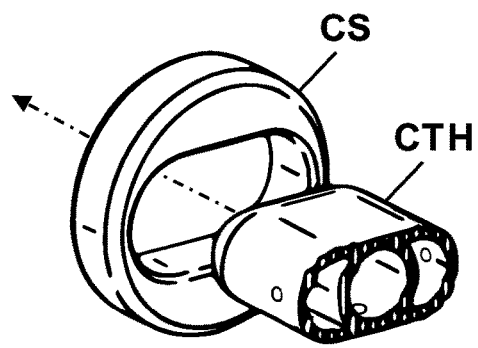

FIG. 15 is a perspective view of an exemplary chorionic spacer CS according to the invention, showing its relationship to the catheter CTH of FIG. 14.

Figure 16:
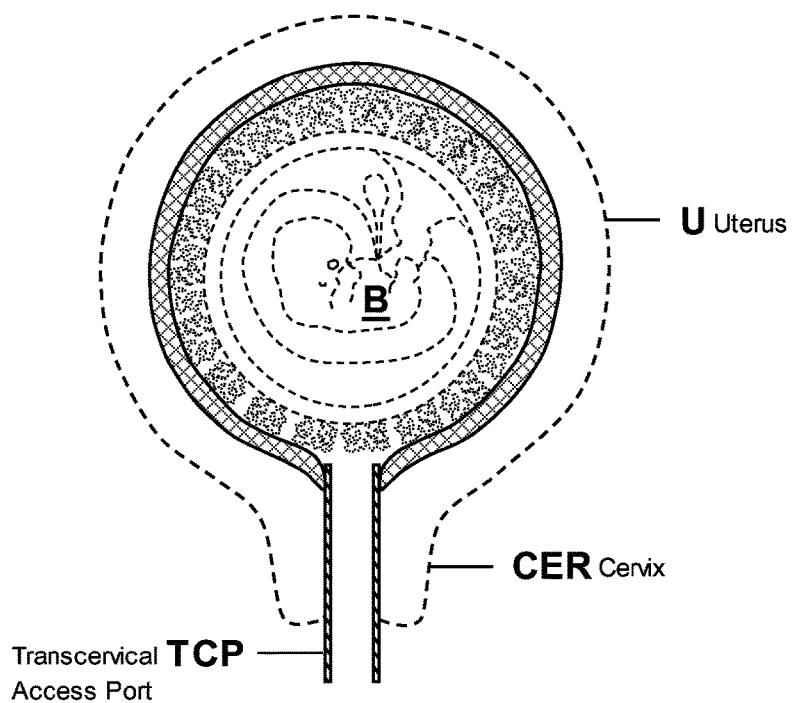

FIG. 16 is a median cross-sectional view of a uterus U having a transcervical access port TCP in place within the cervix CER for use according to the invention.

Note that the median cross-sectional views of FIGS. 5, 7, 8, 13, and 16 are depicted as viewed from the mother's left side, such that the baby B is shown oriented in the uterus U with the alluvia anterioris in the posterior fundal position.

Figure 17:
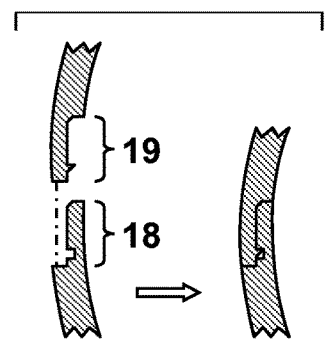

FIG. 17 is a side cross-sectional view of rim sections of top and bottom shells 16, 17 of the absorbable transfer capsule ATC of FIG. 9. This example depicts a slidable tongue-and-groove closure to join capsule halves.

Figure 18:
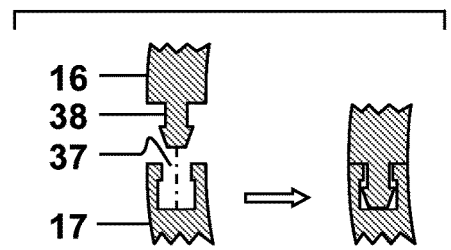

FIG. 18 is analogous to FIG. 17, except this example depicts a hole-and-peg closure to join capsule halves of a similar capsule.

Figure 19:
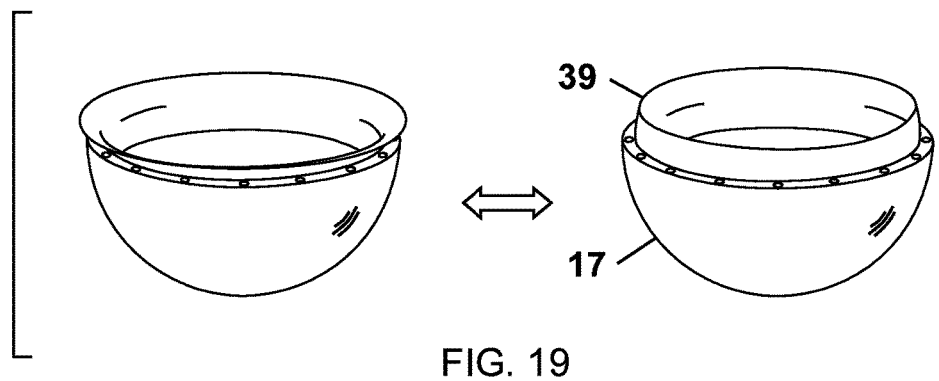

FIG. 19 is a side perspective view of an exemplary pinch guard 39 according to the invention.

Figure 20:
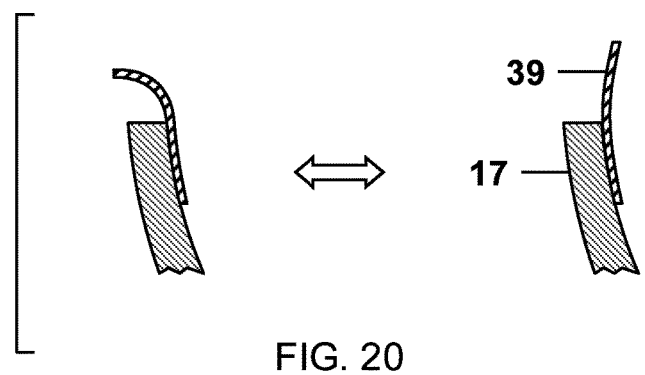

FIG. 20 is a side cross-sectional view of the pinch guard 39 of FIG. 19.

Figure 21:
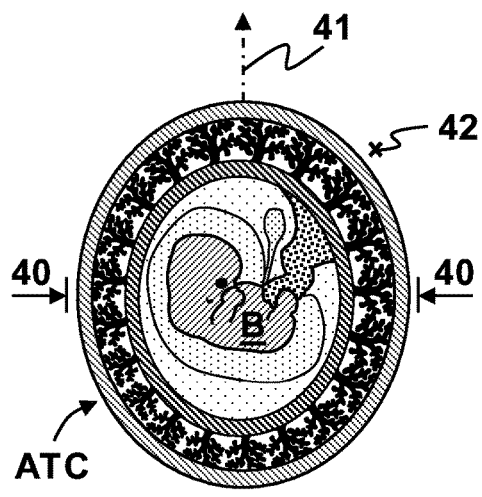

FIG. 21 is a side cross-sectional view of an absorbable transfer capsule ATC according to the invention having a reduced diameter 40 in the transverse plane of the cervix to facilitate entry and passage of the capsule through the cervix as it is introduced.

Figure 22:
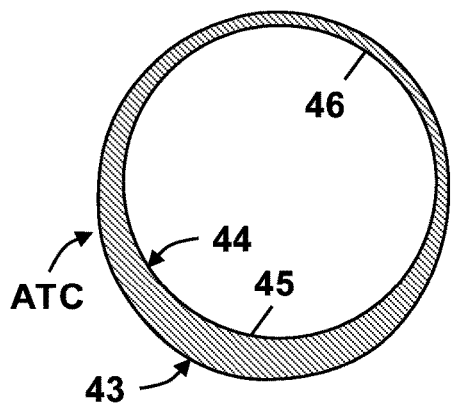

FIG. 22 is a side cross-sectional view of an absorbable transfer capsule ATC according to the invention having a uterus-fitting outer contour 43 and a baby-fitting inner contour 44.

Figure 23:
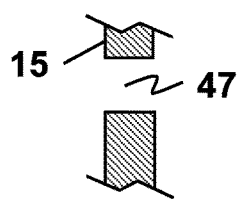
Figure 24:
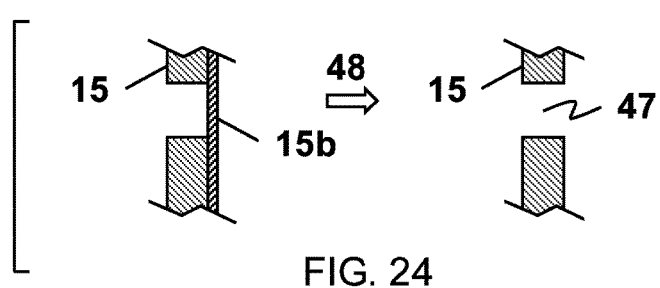
Figure 25:
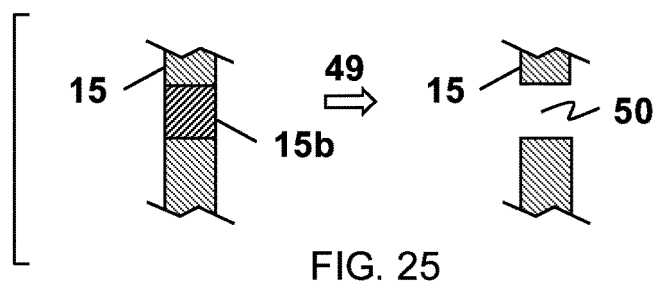

FIGS. 23, 24, and 25 are side cross-sectional views of wall sections of an absorbable transfer capsule according to the invention, showing an exemplary variety of ways in which holes 47, 50 may be disposed in the walls.

Figure 26:
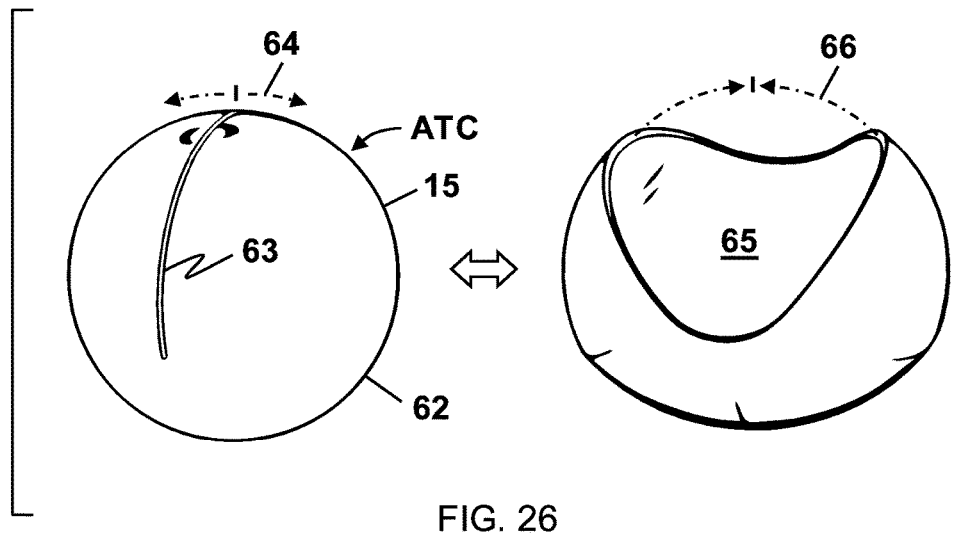

FIG. 26 is a side perspective view of an exemplary embodiment of an absorbable transfer capsule ATC according to the invention. This example depicts a soft shell type capsule structure for enclosing a baby and resembles a squeeze-type coin purse of the rubbery variety.

Figure 27:
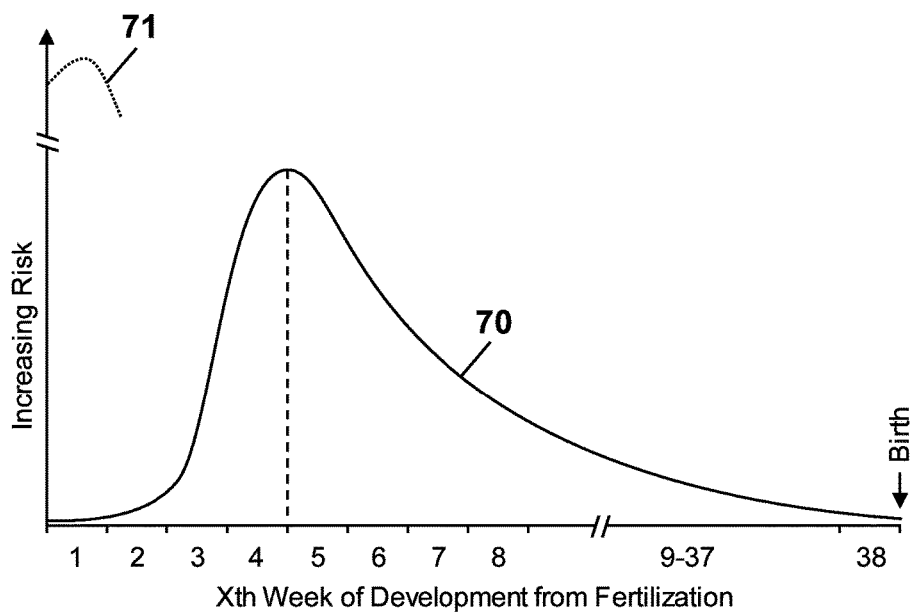

FIG. 27 is a graph based on literature reports of a risk of birth defects being induced by teratogens as a function of weeks of development.

Figure 28:
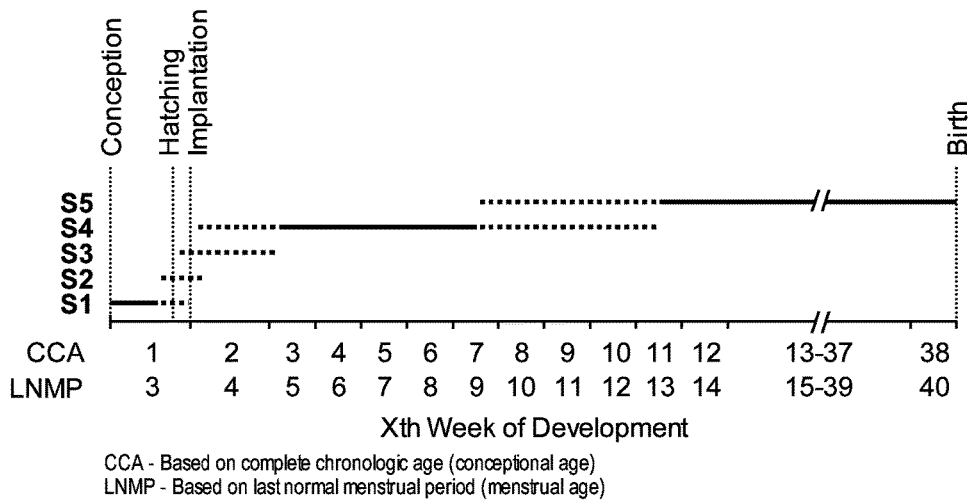

FIG. 28 is a graph based on literature reports of sequential stages of fluidic ventilation as a function of weeks of development.

Figure 29:
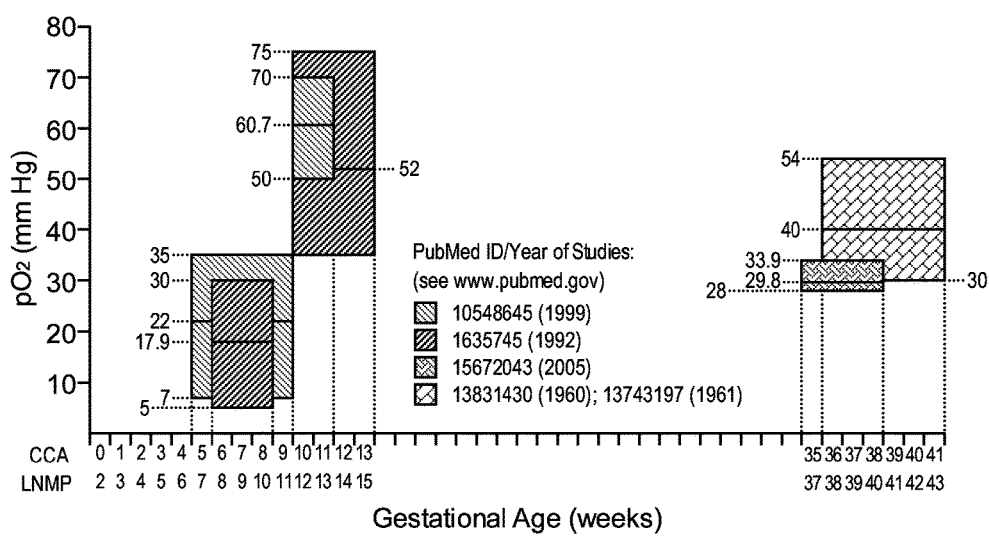

FIG. 29 is a graph based on literature reports of intervillous oxygen tension measurements taken during pregnancy.

Figure 30:
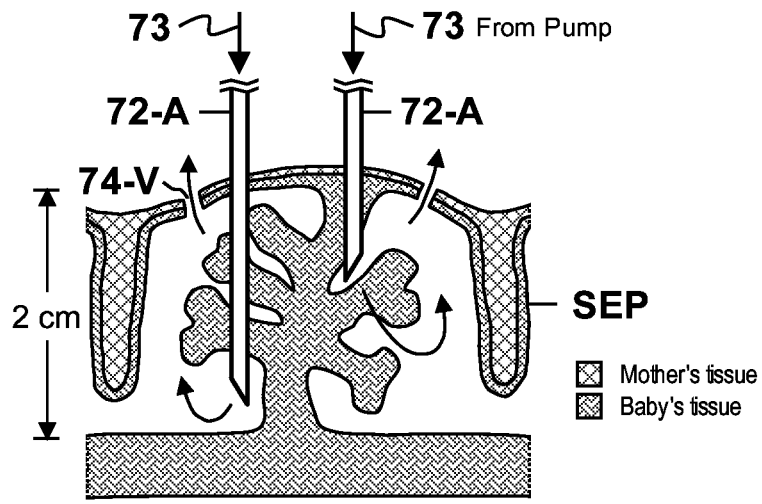

FIG. 30 is a side cross-sectional view of a cotyledon being perfused with a catheter system according to the art of Soydemir et al.

Figure 31:
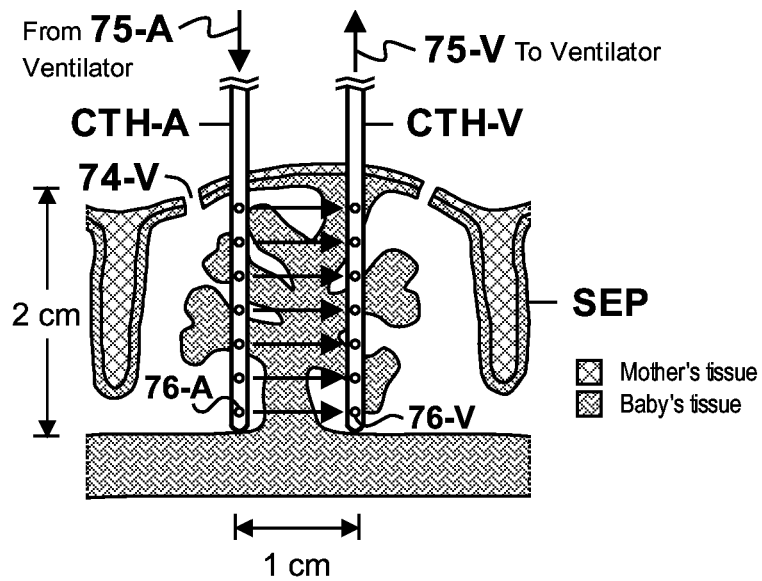

FIG. 31 is a side cross-sectional view of a cotyledon being ventilated with a catheter system according to the invention to provide a baby with fluidic ventilation.

Figure 32:
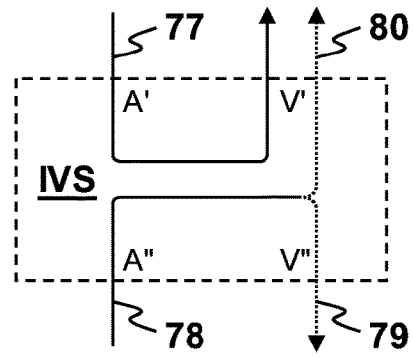

FIG. 32 is a schematic diagram of the intervillous space, illustrating several options of fluid being delivered and withdrawn from the intervillous space via an intrauterine ventilator according to the invention.

Figure 33:
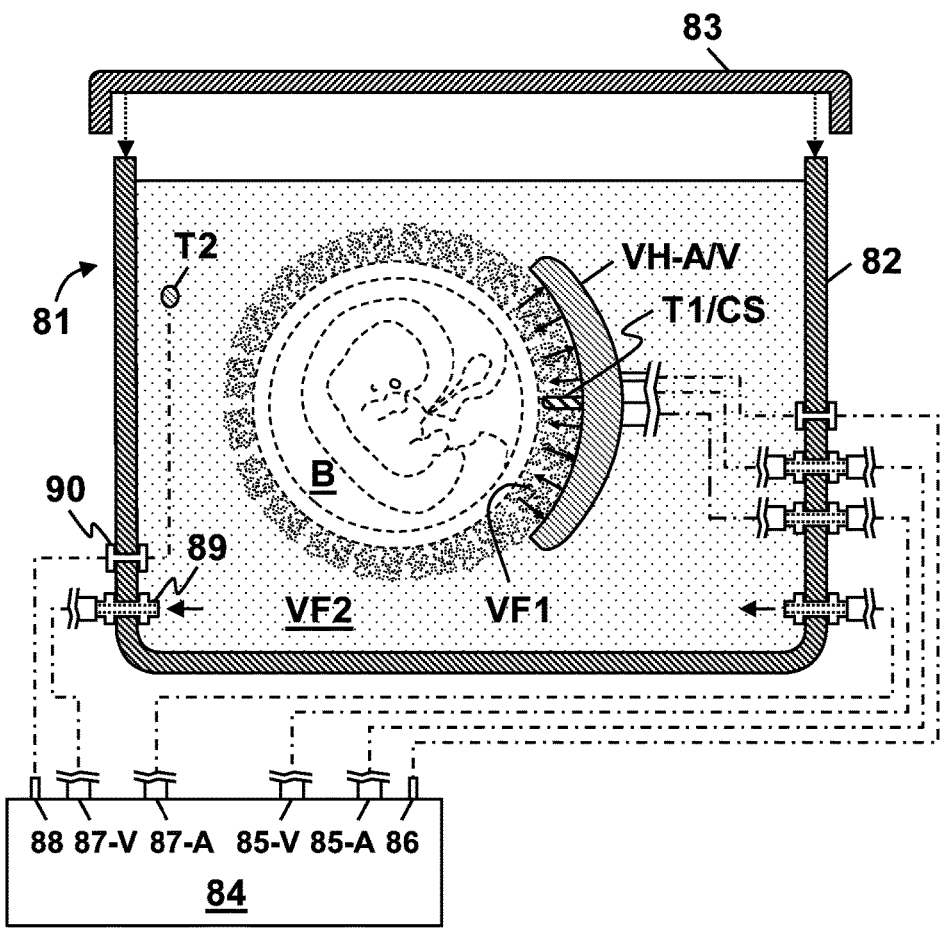

FIG. 33 is a side cross-sectional view of an exemplary embodiment of an open access alluvial incubator 81 according to the invention.

Figure 34:
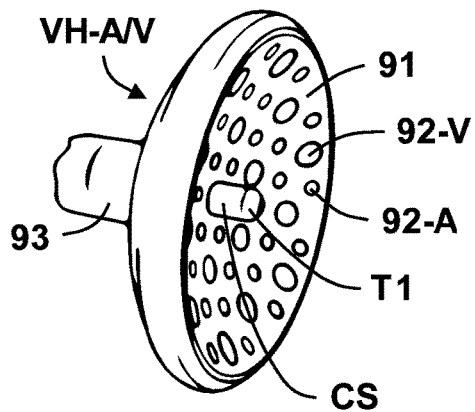

FIG. 34 is a side perspective view of an exemplary bidirectional ventilation head VH-A/V according to the invention as shown also in FIG. 33.

Figure 35:
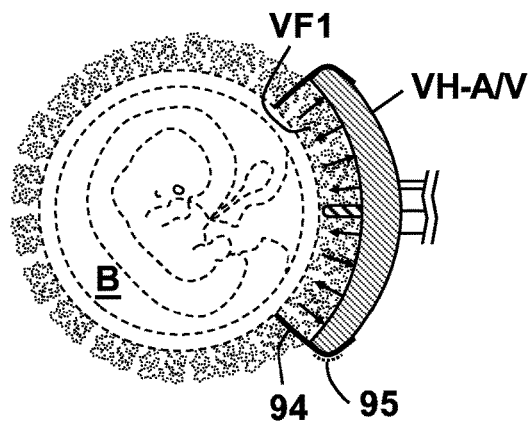

FIG. 35 is a side cross-sectional view of a modification of the bidirectional ventilation head VH-A/V shown in FIGS. 33 and 34.

Figure 36:
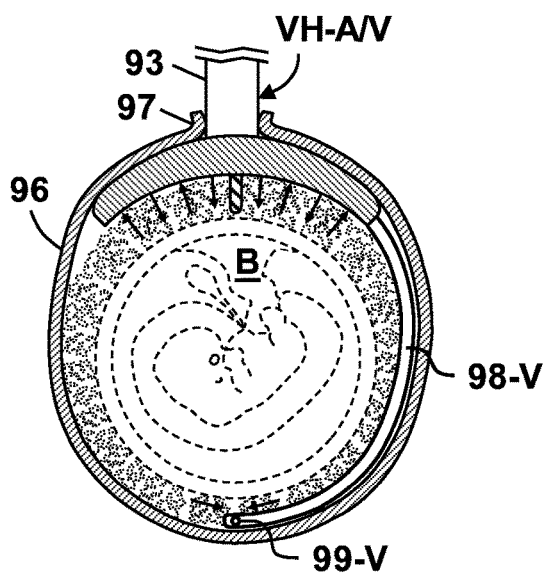

FIG. 36 is a side cross-sectional view of a variation of the incubator shown in FIG. 4.

Figure 1A:
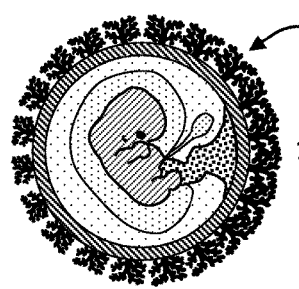
FIGS. 1A-1B are side cross-sectional views of substantially the whole body of a baby B almost seven weeks after fertilization.
Figure 37:
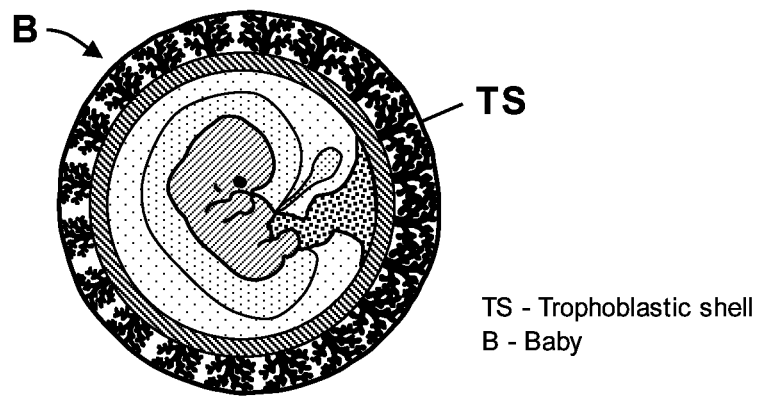

FIG. 37 is a side cross-sectional view of the whole body of a baby B almost seven weeks after fertilization. Cf FIG. 1A, showing substantially the whole body but with the trophoblastic shell TS removed.

Figure 38:
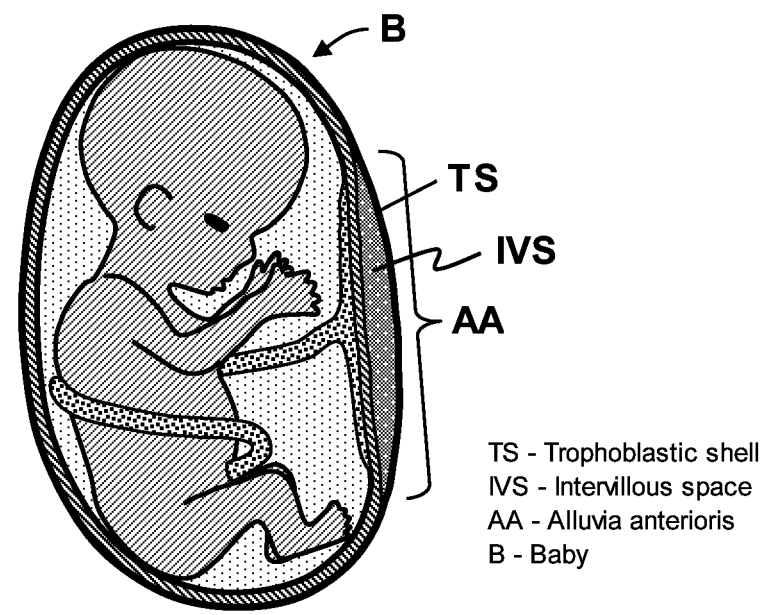

FIG. 38 is a side cross-sectional view of the whole body of a baby B a little over 12 weeks after fertilization.

DETAILED DESCRIPTION OF THE INVENTION

It is an object of the invention to provide a nondestructive means of ectopic pregnancy management, whereby a baby's gestational needs are satisfied without harm to the mother.

1. The Nature of Care

Babies do not breathe air during gestation. Instead their needs of respiration, feeding, hydration, warmth, and waste removal are accomplished by means of fluidic ventilation. FIG. 1A shows a baby B being fluidically ventilated with ventilating fluid VF. Fluidic ventilation is a liquid-phase ventilation and in this disclosure it is more formally called alluvial ventilation (pronounced "uh-LOO-vee-al," from the Latin alluere meaning to wash upon). This contrasts pneumatic ventilation which is the gaseous-phase ventilation of babies who breathe air, which is more formally called pulmonary ventilation.

The care of premature infants relying on pulmonary ventilation is well known, and the related incubators may be termed pulmonary, pneumatic, or air-based. The invention focuses instead on the care of premature infants relying on alluvial ventilation, and the related incubators may be termed alluvial, fluidic (microfluidic), or liquid-based.

In this disclosure, the natural provision for fluidic ventilation is called maternal ventilation. The invention teaches a mechanical ventilator to replace or supplement the maternal provision of fluidic ventilation. To emphasize it is for use with alluvial as opposed to pulmonary ventilation, this type of mechanical ventilator may be termed alluvial, fluidic (microfluidic), or liquid-based, as opposed to pulmonary, pneumatic, or air-based.

Infants breathing air may be called pulmonary infants, and those relying on fluidic ventilation may be called alluvial infants.

It should not be surprising that a microfluidic ventilator, which provides alluvial ventilation, is legally analogous to other mechanical ventilators, such as the pulmonary ventilator, which provides pneumatic ventilation. The main distinction is that in addition to satisfying the infant's needs of respiration, the microfluidic ventilator also satisfies the infant's needs of feeding, hydration, warmth, and waste removal. See *In the Matter of BABY "K"* (*Three Cases*), 16 F.3d 590 (4th Cir. 1994).

Hypoperfusion distress is a form of physiological distress, including but not limited to respiratory distress, that occurs when an alluvial infant is deprived of adequate fluidic ventilation, such that hypoxia (a state of oxygen deficiency), ischemia (a deficiency in the supply of blood or blood substances), malnourishment, dehydration, or toxicity from waste buildup are threatened due to inadequate fluidic ventilation. In view of the invention, fluidic ventilation by means of a fluidic ventilator is an indicated treatment for hypoperfusion distress.

The invention provides a means of ventilator treatment for alluvial infants who require it. Under the Emergency Medical Treatment and Labor Act, the Rehabilitation Act of 1973, and the Americans with Disabilities Act, hospitals are legally obligated to provide ventilator treatment to all infants who require it. See *Baber v. Hospital Corp. of America*, 977 F.2d 872 (4th Cir. 1992); *Brooks v. Maryland Gen. Hosp. Inc.*, 996 F.2d 708 (4th Cir. 1993); and, *In the Matter of BABY "K"* (*Three Cases*), supra.

2. Two Vital Points of Appreciation

According to the teaching of the invention, there are two vital points to appreciate on the subject of fluidic ventilation: First, it is more critical to ventilate an anterior aspect of the baby's gestational sac than a posterior aspect; second, in the maternal environment, even though uterine temperature is substantially constant at ~37° C. throughout pregnancy, a rate of maternal flow increases in thermal communication with the gestational sac to dissipate the added heat produced by the baby's growth, otherwise the baby would overheat and die.

A. First Point

FIG. 2A shows the formal aspect of the baby's body, also called the formal body FB; this is the "baby" part. FIG. 2B shows the peripheral aspect of the baby's body, also called the peripheral body. Although both the formal and peripheral aspects are part of the baby's body as a whole, they are related as astronaut is to spacesuit; thus the peripheral aspect is the "spacesuit" part, also called a fluidic or alluvial spacesuit S. According to the process known commonly as implantation, the baby quite literally plugs his or her spacesuit into the mother's body (viz. mother ship) for continuing life support. As long as the spacesuit is fluidically ventilated, the baby inside will continue to receive life support for the remainder of gestation.

Since the life support link between the baby and mother during gestation is a fluidic one, the invention teaches the operator to emulate and supplement the maternal provision for life support using fluidic technologies.

Figure 1B:

In this disclosure, the anterior aspect of the gestational sac is called the alluvia anterioris (AA) and the posterior aspect is called the alluvia posterioris (AP). As shown in FIG. 1B, the anterior aspect of the gestational sac (the alluvia anterioris AA) communicates physiologically with the baby's formal body via the umbilical cord (see FIG. 2A, indicating the formal body); here this is called the anterior route of life support. In contrast, the posterior aspect (the alluvia posterioris AP) is distinguished as that aspect which does not communicate with the formal body via the umbilical cord. In other words, the main load of life support for the formal body is handled by the anterior route, which traverses the umbilical cord, and so it is more critical to ventilate the anterior aspect of the gestational sac than the posterior.

Hence, it is vital for the operator to identify the anterior aspect of the gestational sac and to ensure by means of the technology of the invention that it is adequately ventilated.

B. Second Point

Ignorance of the second point has been tragic. In the early days of neonatal incubators, doctors maintained a constant incubator temperature. They thought they were acting in analogy to a constant uterine temperature. But they failed to appreciate a difference in flow-related heat dissipation. In the maternal environment, the rate of uterine blood flow increases with the baby's increasing growth, and so the added flow dissipates the added heat produced by the baby. But when ambient temperature is kept constant in an incubator with poor heat dissipation, the babies overheat as they grow, resulting in death.

Doctors eventually learned to monitor infant body temperature distinct from the ambient temperature provided by the interior of the incubator environment, and to lower the ambient temperature based on feedback from infant temperature to prevent overheating. See Cone, Jr., History of the Care and Feeding of the Premature Infant, Boston: Little, Brown, 1985, pp. 21-22. Though this is one way to solve the problem of overheating, failure to fully appreciate the underlying etiology in terms flow-related heat dissipation has led to a repeat of the same tragedy.

To give an example of the problem's persistence, at Boston IVF (Brookline, Mass.), which is a fertility clinic affiliated with Harvard University's Medical School, chief embryologist C. Brent Barrett responded in a manner contrary to my teaching in U.S. Pat. No. 6,694,175, saying: "The embryos that we incubate are microscopic in size and therefore, there is no difference in the temperature of the interior of the incubator and the embryo. We constantly monitor the temperature of our incubators and have conducted numerous studies to ensure that we maintain an optimal temperature for the embryos." (Barrett, "*Boston IVF Web Site Inquiry*," Personal Communication, Jul. 7, 2004.)

The human embryo is encapsulated in an egg having an eggshell approximately 120 microns in outer diameter. As one skilled in the art of microfluidics will appreciate, the microscopic size of the human embryo actually worsens the problem of poor heat dissipation, since convection is limited by a low Reynolds number in the microscopic regime. But in the uterine tube (fallopian tube), the beating of microscopic cilia provides for mechanical convection of uterine tubal fluid about the embryo, thereby providing flow-related heat dissipation. In contrast, by leaving embryos at a constant ambient temperature in a stagnant test tube or laboratory dish, the prior art has caused the deaths of the vast majority of children created by in vitro fertilization. For as the embryos reach even as little as 2-3 days old, their increase in internal heat production has already increased to the point of overheating in an environment of poor heat dissipation. Ignorant of this etiology, the prior art has been at a loss to explain why it cannot incubate past the end of the first week with any dependable success.

In view of these subtle lessons of history, it is vital for the operator to consider both the temperature and rate of flow of the fluid circulating in contact with the baby, in terms of their combined effect on maintaining the baby's temperature without overheating, so as to adequately dissipate the baby's internally produced heat which increases with growth. Hence, due to the baby's internal heat production, competent control of the parameters of thermoregulation requires the operator to appreciate an interrelationship between the temperature and flow rate of the ventilating fluid as it circulates in contact with the baby.

3. The Two Vital Points Revisited

The first and second points may be summed up by saying fluidic ventilation and thermoregulation are the two most critical functions of an incubator according to the invention, and these functions are interrelated. They are interrelated because: 1) ambient temperature is the temperature of the fluid in contact with the baby, and 2) the fluid's rate of flow over the baby affects the flow-related dissipation of his or her internal heat.

So when fluidically ventilating the baby, meaning when providing a flow of ventilating fluid over the gestational sac, a temperature and rate of flow of the ventilating fluid must be considered in order to provide thermoregulatory support. For accuracy it is necessary to monitor the baby's temperature and to adjust incubation parameters accordingly, especially the ambient temperature and rate of flow of the ventilating fluid. See U.S. Pat. No. 9,056,039; claims 1 and 2.

Except when needed to warm the baby, the ambient temperature of the ventilating fluid in contact with the baby should not be higher than an optimal patient temperature to be maintained. With the temperature of the ventilating fluid set lower than patient temperature, increasing the fluid's rate of flow over the gestational sac will lower the baby's temperature (due to an increase in flow-related heat dissipation); conversely, decreasing the flow rate will cause the baby's temperature to rise (due to a decrease in flow-related heat dissipation). But with the temperature of the fluid kept higher than the patient's, the baby's temperature will always rise, and increasing the rate of flow will speed the rise in temperature (due to the increase in thermal transfer).

Excessively high rates of flow will waste ventilating fluid and inhibit accumulation of endogenous substances produced by the baby that promote vitality. Excessively low rates will deplete the fluid of vital substances in proximity to the infant and cause waste buildup. To avoid flow rates that exceed predetermined acceptable ranges, the ambient temperature of the fluid can be raised or lowered. See U.S. Pat. No. 9,056,039; claim 2.

A difference between my incorporated teachings on fluidic ventilation and those of the present disclosure is it is much easier to monitor the baby's temperature once he or she has grown and is no longer microscopic in size. In this respect, the present disclosure teaches means of clinical thermometry comprising placing a temperature probe against the outside of the chorionic plate at the anterior pole (directly over the umbilical cord). Anterior readings are preferred over the posterior because the umbilical cord circulates heat from the baby's formal body. See FIGS. 1A-1B and 2A-2B.

Without being able to competently perform the critical functions of fluidic ventilation and thermoregulation, it would not be fair to say an alluvial incubator is of a competent medical quality. My incorporated teachings are the first to disclose medically competent technology for alluvial incubation, with emphasis on incubators for babies before implantation. The present teaching extends these teachings to the care of alluvial infants who have already implanted.

4. Age

The use of different reference schemes for the age of a conceptus can lead to ambiguity and confusion.

For example, gynecologists would have us believe conception occurs about four weeks after the start of pregnancy. They mark the start of pregnancy using the onset of the last menstrual period, which occurs two weeks before ovulation in a 28-day cycle; and although it is not the commonly accepted definition, the American College of Obstetricians and Gynecologists defines conception as an instance of implantation (the success of which implies averting the menstruation that otherwise would have started two weeks after ovulation).

The confusion can be significant. For example, gestational age measured from the last menstrual period (menstrual age) is sometimes mistaken for gestational age measured from fertilization (fertilization age) and vice versa; and, in giving chronological accounts of early development, authors may inadvertently switch from fertilization age to menstrual age without any notice.

To avoid confusion, a few words are given here on the subject of age.

There are two natural modes of human propagation: sexual and asexual. The sexual mode is known as fertilization. According to the asexual mode, a first baby propagates a second asexually; this is commonly known as identical twinning. When a first is conceived sexually and a twin is conceived asexually, the first is older than the twin by the time between fertilization and twinning. In this disclosure, conceptional age is the age of a conceptus defined by the time elapsed since propagation, whether by fertilization or asexual twinning. Conceptional age may also be called complete chronologic age (CCA), which is the total duration of individual existence measured in units of time. In contrast, chronologic age which is commonly expressed as the period of time elapsed from birth measures age only in an incomplete sense. Conceptional age measures the true age of the conceptus, in contrast to menstrual age which defines conceptus age by the time elapsed since the onset of the mother's last normal menstrual period (LNMP).

In this disclosure, the baby's age is acknowledged in reference to complete chronologic age, meaning conceptional age, as defined above.

For a rundown on a variety of ways of measuring age and development, see Dorland's Illustrated Medical Dictionary ($32^{nd}$ ed., Philadelphia, Pa.: Saunders, 2011) under gestation period, pregnancy (def. 2), and various entries under age; noted is that Dorland's uses the term conceptual instead of conceptional in reference to age.

Another source of confusion is that the total duration of existence starts at zero, but unit intervals of existence start at one. For example, the baby is zero weeks old during the first week of life, and the baby turns one week old at the start of the second week of life. Thus the baby is X units old during the X+1 unit of development. The baby turns X weeks old at the start of the X+1 week of development, and the Yth week of development ends when the baby turns Y weeks old. Thus development weeks X to Y cover the time from the baby turning X−1 to Y weeks old.

Adding to the confusion is inadvertence. Unit intervals of time form a series; in weeks: [week 1][week 2] [week 3] . . . [week N]. In contrast, age reflects a sum of elapsed units in the series. But some may speak interchangeably of the Nth interval and age N, despite being properly related as X is to X−1. As a consequence, to give an example, some may speak of the gestational age as being X weeks LNMP when in fact the baby is in the Xth week of development LNMP and the gestational age is really X−1 weeks LNMP; in such a case, the baby is in the X−2 week of development CCA (instead of X−1), during which he or she is X−3 weeks old CCA (instead of X−2).

Noted is that with clock time "X to Y" means from the start of X to the start of Y. But when writing about ages and periods of development, "X to Y" tends to mean from the start of X through the end of Y; but the corresponding chart or graph will read as going from X to Y+1 if units are marked on tick marks rather than in between them. To avoid confusion, it is preferable to mark successive units and ranges between tick marks when dealing with age and development, as shown in FIGS. 27, 28, and 29.

The above comparisons of menstrual age and conceptional age assume a two week difference between fertilization and the onset of the last normal menstrual period, although the actual difference varies with the duration of a woman's cycle and the timing of fertilization with respect to ovulation.

Due to the many sources of potential confusion, estimates of age and development should be interpreted cautiously and with suspicion until there is greater refinement in the art. This includes estimates given in this disclosure.

5. The Situation of Ectopic Pregnancy

FIGS. 3A-3B show a typical situation of ectopic pregnancy, which is specifically known as a tubal pregnancy, and more specifically as an ampullar pregnancy.

FIG. 3A shows a frontal cross-sectional view of the mother's reproductive tract indicating an ectopic pregnancy EP situated in one of the two uterine tubes UT (fallopian tubes).

The ancients regarded the uterus U as looking like a vase, such that the cervix CER is the neck of the vase (Latin "neck") and the fundus UF is at the bottom (Latin "bottom, base"). This can be seen by turning FIG. 3A upside-down. Despite looking like the bottom of a vase, the uterine fundus UF is taken to be located at the anatomical superior (top) of the uterus U and the cervix CER is taken to be located at the anatomical inferior (bottom) of the uterus.

The uterine tube UT is divided into three sections: the infundibulum INF at its distal (far) end, followed by the ampulla AMP, and the isthmus IST at its proximal (near) end which opens up into the uterine cavity UC. The infundibulum INF, which is the usual site of fertilization, has a fringe of finger-like projections known as fimbriae FIM where it opens into the abdominal cavity to capture an egg released from the ovary OV.

The uterine cavity UC communicates with the vaginal canal VC via the cervical canal CCN which traverses the length of the cervix CER. The anatomical internal os (Latin "a mouth, opening") of the cervix IOS opens up into the uterine cavity UC and the external os of the cervix XOS opens up into the vaginal canal VC.

The top left and right corners of the uterine cavity UC are the uterine cornua (singular cornu), also called the uterine horns, and the bottom corner is the isthmus of the uterus. The endometrium is the interior lining of the uterine cavity UC and the myometrium is the surrounding muscle which forms the bulk of the uterus U.

The baby is supposed to implant in the endometrium of the uterine cavity UC. An ectopic pregnancy occurs when the baby implants outside this cavity or in one of its three corners.

The ectopic pregnancy EP shown in FIG. 3A is known as a tubal pregnancy because the baby has implanted in the uterine tube UT, and more specifically as an ampullar pregnancy because the baby has implanted in the ampulla AMP of the uterine tube.

FIG. 3B is a cross-sectional view of the ectopic pregnancy EP taken about a line 3B in FIG. 3A, which shows a baby B implanted and growing inside the uterine tube UT.

In a normal pregnancy, a baby in the uterine tube lumen UCL travels the course of the uterine tube UT and implants in a wall of the uterine cavity UC by burrowing into the endometrium. But in the example of ectopic pregnancy shown in FIGS. 3A-3B, the baby B has instead burrowed into a wall of the uterine tube UT and implanted in the ampullar region AMP.

Because the blood flow and mucosa of the ampulla are rich and nourishing, babies often thrive in an ampullar pregnancy until the baby's growth causes the uterine tube to stretch beyond capacity, unlike the uterus itself which is made for stretching. Eventually the uterine tube will burst. This means almost certain death for the baby and may also kill the mother.

But it is worth noting, however, that in exceptionally rare cases a secondary ectopic pregnancy will result when a primary ectopic pregnancy breaches the uterine tube and the baby reimplants outside the uterus in the abdominal cavity. Such abdominal ectopic pregnancies have been known to result in healthy term delivery by cesarean section.

Yet rather than leaving such matters to chance, the invention teaches a means of ectopic pregnancy management to assist this natural ability of the baby to reimplant, so he or she can safely reimplant in the uterine cavity where the baby belongs.

6. Apparatus, Methods, and Compositions of Matter

According to the invention, the baby is surgically delivered from an ectopic pregnancy site with the gestational sac intact pending transfer to the uterus for reimplantation.

After delivering the baby, the usual customs of live birth are performed, such as recording vital statistics and filling out the birth certificate. There is no need to fill out the birth certificate again once the baby is reborn after reimplantation, since this is a consequence of treatments performed after the original birth.

A. Alluvial Incubator

According to the invention, an alluvial incubator comprises: an enclosure to maintain a premature infant in an environment of controlled temperature, oxygen, hydration, feeding, and waste removal; a cradle support; and, a mechanical ventilator for fluidic ventilation.

FIG. 4 shows an embodiment of the incubator comprising exemplary forms of the enclosure, cradle support, and ventilator.

Referring to FIG. 4, an exemplary alluvial incubator 1 comprises a fluidic ventilator 2 and an enclosure 3, wherein enclosure walls form a cradle support for a baby B.

According to the invention, a fluidic ventilator comprises: a reservoir for holding ventilating fluid; and, a circulator to circulate the fluid at a controlled temperature and rate of flow in contact with a baby in a manner of fluidic ventilation.

FIG. 4 shows an embodiment of the ventilator comprising exemplary forms of the reservoir and circulator for ventilating fluid.

Referring to FIG. 4, the ventilator 2 comprises a reservoir 4 to hold ventilating fluid VF and a circulator 5 to circulate the fluid VF in contact with the baby B in the manner of fluidic ventilation.

According to the invention, a circulator to circulate ventilating fluid comprises: means to urge fluid; and, a regulator to control at least a rate of flow.

The ventilator 2 shown in FIG. 4 is analogous to an intravenous (IV) treatment system. In one embodiment, the reservoir 4 is an IV bag or bottle containing the ventilating fluid VF which has been prewarmed by a temperature bath to an exemplary predetermined temperature of ~37° C.; and, the circulator 5 is a gravity drip system comprising a regulator 6 and a sterile tubing 7, whereby the fluid VF is urged to circulate in contact with the baby B by way of the tubing 7. In one embodiment of the gravity drip system, the regulator 6 comprises a drip chamber and a roller clamp for regulating or stopping flow.

In another embodiment, the circulator 5 is an infusion pump system wherein the regulator 6 comprises a drip chamber, an infusion pump, and an IV fluid warmer. The drip chamber eliminates air bubbles, the infusion pump urges the ventilating fluid VF and regulates a rate of flow, and the IV fluid warmer regulates fluid temperature by warming it to a predetermined temperature.

In one embodiment of the infusion pump system, the infusion pump and IV fluid warmer are responsive to feedback from patient temperature readings by means of a computer processor. See U.S. Pat. No. 9,056,039; claims 1 and 2.

In yet another embodiment, the circulator 5 includes a micropump to urge fluid.

In the embodiment shown in FIG. 4, the enclosure 3 comprises an incubator bag 8 that also serves as a cradle support for the baby B. The incubator bag 8 is a flexible, sterile bag for holding the baby and an amount of the ventilating fluid VF: An opening at one end is sized for entry of the baby, after which the incubator bag 8 is attached and sealed to the ventilator tubing 7 by means of a clamp 9; and, an opening at the opposite end provides a fluid exit port 10 for the fluid.

Referring to FIG. 4 in view of FIGS. 1A-1B, to operate the incubator 1 the baby B is placed and oriented in the incubator bag 8 with the alluvia anterioris AA facing the fresh ventilating fluid VF emerging from the ventilator tubing 7, and the waste fluid exits via the fluid exit port 10. This means the side of the gestational sac with the umbilical cord attached faces the fresh fluid emerging from the ventilator 2.

Thus the inventive incubator provides the baby with ventilating fluid of a predetermined content and at a predetermined temperature and flow rate. In this manner, the infant's needs of fluidic ventilation and thermoregulation will be satisfied, including the needs of oxygen, feeding, hydration, warmth, and waste removal.

Embodiments of the inventive incubator employing sensors and feedback from sensors to monitor and control parameters of the incubator environment will be appreciated by one skilled in the art in view of my incorporated teachings.

Although not shown in FIG. 4, a temperature sensor is advantageously placed in contact with the baby for patient temperature readings. Preferably the sensor touches against the chorionic plate over the umbilical cord, and a side of the sensor facing opposite the chorionic plate is thermally insulated to shield the sensor from heat dissipation by the flow of ventilating fluid.

Referring to FIG. 4, the fluid exit port 10 may be provided with sterile tubing sealed to the incubator bag 8; the content of the exiting fluid may be monitored. In an alternate embodiment, fluid from the fluid exit port 10 may be recirculated via tubing, and the content of the fluid may be monitored and supplemented.

One skilled in the art of incubation will appreciate that the ambient temperature of the air outside the incubator enclosure is maintained to limit heat loss from the incubator.

An incubation bag may be made of a thermally insulating material or wrapped in a thermally insulating material. A housing may be provided to enclose a temperature bath in thermal contact with the incubation bag.

In another embodiment, the incubator bag is replaced by a rigid cradle support that intimately encloses the baby, the rigid enclosure having halves that open and close to provide entry for the baby, as well as openings to admit access, fluid lines, sensors, and accessories.

In another embodiment, a baby is submerged in an open access enclosure filled with an ambient quantity of ventilating fluid that is circulated by a first ventilator, and a cradle support is provided by a forceps for holding the baby in place within the enclosure; in addition to the ambient quantity of ventilating fluid filling the enclosure, a second ventilator circulates streams of ventilating fluid directed specifically at the gestational sac, with emphasis on the alluvia anterioris. To conserve expense, the directed fluid may be of a richer content than the ambient quantity; in such a case, a surrounding barrier or seal may be provided in contact with or in proximity to the gestational sac to segregate fluids of different qualities within the incubator. A removable lid or other closure for the enclosure is provided for when access is not required.

An enclosure filled with ventilating fluid at a predetermined temperature can also be used to wash the baby after delivery. Washing can be assisted with fluidic instruments to pour or circulate ventilating fluid over the baby and away. Infant baptisms may be performed using water of a content that is physiologically and sacramentally compatible.

Enclosures may be double-walled to promote thermal and radiant heat insulation.

FIG. 4 shows the baby B being ventilated by a stream of ventilating fluid VF that emerges from a single stream as provided by a single tubing 7 and in a single flow direction. One skilled in the art of microfluidics will appreciate that a fluidic instrument having a plurality of fluid ports may also be used to provide streams of fluid, in likeness to a shower head submerged under water. According to the invention, such instruments may be called ventilation heads; less favored but analogous terms are perfusion head and irrigation head. A bidirectional ventilation head may be used to direct flow in opposite directions over a given area of the gestational sac. A combination of unidirectional instruments may also be used to provide bidirectional flow over a given area.

The invention provides surprising advantages over the prior art. For example, though it is impossible to care for an alluvial infant in a pulmonary incubator before the lungs are formed, the alluvial incubators of the invention make caring for them feasible, and perhaps even easier than caring for the earliest pulmonary infants, by preserving the gestational sac intact during delivery and employing fluidic instead of pneumatic technologies. Not only that, but by employing the inventive incubators in the management of ectopic pregnancy, an advantage over prior art efforts to save the baby is that the baby can be maintained in a controlled environment while the mother's uterus is prepared to receive her baby. And even in cases where reimplantation is not indicated, the inventive incubators provide for the baby's continuing or hospice care.

B. Transcervical Reimplantation

Though accepting the possibility of reimplantation through an incision made in the uterus as taught by the prior art, instead the invention prefers a transcervical route.

FIG. 5 shows a median cross-sectional view of a transcervical reimplantation according to the invention. According to the process of transcervical reimplantation, in a first step K1 the cervix CER is dilated by means of a dilator DIL and the baby B is transferred into the uterine cavity UC through the dilated cervix DCER. In a second step K2, the cervix CER is closed. In a third step K3, the baby B is allowed to reattach naturally inside the uterus U.

Indicated in FIG. 5 are the endometrium ENDO to which the baby B attaches upon reimplantation, the surrounding muscle known as the myometrium MYO, and the posterior wall of the uterine fundus UFP.

According to the invention, the operator is taught to observe an orientation of the gestational sac in the uterine cavity when performing reimplantation, such that it is critical for the operator to identify and orient the alluvia anterioris when transferring the baby to the uterus.

Facing the alluvia anterioris toward the internal os of the cervix is taken to be disfavored due to the complication of placenta previa. Facing the alluvia anterioris in a low-lying position is taken to be less favored than a fundal position. In this disclosure, a posterior fundal position is taken to be preferred, although further data will be required to determine this fully.

Referring to FIG. 5, the baby B is shown reimplanted with the alluvia anterioris in the posterior fundal position. In other words, that area of the gestational sac which is joined to the umbilical cord has been oriented to face the posterior wall of the uterine fundus UFP.

An advantage of transcervical reimplantation over uterine incision is that the incision will provoke an added inflammatory reaction which may impede implantation.

C. In Situ Ventilator

The invention further teaches an in situ ventilation of the baby, so the baby will receive fluidic ventilation at the ectopic pregnancy site by means of a ventilating catheter.

Referring to FIG. 6 in view of FIGS. 3A-3B, as the uterine tube UT is surgically opened 20 to deliver the baby B from the ectopic pregnancy site, the baby is ventilated by means of a catheter CTH in fluidic communication with a ventilator 21 according the invention, so as to circulate ventilating fluid VF over the baby's gestational sac during the delivery process. The baby is said to be receiving in situ ventilation with the aid of a ventilator.

Referring to FIG. 6 in view of FIG. 1A, although FIG. 1A shows substantially the baby's whole body, missing is a trophoblastic shell TS. As shown in FIG. 6, the trophoblastic shell TS forms a thin layer at the outer extremity of the baby's peripheral body and is continuous with the distal ends of selected chorionic villi which are attached thereto, called anchoring villi. For the stage of development shown, the case of delivery depicted in FIG. 6 is that the trophoblastic shell TS remains largely adherent to the uterine tube UT, so that the result of delivery is that the trophoblastic shell TS is removed, as shown in FIG. 1A. However, especially in later stages of development, the trophoblastic shell may remain intact. In such a case, either the trophoblastic shell must be removed by the operator, at least with respect to the alluvia anterioris, or else the trophoblastic shell and any adherent maternal tissue will have to be penetrated by microfluidic instruments to provide fluidic ventilation within the intervillous space.

Although FIG. 6 shows only a supply of fresh ventilating fluid VF coming through the catheter CTH from the ventilator 21, bidirectional ventilation may be applied with a bidirectional catheter system. Although FIG. 6 shows a catheter CTH having a simple tubular termination, in general a catheter may terminate with a microfluidic instrument to provide streams or a spraying of fluid.

In an embodiment of an instrument to provide in situ ventilation while delivering a baby, blades of a delivery forceps are provided with microfluidic ports for fluid outlet and inlet in communication with a network of microfluidic channels to ventilate the baby contained by the forceps by means of a ventilation catheter attached to the forceps. Such may be called a microfluidic (delivery) forceps.

A catheter, hollow needle, or other fluidic instrument or device may be adapted to entry into the uterine tube or other organ or cavity so as to introduce fluidic ventilation therein.

The uterine tube may either be left in place while the baby is delivered or a portion of the uterine tube containing the baby may be removed with the baby still inside and placed in an enclosure containing ventilating fluid while the operator works on separating the baby from the uterine tube without damaging the gestational sac. Either way, the baby can be put on in situ ventilation to avoid an interruption of fluidic ventilation during delivery procedures.

D. Intrauterine Ventilator

An in situ ventilator serving the baby in the uterine cavity is more specifically called an intrauterine ventilator according to the invention.

FIG. 7 shows a median cross-sectional view of a baby B in the uterus U receiving in situ ventilation by means of an intrauterine ventilator. Referring to FIG. 7, a ventilating catheter CTH is placed in the uterine cavity in fluidic communication with a ventilator 21 to provide the baby with ventilating fluid in the uterus. The catheter CTH is shown placed in the uterus U in the intervillous space between the chorionic plate and the endometrium ENDO. Referring to FIG. 7 in view of FIG. 1B, note here that the catheter CTH is positioned to ventilate the alluvia anterioris AA; though not shown explicitly, a series of fluid ports is preferably disposed along a length of the catheter to cover at least an area of the alluvia anterioris being traversed.

As shown in FIG. 7, it is preferable to introduce the ventilating catheter CTH into the uterus transcervically. The catheter may be placed with the baby during transfer, or afterward either manually or by means of a guidable or steerable catheter.

Though not preferred, a catheter or other microfluidic instrument for fluidic ventilation may also be placed in the uterus via the uterine orifice of the uterine tube or through the uterine wall, and fluidic communication may be established transabdominally or transvaginally with an external ventilator or internally using a micropump ventilator disposed in the abdomen.

Hunter teaches an artificial fallopian tube comprising an internal or external micropump to provide "an adequate supply of fresh nutrient solution" for an embryo transiting a prosthetic fallopian tube in an egg within the maternal body. See U.S. Pat. No. 4,574,000; column 5, lines 38-50; FIG. 5. Since the baby is inside the tube with the flowing nutrient solution, he teaches (column 5, lines 42-50) "a pulsatile flow will cause the nutrient solution to advance through the device more rapidly than the egg" to provide a fluid circulation relative to the egg.

An intrauterine ventilator according to the invention may also be used to treat placental abruption and other causes of hypoperfusion. It may also be used to treat growth restriction and other cases where supplemental ventilation is indicated.

In addition to ventilating fluid, which may further include medication and other beneficial substances for the baby, intrauterine catheters may also deliver beneficial substances for the mother and to aid the receptivity of her uterus to reimplantation.

Fluid returned by intrauterine catheters may be sampled to determine a health status of the baby and mother and the progress of reimplantation.

In contrast to prior art efforts to save and transfer the baby to the uterus from an ectopic site without the benefit of a ventilator, an advantage of alluvial ventilators according to the invention is that they allow the baby to be fluidically ventilated without interruption during pregnancy transfer procedures, including during delivery, incubation, and reimplantation.

E. Chorionic Spacer

In some cases of pregnancy transfer, the uterus will be too large. In such a case, material may need to be added beneath the alluvia posterioris to bolster the baby in the uterus to ensure abutment of the alluvia anterioris to the endometrium.

But in other cases, the uterus will be a bit tight fitting, though not too small to preclude transfer. However, a problem with a tight fitting uterus is that the chorionic villi will be compacted such that the intervillous space loses its fluidic patency, and this may cause the baby to experience such ill effects of hypoperfusion as toxic waste build up, malnutrition, and suffocation.

To ensure the chorionic villi are not compacted in a tight fitting uterus, the invention teaches a chorionic spacer. As shown in FIG. 8, the chorionic spacer CS is a structural member sized to maintain a predetermined minimum distance of spacing between an inner wall of the endometrium and an outer wall of the chorionic plate. Thus the spacer CS maintains the fluidic patency of the intervillous space IVS despite compression forces exerted between the chorionic plate and a wall external to the baby, such as the uterine wall or a wall of an absorbable transfer capsule (ATC) according to the invention. Referring to FIG. 8 in view of FIG. 1B, note that the spacer CS is positioned to maintain the fluidic patency of the alluvia anterioris AA.

Walls or surfaces of an ATC, other enclosure, cradle support, forceps, or other device making contact with the gestational sac may be provided with raised projections in the manner of a chorionic spacer. For example, referring to FIG. 4 an inside wall of the incubator bag 8 may be provided with a pattern of protuberances such as bumps, posts, or grooves to maintain fluidic patency within the intervillous space; indentations may also be provided.

As shown in FIG. 8 in view of FIG. 1B, the usual case of a chorionic spacer will be to maintain the fluidic patency of the intervillous space IVS with respect to the alluvia anterioris AA. But in some cases a chorionic spacer may be indicated to maintain the fluidic patency of the alluvia posteriors AP, e.g., for posterior drainage.

For example, referring to FIG. 4, use of a posteriorly situated chorionic spacer may be indicated to maintain the flow of the ventilating fluid VF as it goes around the alluvia posterioris and out the fluid exit port 10. Otherwise, in the position shown, the flow may be blocked by the baby's weight pressing against the incubator bag 8. This is especially indicated once the posterior chorionic surface has been left relatively smooth (chorion laeve) due to a disappearance of its chorionic villi with development, unlike chorionic villi at the anterior which grow by elaborating their branching to form a leafy surface (chorion frondosum). Noted aside is that a flow meter combined with an alarm to signal predetermined flow conditions may be provided to monitor fluidic patency.

In contrast to prior art efforts to reimplant a baby in the uterus without the benefit of a chorionic spacer, the inventive use of a chorionic spacer is designed to avert compaction of the chorionic villi in a tight fitting uterus to maintain a free flow of ventilating fluid in the intervillous space for healthy growth.

F. Absorbable Transfer Capsule

The method of reimplantation shown in FIG. 5 may be called a "bare" transcervical transfer because the baby is bare. There are several problems with bare transfer.

One problem is the mother's uterus may experience some inflammation due to the transfer procedure, and the inflammatory reaction may inhibit reimplantation. This is especially true if an incision is made in the uterus.

Another problem is the baby may be injured during bare transfer, especially when being transferred into a tight fitting uterus or through a small incision or through a cervix which is difficult to open wide enough to permit transfer without compressing the baby. Bare transfer also exposes the baby to the environment of the operating room.

Another problem is that placing a ventilation catheter or chorionic spacer in the uterus transcervically may prove difficult after the baby has already been transferred. There is also a risk of injury if such devices are introduced in a cumbersome manner at the same time as transfer.

The invention solves these problems by means of an absorbable transfer capsule (ATC). The ATC forms an absorbable enclosure around the baby to provide a temporary shelter for the baby while being transferred to the uterus. The ATC also provides a convenient vehicle for placing devices such as a ventilation catheter or chorionic spacer into the uterus with the baby. Being comprised of at least one absorbable material, after the baby is transferred to the uterus the ATC enclosure dissolves according to a predetermined schedule and is absorbed so the baby can reattach.

FIG. 9 shows a side perspective exploded view of an exemplary embodiment of an absorbable transfer capsule according to the invention. Referring to FIG. 9, an exemplary absorbable transfer capsule ATC is like a plastic Easter egg to enclose the baby, except it is made of an absorbable material 15. This example provides structural support when needed to protect the baby, e.g., in a tight fitting uterus. To enclose the baby, top and bottom shells 16, 17 of the capsule are closed over the baby and lock into place via inner and outer sliding members 18, 19 disposed on the rims of the shells.

FIG. 10 shows a side cross-sectional view of a baby B enclosed within an exemplary absorbable transfer capsule ATC according to the invention. In this case, the capsule is being used as a vehicle for placing a ventilation catheter CTH and a chorionic spacer CS into the uterus with the baby. The capsules shown in FIGS. 9 and 10 are substantially the same, except the one shown in FIG. 10 has been modified to include a port for the ventilation catheter.

The FIG. 10 embodiment also shows an exemplary echogenic structure ECH disposed in a wall of the capsule to assist detection of capsule orientation by ultrasound. The echogenic structure ECH may be formed as an impression in the capsule wall according to the art. Echogenic structures may also be disposed in the ventilation catheter or chorionic spacer.

Referring to FIG. 10, the ventilation catheter CTH is in fluidic communication with an external ventilator 21 to provide the baby B with fluidic ventilation in the capsule ATC.

Though not shown in FIG. 10, other auxiliary devices, such as a sensor connected to an external sensing device, may also be attached to the ATC and transferred with the baby.

According to the invention, exemplary devices to introduce into the uterine cavity for the auxiliary benefit of pregnancy transfer procedures include a ventilation catheter, chorionic spacer, optical probe, sensory probe, electrode, or transducer. According to the art, the optical probe may be a fiber optics device or a micro-opto-electro-mechanical systems (MOEMS) device. According to the art, the sensory probe may sense a temperature, pH, electrophysiological signal, or pressure. Or, it may sense an amount or concentration of metabolites such as oxygen, glucose, pyruvate, or lactate; of wastes such as carbon dioxide, urea, uric acid, creatinine, or bilirubin; of hormones such as chorionic gonadotropin; or of antibodies. According to the art, the electrode may detect or emit an electrophysiological signal. According to the art, the transducer may detect or emit an electrical, magnetic, electromagnetic, optical, mechanical, chemical, thermal, or acoustic signal. According to the invention, such devices are best introduced into the uterine cavity by using an ATC as a convenient vehicle for placing them in the uterus along with the baby.

FIG. 11 illustrates the dissolving and absorption of an absorbable material 15 forming the walls of an absorbable transfer capsule. Referring to FIG. 11, once the capsule is placed in the uterus, the absorbable material 15 dissolves 30 after a predetermined amount of time to form a dissolving material 15-1 which is then absorbed 31 by the mother's uterus and/or baby as a dispersing material 15-2.

Beneficial substances for the baby and mother may be added to the absorbable material forming the walls or other structures of the absorbable transfer capsule. Exemplary substances include oxygen, nutrients, binders (e.g., for waste), regulators (e.g., to stimulate the baby's growth or the receptivity of the uterus), and medicine (e.g., antibiotics). Such substances may be released from the absorbable material at a predetermined schedule. They may migrate out of the absorbable material 15 before its dissolution or, as shown in FIG. 12, they may be released as it dissolves 30. Aggregates may also be released having additional time-release coatings.

G. Reimplantation Using a Transfer Capsule

FIG. 13 shows a median cross-sectional view of a transcervical reimplantation using an absorbable transfer capsule according to the invention. In this example, a baby B is placed in an absorbable transfer capsule ATC having a ventilation catheter CTH and a chorionic spacer CS. The baby B is ventilated by means of the ventilation catheter CTH in fluidic communication with an external ventilator 21. See FIG. 10. The operator is taught to take care to ensure the baby is oriented within the capsule so that when implanted the alluvia anterioris will observe a preferred orientation in the uterine cavity UC, for example, a posterior fundal orientation UFP. See FIG. 5 in view of FIG. 1B. Referring to FIG. 13, in a first step K4 the cervix CER is dilated by means of a dilator DIL and the baby B in the absorbable transfer capsule ATC is transferred into the uterine cavity UC through the dilated cervix DCER. In a second step K5, the cervix CER is closed. In a third step K6, the baby B continues to be ventilated in the uterus while still inside the absorbable transfer capsule ATC. In a fourth step K7, the absorbable capsule ATC dissolves to leave the baby's bare gestational sac abutted to the endometrium ENDO. In a fifth step K8, the baby B is allowed to reattach inside the uterus U while still on the ventilator 21.

A similar procedure is observed when introducing the capsule through an incision in the uterus. In this case, the proximal end of the catheter is preferably threaded through the incision and out through the cervix for transcervical connection to an external ventilator before the baby is placed in the capsule. Alternatively, the catheter proceeds through the uterine wall or the uterine orifice of the uterine tube.

H. Miscellaneous

In this disclosure, the term arterial (A) is used in reference to fresh ventilating fluid, as well as in reference to an instrument, fluid port, fluid line, or flow direction for providing fresh ventilating fluid, also called arterial ventilating fluid, or simply arterial fluid; conversely, the term venous (V) is used in reference to waste fluid. This is in analogy to maternal ventilation, which is supplied by arterial flow and removed by venous flow. The symbol A/V is used for bidirectional flow.

FIG. 14 shows a perspective view of a distal end section of an exemplary A/V ventilation catheter according to the invention. Referring to FIG. 14, the catheter CTH is capped at its distal end 32 and contains three channels: a central channel 33-A for arterial fluid having a series of arterial fluid ports 34-A disposed on a bottom face, and two side channels 35-V for venous fluid having a series of venous fluid ports 36-V disposed on left and right sides. In operation, the bottom face is the face of the catheter that faces the chorionic plate.

Advantageously, the catheter of FIG. 14 delivers arterial (fresh) ventilating fluid toward the chorionic plate in the configuration shown in FIG. 13 while venous (waste) fluid is removed from the intervillous space. Although the catheter of FIG. 14 provides bidirectional circulation, separate catheter lines for arterial and venous flow may be also employed.

An exemplary process for making the catheter of FIG. 14 includes extrusion. Of note, my incorporated teaching discloses a layer-based microfluidic catheter for transcervical use. See U.S. Pat. No. 8,292,798; column 24, line 26 to column 29, lines 34.

The A/V catheter example of FIG. 14 is not meant to be limiting. As notable variations, both the top and bottom faces may contain arterial ports; the indicated flow directions may be reversed; one channel each for arterial and venous flow may be provided; and, arterial and venous ports may be staggered rather than placed side by side as shown.

FIG. 15 shows a perspective view of an exemplary chorionic spacer CS according to the invention, including its relationship to the catheter of FIG. 14. Referring to FIG. 15, the chorionic spacer CS consists of a ring adapted to receiving the catheter CTH therethrough. The spacer is sized with a diameter to provide a predetermined minimum spacing between the chorionic plate and the endometrium. See FIG. 13.

The operator is cautioned that an amount of spacing provided between the chorionic plate and endometrium by the chorionic spacer must not be so great as to prevent the chorionic villi from abutting the endometrium; rather, the purpose of the chorionic spacer is to prevent compaction of the chorionic villi so as to preserve the fluidic patency of the intervillous space.

A plurality of chorionic spacers according to the exemplary embodiment of FIG. 15 may be inserted onto a given catheter with predetermined spacing between successive spacers. Multiple catheters may also be employed according to ventilation requirements.

FIG. 16 shows a median cross-sectional view of the uterus having a transcervical access port placed in the cervical canal. After transcervical transfer of the baby B to the uterus U, the transcervical access port TCP may be placed in the cervix CER before the cervix is closed. The port admits of drainage and access via the cervical canal.

A transcervical access port may be provided with a cap or plug to provide isolation; the cap or plug may be provided with connectors or ports for fluid lines and other devices.

Prior to transfer of the baby into the uterus, one or more fluid ports may be installed in the uterine wall to pass ventilating fluid into the uterine cavity though the uterine wall. An exemplary uterine wall fluid port is provided by a ventilation head lying flush with the endometrium and which is served through the uterine wall by a ventilating catheter. One or more catheter extension lines may stem from the ventilation head in the manner of an irrigation manifold to distribute fluid over a wider area in the uterine cavity.

FIG. 17 is a side cross-sectional view of rim sections of the top and bottom shells 16, 17 of the absorbable transfer capsule ATC of FIG. 9. Referring to FIG. 17, the inner and outer sliding members 18, 19, which are disposed on the rims of the shells, lock into place in a tongue-and-groove fashion when the capsule halves are joined together and close over the baby.

FIG. 18 is a side cross-sectional view of a variation of the rim sections of the top and bottom shells 16, 17 of the ATC shown in FIGS. 9 and 17, wherein a hole-and-peg system 37, 38 is used to join halves of the ATC.

FIGS. 19 and 20 are respective side perspective and side cross-sectional views of a pinch guard 39 for an ATC. The pinch guard functions to protect the chorionic villi from getting pinched by ATC halves when being closed together over the baby. The pinch guard 39 comprises a flexible strip of absorbable material disposed circumferentially about the inside of the rim of the bottom shell 17 of the ATC, with an amount of material left rising above the rim. In operation, the pinch guard 39 is folded outward to receive the baby and then folded inward before closing the halves together. The inner sliding member 18 of the FIG. 17 embodiment functions as built-in pinch guard to an extent, in contrast to the hole-and-peg system of FIG. 18.

Chorionic and/or amniotic fluid may be withdrawn by syringe to reduce the baby's size when transferring to a tight fitting uterus or through a narrow cervix or small incision.

FIG. 21 is a side cross-sectional view of an absorbable transfer capsule ATC having a reduced diameter 40 in the transverse plane of the cervix to facilitate entry of the capsule through the cervix as it is introduced 41. The baby B is shown oriented in the capsule with the alluvia anterioris oriented toward a landmark 42 in aid of reimplantation in the posterior fundal position.

Echogenic structures may be included in the capsule design to correspond with capsule landmarks to aid the operator when introducing the capsule into the uterus.

The major landmarks of a transfer capsule are superior versus inferior, front (ventral) versus back (dorsal), and anterior versus posterior. When the capsule is in place in the uterine cavity, the internal os of the cervix indicates the inferior side of the capsule and opposite is the superior; the front (ventral) side of the capsule faces the anterior (front) side of the uterus and opposite is the back (dorsal side); and, the median plane of the capsule is generally the same as the mother's. When designed for transcervical introduction, the transverse plane of the capsule is generally that of the cervical canal with respect to the capsule's orientation during introduction. The frontal plane of the capsule is at right angles to the median and transverse planes. When the baby is in the capsule, the anterior of the capsule is the side facing the alluvia anterioris and opposite is the posterior.

For example, referring to FIG. 21, the direction of introduction 41 is the superior and the landmark 42 to which the umbilical cord points is at the anterior. When an ATC has halves, such as the ATC of FIG. 9, the bottom half 17 is the one the operator first puts the baby into, and the top 16 is then used to cover the baby.

To give another example, referring to FIG. 13 in view of FIGS. 10 and 3A, the port where the ventilation catheter CTH emerges from the capsule ATC defines the capsule's inferior, given that the port must be aligned with the internal os of the cervix IOS in order for the catheter CTH to proceed through the cervical canal CCN. Thus, to orient the baby in the capsule so the alluvia anterioris will face the posterior wall of the uterine fundus, in this case the anterior of the capsule will be determined in reference to the inferior.

Referring to FIG. 22, a custom-sized absorbable transfer capsule ATC may have a uterus-fitting outer contour 43 and a baby-fitting inner contour 44. But a difference between outer and inner contours 43, 44 will result in a thick side 45 and a thin side 46. In general it will be correct for the operator to orient the baby with the alluvia anterioris abutting the thin side 46 of the capsule and incorrect to orient the baby with the alluvia anterioris abutting the thick side 45 of the capsule. The thin side 46 is preferred because distancing the chorionic villi of the alluvia anterioris from the endometrium inhibits attachment; however, an exception may arise when the eroding wall of the capsule is designed to provide a supply of beneficial substances for the baby.

A custom-sized ATC as shown in FIG. 22 can be made from a computer-aided design (CAD) file using computer numerical control (CNC) equipment by including the dimensions of the uterus, cervix, and baby. In a subtractive CNC process, a piece of absorbable material 15 is shaped by machining tools such as for cutting and drilling; in an additive CNC process, the absorbable material 15 is deposited by 3D printing tools such as an extruder or microdispenser. Similarly, CNC equipment can make molds from which to form the ATC from the absorbable material 15.

FIG. 23 shows a side cross-sectional view of a wall of an ATC formed by an absorbable material 15 and having a hole 47 disposed therethrough. In general, the ATC may have any number of holes 47 in a predetermined pattern. For example, the holes may form of pores; the holes may form a geodesic pattern of openings to provide structural support for the baby inside while also allowing the chorionic villi to contact the endometrium; or, the holes may form a pattern that favors one side such as the anterior side of the capsule.

FIG. 24 shows a side cross-sectional view of a wall of an ATC formed by an absorbable material 15 and having a hole 47 disposed therethrough, wherein a second absorbable material 15b covers the hole 47 temporarily until such a time as the second material 15b dissolves 48 to leave the hole 47 exposed. To give an example of use, by covering the hole temporarily both the chorionic villi and endometrium will be protected from abrasion while the ATC is introduced.

FIG. 25 shows a side cross-sectional view of a wall of an ATC formed partly by an absorbable material 15 and having at least one region of the wall formed by a second absorbable material 15b, such that the region later dissolves 49 to leave a void 50 in its place. To give an example of use, the region may be scheduled to dissolve 49 so the void 50 exposes the alluvia anterioris to the endometrium at a predetermined time while the remaining absorbable material 15 still covers the alluvia posterioris. See FIG. 1B.

In a loose-fitting uterus, an absorbable spacer, filler, or expanding member such as a swellable hydrogel can be placed in the uterus to bolster the baby or ATC posteriorly to ensure anterior abutment to the endometrium. For example, a catheter or syringe may be used to introduce a hydrogel between the posterior aspect of the gestational sac and the wall of the uterus; the hydrogel may be hydrated in a solution containing nutrients to sustain the tissues of the alluvia posterioris while at the same time bolstering the baby within the uterine cavity. Or for example, an expanding hydrogel member can be affixed to the exterior of the posterior aspect of the ATC.

ATCs may be provided having standardized sizes and shapes. But if an interior of the ATC fits the baby loosely, the operator should ensure that the alluvia anterioris abuts the anterior of the capsule by bolstering the baby in the capsule. This can be accomplished by placing a spacer, filler, or expanding member such as a swellable hydrogel between the posterior aspect of the gestational sac and the capsule wall.

Though FIG. 9 shows an ATC having walls and other features of substantial rigidity, an ATC may also be formed of an absorbable material having varying flexibility, including in the form of a bag, balloon, or coin purse in which to enclose the baby. An ATC may also be formed by wrapping the baby in one or more strips or pieces of an absorbable material. For the smallest of babies, such as those recently implanted, down to the size of the human egg, an ATC may comprise an absorbable material in the form of a straw or cartridge for enclosing the baby. An exemplary straw-type ATC is formed of an absorbable straw having capped ends to hold the baby and a quantity of ventilating fluid. An exemplary cartridge-type ATC is formed using layer-based microfabrication, wherein a vented microcradle is disposed in device layers to hold the baby and a quantity of ventilating fluid according to my incorporated teaching in U.S. Pat. No. 8,292,798, wherein the layers are formed of absorbable materials, and wherein the microcradle includes a cover layer; the cover layer, such as an absorbable tape combined with a biocompatible adhesive, may be added after the baby is in the microcradle, or a non-coring micropipette may be used to insert the baby into the microcradle through one or more layers.

FIG. 26 shows a side perspective view of an embodiment of an absorbable transfer capsule ATC having substantially flexible walls 62 that are made of an absorbable material 15. Whereas the ATC shown in FIG. 9 resembles a plastic Easter egg, the ATC of FIG. 26 resembles a squeeze-type coin purse of the rubbery variety. Referring to FIG. 26, at least one slit 63 is disposed in the capsule walls 62, the slit being sized to admit entry of a baby into the capsule ATC. In operation, the capsule walls 62 are flexible enough that the operator can fold back 64 a portion of the capsule ATC about the slit 63 to place the baby inside 65. The capsule walls 62 retain their elasticity so they close back 66 over the baby once released by the operator so as to leave the baby enclosed inside the capsule ATC. The slit 63 may be taped shut with an absorbable adhesive strip. In general, the capsule ATC may also accommodate catheter lines to ventilate the baby inside. The capsule ATC may also be used without catheter lines, such that beneficial substances are obtained from the capsule walls 62. An outer surface of the capsule may be treated to resist degradation, so that erosive degradation of the capsule ATC is left to proceed from an inner surface, with the chorionic villi gradually invading into the eroding capsule walls.

An ATC may have a self-contained substance delivery system for delivering ventilating fluid or other beneficial substances without need of external connections. In one embodiment, the self-contained delivery system comprises a hydrogel micropump having a swellable hydrogel member that expands at a predetermined rate in a channel housing a reservoir containing the ventilating fluid or other beneficial substances so as to urge the fluid for delivery via the channel or its tributaries. In another embodiment, the self-contained delivery system comprises an osmotic pump for urging fluid contained in a reservoir; depending on the design, fluid in the system may be replenished by means of a syringe.

Conversely, a shrinkable (contracting) hydrogel member provides negative pressure for withdrawing fluid. For example, having been drawn from a source of fresh fluid to ventilate the baby, the fluid may be withdrawn as waste fluid after passing over the baby. For example, the source of fresh fluid may be maternal fluid withdrawn from the uterine cavity. Similarly, osmotic micropumps provide positive or negative fluid pressure depending on a contrast of osmolarity.

Beneficial substances carried by an ATC, e.g., medicine, may be contained in separate capsules or compartments, and also in time-release form.

An ATC or its parts may be coated or embedded with beneficial substances. For example, an outside wall of the ATC may be coated with an inhibitor of degradation so the absorbable material composing the wall erodes from the inside more so than from the outside. Or for example, an outer surface of the ATC may be embedded with medicines for the mother.

Merriam-Webster's Collegiate Dictionary (11$^{th}$ ed., Springfield, Mass.: Merriam-Webster, 2008) defines pabulum (def. 1) as "food; especially, a suspension or solution of nutrients in a state suitable for absorption." As a supplementary source of fluidic ventilation, a nourishing gel, semi-solid, or dissolving solid may be packed into the intervillous space as a type of pabulum when placing the baby in an ATC, in addition to any provision for liquid per se.

Regulators to control a timing and pattern of dissolution of the absorbable materials forming an ATC and related devices may be carried by the ATC or delivered to it in the uterus by a delivery means. An exemplary delivery means is a ventilating catheter.

An absorbable adhesive tape may be wound around an ATC to promote integrity of the enclosure in cases where a tight fitting uterus or cervix may subject the capsule to strong pressures. Double capsules (one capsule placed over another) may also be employed. Capsule walls may be joined with the aid of a biocompatible adhesive or other strengthening features according to the art of joining.

An ATC may be provided with a handle. A variety of handle is detachable immediately after transfer. For example, the ATC may be provided with holes, nubs, or other attachment points adapted to receiving a forceps which serves as a detachable handle. Another variety of handle is left in place for a time in the cervical canal. For example, a hollow handle provides a transcervical access port (TCP). In one example, the TCP is detachable via a link maintained by a proximally controlled microsurgical forceps. In another example, the TCP is made of a material which retains its structural integrity even after a material forming a link with the ATC has degraded; the TCP may be made of an absorbable material which is absorbed later in the cervix or of a material which is at some point withdrawn from the cervix by the operator. An ATC, including capsule halves, may also be handled by suction cups sized for receiving the capsule or its halves. Similarly, an ATC may be provided with removable tabs for handling; the tabs adhere to it by a tape backed by a biocompatible adhesive.

Sutures may be attached to an ATC and the ATC sutured to the uterine cavity.

Walls of an ATC may be provided with a cell scaffold material and hydrated or otherwise embedded with a suspension of cells. For example, a scaffold on the outside of the ATC may contain a culture of the baby's cells to stimulate maternal receptivity; referring to FIG. 6, exemplary cells for this purpose include cytotrophoblastic cells collected at delivery from the trophoblastic shell TS. Similarly, a scaffold on the inside of the ATC may contain a culture of the mother's cells to stimulate the baby's growth; exemplary cells for this purpose include endometrial cells collected in advance of reimplantation.

In normal pregnancy, the baby abuts the endometrium and maternal ventilation circulates in the intervillous space, which serves to dissipate the baby's growing internal heat production. However, in the case of an ATC which covers the baby, the baby is isolated from direct contact with the endometrium as well as from the maternal ventilation. The operator is cautioned that if the ATC does a poor job of dissipating the heat produced by the baby, then the baby will overheat. For this reason, ATCs are preferred that are good conductors of heat.

To address the problem of the baby overheating, which may be monitored with a temperature sensor, the operator may employ steps of increasing a rate of flow or lowering a temperature of fluid circulated in thermal contact with the baby by means of a catheter, lowering the maternal uterine temperature, or lowering the baby's metabolism. See U.S. Pat. No. 9,056,039; claims 1 and 2. Circulating cool fluid in the maternal bladder using a urinary catheter adapted to bidirectional flow may help to lower the uterine temperature.

The design of transfer techniques and devices must take heat dissipation into account at all stages, including during degradation of absorbable materials. Because an ATC, its components (e.g., nourishing gels deposited in the capsule), and degradation products may retard the dissipation of the baby's heat compared to what is normal for pregnancy, it is prudent to include thermal monitoring of the baby inside the ATC and uterus, particularly with new designs, so factors relating to heat dissipation may be appreciated. Moreover, since a distortion of normal metabolism may result in excessive heat production, the design of transfer protocols must take into account an effect on the baby's metabolism so as to guard against overheating.

In the case of a straw- or cartridge-type ATC for a small baby, a micropump, such as a hydrogel or osmotic micropump, in combination with a reservoir to hold fluid, may be included with the ATC to urge fluid past the baby at a predetermined rate to provide fluidic ventilation and heat dissipation. Without heat dissipation the baby may overheat while bathed at uterine temperature. To provide fresh ventilating fluid and heat dissipation, the fluid must be urged past the baby rather than the baby flowing along at the same rate of flow as the fluid; it is also desirable to limit the baby's transit under gravity within the straw- or cartridge-type ATC. For example, a microfabricated structure, filter, mesh, constriction, or adhesive may be employed to limit or impede the baby's transit relative to fluid flow or gravity. Also, the fluid may have a predetermined viscosity to limit the baby's transit under gravity. Since exterior walls of such an ATC may be disposed with holes sized to admit entry of male gametes to fertilize an egg within the ATC after placing the ATC in the uterine cavity, such an ATC may be more generally called a self-contained intrauterine pregnancy capsule (SCIPCAP).

It is contemplated that heat dissipating substances disposed in thermal communication with the baby may help to prevent the baby from overheating, including in time-released form. Exemplary heat dissipating substances include those absorbing a latent heat at a temperature above an optimal ambient temperature (e.g., a protein absorbing a heat of denaturation), and those having endothermic heats of dissolution to absorb heat and lower temperature.

Degradation of absorbable materials forming an ATC should proceed in such a manner as neither to occlude the fluidic patency of the intervillous space nor to inhibit contact between the chorionic villi and the endometrium. Alternating regions of the ATC may be scheduled to degrade sequentially so overall patency and contact are not diminished all at once.

The baby B indicated in FIG. 13 is nearing the end of the seventh week of development CCA, which means the baby is nearing the end of the ninth week of development LNMP. That is to say, in terms of conceptional age, meaning complete chronologic age, the baby B is six weeks old going on seven. An exemplary outer diameter of the absorbable transfer capsule ATC shown in FIG. 13 is on the order of a ping pong ball (40 mm) or up to about 60 mm.

In an exemplary method of delivering a baby, a forceps containing the baby is withdrawn into a bag insufflated with a benign gaseous composition to shield the baby from the open air of the delivery room during transfer to an incubator workstation. The benign gaseous composition is sterile, particle-free, and has an oxygen content not greater than the baby's physiological tolerances. The workstation may form an enclosed workspace to surround an alluvial incubator with the benign gaseous composition having a predetermined temperature and humidity so the baby will be shielded from the open air during transfer to and from the incubator. To prevent infection and contamination, the workstation, including its gaseous supply and other contents, should be sterile and free of foreign particles and debris. Clean room technology or laminar flow hoods may be employed to reduce contamination by particulate matter; for example, a flow hood may be placed above the incubator. An exemplary workspace enclosure comprises a laminar flow hood with a sliding glass door for access to the incubator, wherein airflow in the workspace is substantially limited to vertical upflow proceeding from vents at the base of the workspace to reduce sideflow entry into the workspace when the access door is open, whereby a separate environment is maintained about the incubator in contrast to a surrounding environment maintained for operator comforts. Incubator workstations may be adapted to built-in, benchtop, wheeled, and portable embodiments.

I. Advisory on Teratogenicity

Dorland's defines a teratogen as "any agent or factor that induces or increases the incidence of abnormal prenatal development." See Dorland's Illustrated Medical Dictionary, supra; teratogen. To avoid birth defects, babies should not be exposed to teratogens during gestation.

Susceptibility to teratogens means the risk of birth defects being induced by a teratogenic agent or factor. As shown in FIG. 27, the risk of birth defects being induced varies over the course of pregnancy. The main curve 70 is found in the literature and shows a heightened period of risk that accompanies an early period of organogenesis in which many of the major organs of the formal body are initially formed; the time scale of the graph is in weeks of development (CCA) with the first week of development starting at fertilization.

In an artificial environment such as an incubator, added risks may be present that are not reflected in the main curve 70. To illustrate this problem, in FIG. 27 an auxiliary curve 71 has been figuratively drawn to emphasize that during the first weeks of development babies are highly susceptible to teratogenic factors that are unique to the incubator environment. For example, death may be caused by overheating due to failure to provide adequate heat dissipation at this stage.

Teratogenicity can appear at any time during gestation, with varying severity, and new technologies may create new sources of insult apart from proper chemical and physical treatment of the baby. Another concern is that pregnancy transfer will often take place during a natural peak of teratogenic susceptibility.

In view of FIG. 27, it is necessary to consider the teratogenicity of procedures when scheduling delivery, incubation, and reimplantation. In some instances, this may require such strategies as delaying delivery, or delaying reimplantation by prolonging incubation, until peak periods of teratogenicity have passed. Because the susceptibility to teratogens tends to be organ-specific, when a procedure involves a possible teratogen it may be preferable to schedule the procedure before or after peak periods of sensitivity of the susceptible organs.

The importance of an ultrapure environment in the context of an incubator for babies before implantation is discussed in my incorporated teaching in U.S. Pat. No. 8,292, 798 (column 11, lines 13-27 and 50-56). In view of FIG. 27, the importance is heightened as the patient passes through periods of heightened teratogenic susceptibility.

J. Absorbable Materials

According to the invention, some devices, in particular absorbable transfer capsules, require at least one absorbable material to function. Absorbable materials are especially indicated when the device serves a temporary function, is impractical to remove from the mother's body during pregnancy, and would not be well-tolerated if left in place. Where there is tolerance for material left in the mother, devices may be non-absorbable either in whole or in part; otherwise a fully absorbable device is preferred.

According to the invention, an absorbable transfer capsule (ATC) for an implantable baby comprises at least one absorbable material adapted to an enclosure for the baby and being disposed to at least partial degradation within a predetermined period of time after introduction into a uterine cavity, whereby the baby, having been placed within the capsule and transferred to the uterine cavity, is presented in a manner disposed to implantation or reimplantation.

An exemplary enclosure comprises a capsule structure selected from the group consisting of a hard shell, soft shell, bag, balloon, straw, and cartridge. Absorbable materials forming respective capsule structures are characterized as having: for the hard shell capsule, substantial rigidity; for the soft shell capsule, substantial flexibility; for the bag capsule, substantial flexibility in a thin film; for the balloon capsule, substantial elasticity, typically in a thin film; for the straw capsule, an ability to form a straw; and, for the cartridge capsule, an ability to accept applicable manufacturing steps, such as layer-based microfabrication, micro-molding, or 3D printing.

For devices according to the invention, absorbable materials of exemplary interest include: the natural polymers hyaluronan, glycoprotein, silk protein fibroin, starch, glycogen, and alginate; the synthetic polymer poly(vinyl alcohol); and, natural and synthetic polymers known in the art of biomaterials for their use in absorbable sutures, stents, scaffolds, adhesion barriers, and drug delivery devices. Also of interest are related copolymers, polymer blends, and modified polymers, as well as plasticizers and excipients known in the art of biomaterials.

Hyaluronan also includes hyaluronate and hyaluronic acid. The glycoproteins of interest especially include zona pellucida (ZP) glycoproteins forming the human eggshell and their analogs. The silk protein fibroin of interest is reconstituted and has all traces of silk protein sericin (a possible immunogen) removed. Starch with a high amylopectin content is intuitively preferred due to its similarity with glycogen over amylose. Starch also includes modified starch. Alginate also includes alginic acid. Plasticizers of exemplary interest include glycerol and water.

In likeness to pharmaceutical capsules, which are more generally called drug delivery devices, an absorbable transfer capsule may more generally be called an implantation delivery device. A difference is the primary purpose of an ATC is to deliver an implantable baby to the mother, rather than medicine.

Hard shell and soft shell ATCs find analogy in the art of hard gel and soft gel pharmaceutical capsules. For example, like a pharmaceutical capsule, an ATC dissolves in the body; and, like a pharmaceutical capsule, the ATC can deliver medicine, including by time-release.

Referring to FIG. 9, an exemplary hard shell capsule structure is provided by the Easter egg type ATC, wherein the absorbable material 15 forms rigid top and bottom capsule shells 16, 17 that join together to enclose the baby. Exemplary ranges of rigidity for hard shell ATCs include the rigidities of hard gel pharmaceutical capsules, ping pong balls, hard rubber, and hard foam.

Referring to FIG. 26, an exemplary soft shell capsule structure is provided by the coin purse type ATC, wherein the absorbable material 15 forms flexible capsule walls 62 that fold back to enclose the baby within. Exemplary ranges of rigidity for soft shell ATCs include the rigidities of soft gel pharmaceutical capsules, soft contact lenses, slices of raw squid, soft rubber, and soft sponges.

Combinations of ATC capsule structures, such as hard and soft shell capsules, may be placed one inside the other or formed into composites.

A rigid absorbable material may serve as a backbone for ATC walls having void spaces or sides that are filled or covered with a soft and preferably hydrous absorbable material. Hydrous polymeric materials are generally recognized as having superior biocompatibility because in some cases their water content approximates that of tissues; this is especially true of hydrogels, many of which can imbibe great quantities of water; in contrast, non-hydrous polymeric materials typically lack a hydrophilic chemical structure needed to attract water. But owing to an absorption of water, hydrous materials tend to be relatively soft and flexible, in contrast to non-hydrous materials which by comparison tend to be relatively hard and rigid.

Biocompatibility, mechanical properties, and degradation profile are key characteristics of an absorbable material for medical use. The absorbable material should be sterile and non-toxic, it should not cause inflammation or support the growth of pathogens, and for pregnancy-related use it should be non-teratogenic. By absorbable material in this context is meant the material per se as well as its degradation products. The mechanical properties which an absorbable material is required to possess, such as rigidity or elasticity, depend on its use, such as in hard shell or soft shell capsules. Regarding degradation profile, typically an ATC will be scheduled to degrade within minutes, hours, days, or weeks of being introduced into the uterine cavity.

Generally speaking, the degradation profile of an absorbable material may be nominal, triggered, or delayed by coating. In the case of nominal degradation, the material degrades according to its own merits and in terms of the device it is adapted to. In the case of triggered degradation, the material undergoes accelerated degradation upon application of an enzyme or other agent. In the case of degradation delayed by coating, degradation is blocked via a coated surface until the coating has degraded; other inhibitors or treatments may also block or slow degradation.

The remanence of an absorbable material is the time to degradation or, put another way, the resistance to degradation.

Various treatments can be applied according to the art to articles formed of an absorbable material to provide greater remanence or improved mechanical properties for selected regions or features of the article. For example, Thomas et al. (U.S. Pat. No. 8,262,730) teach methods of bonding or modifying hydrogels using irradiation, whereby a laser irradiating preselected regions of a hydrogel article yields customized cross-linking and intricate reinforcement schemes.

The terms (bio)absorbable, (bio)degradable, (bio)erodible, and (bio)resorbable have not found distinction in the art of absorbable materials, despite various attempts. Related processes include absorption, degradation, erosion, biological elimination, softening, dissolution, breakdown, loss of mass, fragmentation, etc.

In the art of biomaterials, degradation in the body by exposure to water (hydrolytic degradation) is considered to be the most dependable and predicable route to degradation, in contrast to degradation by exposure to enzymes (enzymatic degradation); the reason is water is ubiquitous in the body, unlike enzymes which may be present in unpredictable concentrations. However, predictable concentrations of enzymes and other factors to promote degradation can be supplied to an ATC in utero via a ventilation catheter.

Especially with regard to the alluvia anterioris, erosion of an ATC should not leave a persistent residue which is thermally insulating enough to cause the baby to overheat or which inhibits contact between the chorionic villi and endometrium. Erosion should not restrict the fluidic patency of the intervillous space enough to cause hypoperfusion distress, though in some cases the eroding capsule may be designed to provide for the baby's ventilation as a source of nutriment. Removal of the degradation products may be assisted via catheter or syringe.

When degradation provides nourishment or other beneficial substances for the baby, degradation of an ATC may proceed from the inside out. Otherwise, it is preferable for degradation to proceed from the outside in since the mother's body will be more efficient than the baby's at eliminating the products of degradation; an exception may occur when a catheter within the ATC performs the bulk of removal.

Maintenance of pH implicates both the absorbable material and its degradation products. To maintain a predetermined pH, excipients may be added to buffer or change the pH.

Many absorbable materials are known which, depending on their method of preparation, are biocompatible. However, devices according to the invention require special biocompatibility, such as non-teratogenic biocompatibility. Also noted is that some absorbable materials, such as undegraded kappa-carrageenan and iota-carrageenan, though considered relatively safe when taken via the alimentary canal, may produce complications with parenteral exposure.

Thus special consideration is indicated to ensure absorbable materials are biocompatible for both the baby and mother.

Ultrafiltration and other purification techniques may be employed to promote the purity and biocompatibility of absorbable materials and related compounds according to the art.

A first exemplary absorbable material contains glycoprotein. Glycoprotein forms the natural capsule material of the baby's eggshell. Such glycoprotein or its analog is thus contemplated to be a preferred biocompatible absorbable material for an ATC according to the invention.

A second exemplary absorbable material contains hyaluronan. The literature reports hyaluronan is advantageous in promoting implantation. Hyaluronan is thus contemplated to be a preferred biocompatible absorbable material for an ATC according to the invention.

The following Examples 1 and 2 teach hard shell and soft shell ATC capsule structures, respectively.

Example 1

A water-soluble poly(vinyl alcohol) polymer provided in the form of a thermoplastic filament is extruded by a 3D printer to make the exemplary Easter egg ATC shown in FIG. 9 having the rigidity of a ping pong ball. Owing to water solubility, the nominal degradation rate is within minutes. The degradation may be coating delayed to extend the remanence.

To extend the remanence of the ATC of Example 1, the ATC is coated with reconstituted silk protein fibroin which has been purified to remove all traces of silk protein sericin, the fibroin having a crystallinity prepared by physical temperature-controlled water vapor annealing and which crystallinity is proportional to an enzyme degradation rate of the coating. The remanence is thus extended by minutes, hours, days, or weeks according to the art. See Hu et al., "Regulation of Silk Material Structure by Temperature-Controlled Water Vapor Annealing," Biomacromolecules, Vol. 12, No. 5, 2011, pp. 1686-1696.

Coatings with differential effects on remanence may be applied to different sides or regions of an absorbable material forming an ATC. Holes and other features may also be coated. Additional material may be added over coated materials. The ATC will thus undergo staged or successive degradation based on the differential remanence of its parts.

Example 2

To make the exemplary coin purse ATC shown in FIG. 26 having the flexibility of a soft contact lens, a hyaluronan solution is cross-linked to form a hydrogel solution that is electrospun to form a non-woven fibrous mat which is molded to produce the walls 62 of the ATC having a slit 63 disposed therein. The nominal degradation rate is within hours or days depending on predetermined modifications according to the art.

Thompson teaches an embryo transfer arrangement comprising a balloon formed of a biodegradable film of hyaluronic acid to press the baby between the balloon and a wall of the uterine cavity; the balloon dissolves after a period of 12 to 24 hours to leave the baby implanted in the uterine wall. See U.S. Pat. No. 6,010,448; column 6, lines 10-40; FIGS. 8, 9, 10, and 11. Notably, the baby according to Thompson is outside the balloon, unlike the baby according to the present invention, who is inside a balloon or other ATC capsule structure.

The ATC of Example 2 may be hydrated in a solution containing nutrients and other beneficial substances prior to inserting the baby therein. An example of other beneficial substances includes factors to promote the biomechanical interactions associated with implantation.

Vitrolife Sweden AB (Kungsbacka, Sweden) makes EmbryoGlue®, which is an implantation medium to facilitate implantation after in vitro fertilization. It comprises a bicarbonate buffered medium containing hyaluronan and recombinant human albumin. It also contains nutrients to support the baby from transfer to implantation and factors to promote the biomechanical interactions associated with implantation.

The degradation profile and mechanical properties of polymers can often be altered by cross-linking. But chemicals used in chemical-based cross-linking and radicals generated by irradiation-based cross-linking can be biologically harmful. This is particularly a concern for teratogenicity. Thus the hyaluronan solution of Example 2 is preferably cross-linked without irradiation or chemicals other than water, using cycles at a predetermined pH including freezing, thawing, or dehydration according to the art. See Miyata et al., U.S. Pat. No. 6,387,413. Also noted are processes similar to that of Miyata et al. involving non-degradable poly(vinyl alcohol) hydrogels. See Tanabe et al., U.S. Pat. No. 4,734,097; and, Ku et al., U.S. Pat. No. 5,981,826.

Electrospinning uses an electrical apparatus to produce micro-fibers and nano-fibers from polymer solutions. Cross-linked hyaluronan is viscous, making it difficult to electrospin. To reduce the viscosity, the hyaluronan solution of Example 2 can be partially cross-linked and the resulting mat can be further cross-linked using cycles of freezing, thawing, and dehydration. Um et al. disclose electroblowing to overcome viscosity and assist the electrospinning of hyaluronan. See Um et al., "Electro-Spinning and Electro-Blowing of Hyaluronic Acid," Biomacromolecules, Vol. 5, No. 4, 2004, pp. 1428-1436. An advantage of the fibrous mat over a film of hyaluronan is that the mat has a predetermined porosity which facilitates chemical communication between the mother and baby; it can also serve as a cell scaffold by hydrating it with a suspension of cells.

Tauber et al. disclose an electrospun poly(vinyl alcohol) hydrogel formed into a soft contact lens, which is hydrated with a saline solution and has a high water content and good oxygen permeability (though presumably it is not degradable). See Tauber et al., "Polymer Electrospinning as a Novel Technique to Create a PVA Contact Lens," American Society of Cataract and Refractive Surgery/American Society of Ophthalmic Administrators, ASCRS/ASOA 2008 (April 4-9), Abstract #P-179. Hirt et al. (U.S. Pat. No. 6,710,126) teach degradable poly(vinyl alcohol) hydrogels, though at least some of the chemical modifiers employed may not have the special biocompatibility required by the present invention.

For clarity it is noted that poly(vinyl alcohol) (PVA) is normally water soluble, as in the case of Example 1, and so water-soluble PVA articles rapidly degrade upon exposure to water; in contrast, when PVA is cross-linked, an insoluble three-dimensional polymeric form results called a hydrogel, as in the case of Tauber et al. and Hirt et al. Hydrogels are a type of hydrous polymer capable of absorbing great amounts of water. But unlike water-soluble PVA, which is readily degradable, PVA hydrogels tend not to be degradable; an exception occurs when the PVA structure is chemically modified such that the resultant hydrogel is degradable, as in the case of Hirt et al. In contrast, hydrogels based on hyaluronan are normally degradable, as in the case of Example 2, without chemically modifying the hyaluronan structure.

Degradation of the ATC of Example 2 may be delayed by coating according to the method of Hu et al.

Compounds derived from human or animal sources may introduce pathogens, they may also raise religious or philosophical concerns, in contrast to some plant or fermentation sources. Alginic acid, also known as algin or alginate, is similar to hyaluronan. Both are anionic natural polysaccharides, but alginic acid is a product of brown algae seaweeds and two genera of bacteria, in contrast to hyaluronan which is produced by humans and animals. The literature reports improved electrospinning of various polysaccharides by adding aqueous blends of poly(vinyl alcohol). As a substitute or complement for the electrospun hyaluronan of Example 2, an absorbable material of contemplated interest is sodium alginate which has been electrospun from an aqueous solution blended with poly(vinyl alcohol) to provide a non-woven fibrous mat. See Safi et al., "Study of Electrospinning of Sodium Alginate, Blended Solutions of Sodium Alginate/Poly(Vinyl Alcohol) and Sodium Alginate/Poly(Ethylene Oxide)," Journal of Applied Polymer Science, Vol. 104, No. 5, 2007, pp. 3245-3255; and, Lee et al., "Preparation of Atactic Poly(Vinyl Alcohol)/Sodium Alginate Blend Nanowebs by Electrospinning," Journal of Applied Polymer Science, Vol. 106, No. 2, 2007, pp. 1337-1342.

Alginates normally require addition of divalent metal cations such as calcium ($Ca^{2+}$) for gelation, meaning to achieve the three-dimensional cross-linking needed to form a hydrogel. In contrast, hyaluronan can be cross-linked to form a hydrogel without using chemicals other than water according to such processes as that of Miyata et al. Though the methods of Safi et al. and Lee et al. do not require divalent metal cations to form fibers or mats of alginate blended with poly(vinyl alcohol), the fibers or mats can be further modified by treatment with divalent metal cations to influence their mechanical properties, remanence, or water content. Alginate is a linear copolymer composed of beta-D-mannuronic acid (M) and alpha-L-guluronic acid (G) monomer units. To form a hydrogel, blocks of repeating units of the G monomer are necessary to bind divalent metal cations such as $Ca^{2+}$. Alginates with higher concentrations of G-blocks tend to form gels of greater rigidity. By using bacterial production or bacterial enzymes rather than production by algae, alginates can be prepared for medical grade uses with carefully controlled molecular weights and compositions, which in turn influence their mechanical properties, remanence, and water content. See Hay et al., "Microbial Alginate Production, Modification and its Applications," Microbial Biotechnology, Vol. 6, No. 6, 2013, pp. 637-650; and, Sabra et al., "*Bacterial Alginate: Physiology, Product Quality and Process Aspects*," Applied Microbial Biotechnology, Vol. 56, Nos. 3-4, 2001, pp. 315-325.

For enzymatic degradation, exemplary enzymes to degrade hyaluronates and alginates are hyaluronases and alginate lyases, respectively. But since hyaluronan is found in the human body, adding hyaluronases to speed its degradation may also affect the degradation rates of endogenous hyaluronan. However, this is not an issue when employing absorbable materials that are degraded by enzymes that do not affect endogenous compounds.

As it pertains to hydrogels, syneresis is an extrusion of fluid generally caused by contraction or collapse of the 3D polymer structure forming the hydrogel. Hydrogels exhibiting syneresis may be employed to dispense entrained fluid. For example, increasing the concentration of $Ca^{2+}$ ions beyond a critical point may cause hydrogels based on alginate to undergo syneresis by causing the 3D structure to contract due to increased folding of the polymer backbone.

Another absorbable material of contemplated interest is provided by a film suitable for pharmaceutical capsules which is made of a thermoplastic starch blended with an aqueous solution of poly(vinyl alcohol). See Misic et al., "Novel Starch-Based PVA Thermoplastic Capsules for Hydrophilic Lipid-Based Formulations," Journal of Pharmaceutical Science, Vol. 101, No. 12, 2012, pp. 4516-4528. Noted is that although starch with a high amylopectin content is intuitively preferred from a nutritional standpoint due to its similarity with glycogen over amylose, amylose may contribute superior mechanical properties, including in combination with amylopectin. See Rindlav-Westling et al., "Crystallinity and Morphology in Films of Starch, Amylose and Amylopectin Blends," Biomacromolecules, Vol. 3, No. 1, 2002, pp. 84-91; and, Zhai et al., "Syntheses of PVA/Starch Grafted Hydrogels by Irradiation," Carbohydrate Polymers, Vol. 50, No. 2, 2002, pp. 295-303.

Additional absorbable materials of contemplated interest include polymers and copolymers incorporating monomers, oligomers, or pendant groups in their structure that are released as nutrients or other beneficial substances upon degradation of the material. Exemplary nutrients for the baby include protein sources such as amino acids and perhaps small peptides; carbohydrates such as glucose, pyruvate, lactate, and perhaps the ketones beta-hydroxybutyric acid and acetoacetic acid; and, the essential fatty acids linoleic acid and alpha-linolenic acid and the developmentally essential fatty acid supplements docosahexaenoic acid, eicosapentaenoic acid, and arachidonic acid. Other carbohydrates of interest include 2-deoxyglucose, galactose, mannitol, fructose, ribose, and 2-deoxyribose. See Quraishi et al., "Transport of Sugars Across Human Placental Membranes Measured by Light Scattering," Placenta, Vol. 20, Nos. 2-3, 1999, pp. 167-174. Exemplary other beneficial substances for the baby or mother include antimicrobial, antiinflammatory, antithrombotic, vasoactive, and angiogenic agents.

These and other absorbable materials suitable for use in devices and preparations according to the invention will be appreciated by one skilled in the arts of biomaterials, polymer chemistry, and degradable medical devices.

K. Advisory on the Medical Literature

During the Holocaust 1.0, unethical medical research was conducted on human individuals. The premise was the victims are beings so far interior they have no rights others are bound to respect; they are unwanted; they will be destroyed in any case; and, they are of value to medical research in experiments too risky to perform on others.

During the Holocaust 2.0, the same premise has been applied.

Medical research conducted on human individuals in the past and present versions of the Holocaust share other qualities as well: the research is poor; institutional authorization is obtained; and, ethically designed experiments are precluded as being unnecessary for the unwanted and too dangerous for the rest. In the Holocaust environment, researchers on the bandwagon of unethical practices are paraded as experts, while ethical practices are professionally sidelined along with those who insist on them.

The poor quality of research on human individuals that typifies the Holocaust is not truly a paradox. For unlike chemistry and physics, medicine and biology are poor candidates for happy accidents. Rather, medicine and biology almost invariably require both a subtle mind and careful intelligence. Yet those with subtle minds also appreciate subtleties like the rights and dignity of the person, and those with careful intelligence take care of the people and even the animals and plants in their experiments.

Thus the poor quality of research conducted in the Holocaust is not a paradox; it is a consequence of selection. For in creating an environment of unethical medical research, those with subtle minds and careful intelligence are excluded, while others are put on the academic pedestal in their place. This puts a damper on medical progress, and it explains the nosedive which medical research inevitably takes during the Holocaust.

I mention this here because what I address simply as the "literature" in the remainder of this detailed description regards matter which appears limited in its medical and ethical quality, so as to offer a doubtful foundation for serious work. But at the time of writing, there did not appear to be more fortunate alternatives.

L. Ventilating Fluid

According to the invention, the baby is ventilated with development-specific ventilating fluid compositions, including sequential compositions, which are formulated to emulate or supplement the natural composition of maternal ventilation.

Referring to FIG. 1A, a ventilating fluid VF is a liquid media, which may also include non-liquid matter admixed therein, that circulates over the outside of the baby's egg (pre-hatching) or gestational sac (post-hatching) during gestation to supply the baby with vital substances from the mother and to remove wastes produced by the baby. The ventilating fluid VF also plays an important thermoregulatory role by dissipating the internal heat produced by the baby as a function of the fluid's temperature and rate of flow over the egg or gestational sac, and also as a function of the fluid's thermal conductivity and heat capacity.

The composition of fresh ventilating fluid from the mother is a development-specific combination of hemotroph and histotroph (British: histiotroph). Dorland's defines hemotroph, which is coined from Greek to mean blood-based nutrition, as "the totality of the nutritive substances supplied to the [conceptus] from the maternal blood during gestation"; Dorland's defines histotroph, which is coined from Greek to mean tissue-based nutrition, as "the totality of nutritive substances supplied to the [conceptus] from sources other than the mother's blood." See Dorland's Illustrated Medical Dictionary, supra; hemotroph, histotroph.

In this disclosure, both hemotroph and histotroph fall within the meaning of ventilating fluid according to the invention; additionally, transudates, exudates, and plasma filtrates of maternal blood are regarded as hemotroph along with whole blood itself, and these may include substantial amounts of histotroph. Looked at another way, histotroph gives hemotroph an added content of material.

FIG. 28 provides a rough sketch of the sequential stages of fluidic ventilation experienced by the baby over the course of gestation. In FIG. 28, the first two weeks have an elongated time scale compared to the rest of the graph; the horizontal dashing reflects natural variations in the timing of events as well as clinical uncertainties concerning the onset of stages; the main events are designated as conception, hatching, implantation, and birth. Hatching occurs 5-6 days after fertilization when the baby exits the shell of the human egg. Implantation begins 6-7 days after fertilization (soon after hatching).

Referring to FIG. 28, in this disclosure sequential stages of fluidic ventilation are recognized in order as: the uterine tubal fluid stage S1, the uterine cavity fluid stage S2, the endometrial exudate stage S3, the plasma filtrate stage S4, and the whole blood stage S5. These may be generalized as the transudate stage (which includes the uterine tubal and cavity fluid stages), the plasma filtrate stage (which for general purposes may be interpreted to include the endometrial exudate stage as its crude beginning), and the whole blood stage. The baby is preferably ventilated with fluid compositions designed to emulate or supplement the appropriate stage.

According to Dorland's, a transudate is "a fluid substance which has passed through a membrane or been extruded from the blood as a result of hydrodynamic forces. A transudate, in contrast to an exudate, is characterized by high fluidity and a low content of protein, cells, or of solid materials derived from cells." See Dorland's Illustrated Medical Dictionary, supra; transudate. Starting at conception, the baby is ventilated by uterine tubal fluid, which is a transudate of maternal blood having histotrophic contributions from the mucosal lining of the uterine tube. Upon entering the uterine cavity before implantation, the baby is ventilated by uterine cavity fluid, which is a transudate of maternal blood having histotrophic contributions from the endometrium. The transudate stage covers life before implantation.

According to Dorland's, an exudate is "material, such as fluid, cells, or cellular debris, which has escaped from blood vessels and has been deposited in tissues or on tissue surfaces, usually as a result of inflammation. An exudate, in contrast to a transudate, is characterized by a high content of protein, cells, or solid materials derived from cells." See Dorland's Illustrated Medical Dictionary, supra; exudate. Upon implantation, the baby is ventilated briefly by pooling exudates of maternal blood as endometrial arterioles (small arteries in the endometrium) are ruptured by the baby penetrating the endometrium.

From implantation to birth, the endometrial arterioles, known in particular as the endometrial spiral arteries, supply the source of fresh hemotroph. The hemotroph circulates in contact with the gestational sac to ventilate the baby and then exits through endometrial venules (small veins in the endometrium). Upon implantation, cells/tissues of the gestational sac abutting the endometrium modify the distal portions of the spiral arteries to enable the baby to control a flow-release of hemotroph for the remainder of pregnancy. It was previously assumed the flow consisted of whole blood during the whole period from implantation to birth. But the more recent literature reports finding the flow is limited to a plasma filtrate until around the time an early period of organogenesis is complete, after which whole blood is allowed to circulate in the intervillous space.

According to Dorland's, plasma is "the fluid portion of the blood in which the particulate components are suspended." See Dorland's Illustrated Medical Dictionary, supra; plasma (def. 1). In the context of this disclosure, a plasma filtrate means blood with the red blood cells (erythrocytes) filtered out, which are the main oxygen carriers of blood. The literature reports the filtering is accomplished by partial occlusion of the spiral arteries by the baby's cells/tissues which regulate the flow of hemotroph. The literature hypothesizes that a low oxygen tension maintained in the intervillous space by the plasma filtrate compared to by whole blood protects the baby's newly forming internal organs from oxidative stress during the early period of organogenesis. Note that the endometrial exudate stage may be viewed as an initial state of imperfectly regulated flow at the start of the plasma filtrate stage.

The literature reports that after 12 weeks gestation, or perhaps as early as 10-12 weeks gestation, the baby's cells/tissues regulating the spiral arteries cause them to open up to let whole blood flow from the mother into the intervillous space for the remainder of pregnancy. This is interpreted here as development weeks 10-12 LNMP, corresponding to development weeks 8-10 CCA, which covers the time starting when the baby turns seven weeks old CCA and ending when the baby turns ten weeks old CCA.

The literature reports that transitioning from the plasma filtrate to whole maternal blood causes the oxygen tension of the fluid circulating in the intervillous space to rise from less than 20 mm Hg to greater than 50 mm Hg. The literature hypothesizes the baby relies in large part on anaerobic metabolism until the whole blood stage, though the corresponding mechanisms of cellular respiration remain unknown. Anaerobic respiration does not rely on oxygen for energy metabolism, unlike the more familiar aerobic respiration. Inferences made from the literature concerning anaerobic metabolism are: pyruvate and lactate play a role; pyruvate is essential; at least in the mouse, increased lactate increases pyruvate metabolism, except during the first few days of life when it inhibits pyruvate metabolism; and, aerobic metabolism of glucose may serve to complement anaerobic metabolism.

During the plasma filtrate stage, the literature hypothesizes the baby relies heavily on histotroph in the form of rich glandular secretions from the endometrium. In fluid sampled from the intervillous space during the first trimester LNMP, the literature reports finding glycogen (a storage form of glucose) and two glycoproteins (glycodelin A and the mucin MUC-1). The literature speculates glycodelin A and the mucin MUC-1 serve as endometrial sources of histotrophic nutrition via phagocytic uptake in a layer called the syncytiotrophoblast which lines the intervillous space, with subsequent breakdown to provide a source of amino acids for the baby.

Noted aside is that the plasma filtrate is like a transudate in that it is extruded from the blood. But it differs in that more particulate components are passed from the blood than when forming the uterine tubal and cavity fluid transudates; it also differs in that the uterine tubal and cavity fluid transudates are extruded through maternal tissues, unlike the plasma filtrate which is extruded past the baby's cells/tissues which partially occlude the spiral arteries. So, in a sense, the plasma filtrate stage may either be considered separately or as the last of three transudate stages, the first two being the luminal transudate stages, consisting of the uterine tubal and cavity fluid stages, and the last being the endometrial transudate stage; here luminal refers to the lumens of the uterine tubes and cavity. At any rate, in this disclosure the plasma filtrate stage is considered separately from the (luminal) transudate stages.

Ventilating fluid may be obtained in whole or in part from maternal or donor sources or from artificial preparations. For example, ventilating fluid may be prepared for the uterine tubal and cavity fluid stages from modified physiological solutions, for the plasma filtrate stage from maternal or donor blood plasma, and for the whole blood stage from maternal or donor whole blood.

Preparations of whole blood and blood plasma include those with coagulation factors removed and those with anticoagulation factors added. Blood plasma with the coagulation factors removed is more specifically termed blood serum, though here in this disclosure it is referred to simply as a type of blood plasma preparation.

Surface coatings can be applied to devices exposed to blood or blood plasma to reduce clotting according to the art of hematology.

Generally speaking, maternal ventilation provides the baby with water, salts, oxygen, and antioxidants in a pH buffered and osmotically balanced medium containing albumin; it provides carbohydrates, peptides, amino acids, glycoproteins, lipids, vitamins, and minerals as nutrients for the baby; it removes carbon dioxide, urea, uric acid, creatinine, and bilirubin as wastes produced by the baby; it exposes the baby to antibodies produced by the mother; and, it exposes the baby and mother to each other's hormones, cytokines, and antigens. It also plays a critical thermoregulatory role by maintaining the baby's temperature, both by virtue of the temperature of maternal ventilation at ~37° C. as well as by virtue of its rate of flow over the baby's egg or gestational sac and which flow dissipates the internal heat produced by the baby's metabolism.

In view of the literature findings, it will be tentatively appreciated that preparations of ventilating fluid for the plasma filtrate and whole blood stages may include development-specific and predetermined levels of oxygen, glucose, pyruvate, lactate, glycogen, glycodelin A, and the mucin MUC-1. Pregnancy studies including the sampling and analyzing of the content and change of content over the course of gestation of matter circulating in the intervillous space in utero will provide benchmarks according to the art for determining a preferred content of such preparations for use with the invention.

Studies of maternal uterine tubal and cavity fluid will provide benchmarks for preparing ventilating fluid for the transudate stages. Note that the uterine tubal fluid stage may be subdivided into additional stages (e.g., infundibular, ampullar, isthmic) having sequential compositions of ventilating fluid. As is noted in U.S. Pat. No. 8,292,798 (column 81, lines 42-62), it is suspected that incompetent thermoregulation practices led the prior art to misplaced determinations of optimal fluid media for incubation before implantation (giving the example that a formula that suppresses metabolism may appear superior in an environment of poor heat dissipation by reducing endogenous heat production, but not so in an environment of adequate heat dissipation).

The exchange of matter and heat between the baby and mother during pregnancy is limited to exchange via the ventilating fluid and via those tissues of the gestational sac in direct contact with the mother.

The mother and baby are exposed to substances they produce or share during pregnancy, including in aid of such processes as hatching, implantation, maternal receptivity, the maintenance of pregnancy, and birth. In aid of such processes, the mother and baby may be purposefully exposed to such substances or their analogs by planned action and in predetermined amounts.

In general, a vehicle for delivering such beneficial substances is provided by fluid and especially the ventilating fluid. For example, venous (waste) fluid obtained from ventilating the baby in an incubator may be circulated via a catheter placed in the uterine cavity in advance of transferring the baby for (re)implantation; advantageously, substances produced by the baby to promote maternal receptivity will be contained in the fluid, which may be further supplemented according to the art. Alternatively, fluid may be specially prepared for this purpose.

In another example, the endometrium may be exposed to such substances after transferring the baby for reimplantation by way of an intrauterine ventilator, whereby the ventilating fluid is circulated against both the gestational sac and the endometrium. The venous fluid, which is fluid having passed over the baby's gestational sac to be removed as waste, will contain substances produced by the baby that promote maternal receptivity upon contact with the endometrium. The ventilating fluid may be further supplemented for this purpose according to the art.

To preparations of ventilating fluid may be added substances to promote the health of the baby and mother as well as to maintain fluid quality. Examples include buffers (to maintain pH), preservatives (e.g., anticoagulants), stabilizers (e.g., to protect proteins during pasteurization), binders (e.g., neutralizers for wastes and toxins), regulatory substances (e.g., cytokines, hormones, and growth factors), and medicines (e.g., antibiotics and antimicrobial agents).

To such preparations may also be added substances to modify, dissolve, maintain, actuate, signal, or calibrate materials or devices in contact with the fluid. Examples include catalysts to soften or dissolve an absorbable material forming an ATC, inhibitors to prevent degradation of the material, solutes to actuate an osmotic pump contained by an ATC, and reference compounds to signal or calibrate a sensor carried by an ATC.

Depending on composition, preparations of ventilating fluid may also be pasteurized, homogenized, and filtered.

Great concern for teratogenicity arises when preparing, storing, and handling ventilating fluid. For example, polyvinyl chloride (PVC) plastics made with a phthalate plasticizer such as bis(2-ethylhexyl) phthalate are commonly used for blood bags, medical tubing, and catheters. But exposure to phthalates leaching out of the plastics is harmful to development. Accordingly, if teratogen-free plastics are not available, then it is preferable to make as much use as possible of bottles, tubing, connectors, valves, and enclosures made of glass to provide an ultrapure environment for the baby. Great care must be taken not to introduce teratogens when processing or delivering the ventilating fluid. For an exemplary ultrapure incubator environment, see U.S. Pat. No. 8,292,798 (column 11, lines 13-27 and 50-56).

Although amounts of substances comprising maternal ventilation serve as a benchmark for optimal amounts, lowering or raising the amounts may be indicated to slow or speed the baby's growth as needed. For example, in some cases it may be advantageous to slow the baby's growth in the incubator (e.g., by lowering nutriment amounts) to limit the size of the baby to make transfer easier when a longer incubation time is needed to prepare the mother or baby for reimplantation.

Though it is contemplated that supplying oxygen to the baby has a diminished importance during those periods of development in which the baby relies largely on anaerobic metabolism, nonetheless the importance of removing wastes from the baby remains critical as always to prevent toxic buildup. It is further contemplated that an added importance of providing nutriment to the baby during these periods is that it is relied upon not only for nourishment but also to sustain anaerobic metabolism.

Ventilating fluid can be supplied in a variety of different ventilation schemes. In a disposable scheme, ventilating fluid is prepared with a predetermined content and then disposed of once the content is no longer suitable for use due to depletion of vital substances or buildup of wastes. In the disposable scheme, the ventilating fluid may be passed over the gestational sac once or recirculated multiple times; either way it must be discarded and replaced with new fluid once the old fluid is spent.

In a refreshable scheme, ventilating fluid is recirculated multiple times during which its content is maintained at predetermined levels. According to the refreshable scheme, waste buildup is removed from the ventilating fluid by dialysis and vital substances are continually replenished. Sensors (e.g., for temperature, pH, oxygen, urea, glucose, etc.) may be employed to monitor parameters of a quality or content of the ventilating fluid and feedback controls may be employed to maintain the parameters at predetermined levels, including based on indications of health status.

The disposable scheme may further be called a one-pass or multi-pass scheme depending on whether the fluid is passed over the gestational sac once or recirculated multiple times. But since the refreshable scheme is invariably recirculating it may simply be called the recirculating scheme (versus the multi-pass disposable scheme).

A fluidic ventilator for use in the recirculating scheme may include such exemplary devices as an oxygenator for oxygenating the ventilating fluid and removing carbon dioxide (e.g., membrane oxygenator), a pump to urge the ventilating fluid (e.g., peristaltic pump (e.g., roller pump), centrifugal pump, or micropump), media reservoirs to maintain the ventilating fluid (e.g., for sequential media, media additives, pH buffers, or medicine), media sensors and computer control units (to sense and moderate a condition of the ventilating fluid), a dialysis unit (to remove wastes from the ventilating fluid and also to maintain, e.g., by ultrafiltration, the balance of water content and solute concentrations), and fluid warmers to maintain the ventilating fluid and other media within predetermined temperature ranges (e.g., IV fluid warmer or temperature bath).

In both the one-pass and recirculating schemes, the content and qualities of venous (waste) samples of ventilating fluid may be detected by continuous monitoring or periodic sampling, including with differential comparison to arterial (fresh) samples. Such will provide indications of health status based on detected amounts of metabolites, biological markers, and expressed factors (e.g., hormones, growth factors, and cytokines); such will also provide feedback for adjusting incubation parameters, including the content and qualities of the ventilating fluid. Such may be further interpreted in view of the baby's vitals signs, such as growth, temperature, heart rate, and electrophysiological activity.

As the baby's oxygen needs increase, the amount of oxygen supplied by the ventilating fluid should also increase. In view of literature values for the oxygen tensions of fluid circulating in the intervillous space over the course of pregnancy, relatively low oxygen tensions may be accorded to development prior to the whole blood stage and relatively high oxygen tensions to the whole blood stage, with some transition in between. Physiological gases (i.e., oxygen, carbon dioxide, and nitrogen) should be maintained in the ventilating fluid at predetermined levels in accord with the baby's development-specific needs. In the disposable scheme, oxygen levels may be pre-established with a bubble oxygenator. In the refreshable scheme, oxygen and carbon dioxide levels may be maintained with an oxygenator, including with feedback from sensors to detect gas levels. The baby's blood and tissue gases may also be monitored.

FIG. 4 shows an exemplary one-pass disposable ventilation scheme. Referring to FIG. 4, the baby B, who is not yet seven weeks old CCA, is shown being ventilated in the incubator 1 with ventilating fluid VF comprising a blood plasma preparation having a low oxygen tension, which is not recirculated after exiting the fluid exit port 10.

Not only does a content of the liquid media used for fluidic ventilation change over the course of gestation, but a rate of flow of the liquid media also changes. Increase in the rate of flow is important not only to transfer a greater amount of substances to support the baby's growing needs, but also to increase heat transfer due to the increased production of heat associated with the baby's growing metabolism. Ventilation is optimal when it proceeds with optimal transfer of matter and heat.

To provide optimal fluidic ventilation, the operator is taught: to fluidically ventilate the baby's gestational sac with development-specific liquid media by means of a fluidic ventilator; to emphasize fluidic ventilation of the alluvia anterioris, which is the anterior aspect of the gestational sac; to regulate the dissipation of the baby's internal heat by adjusting fluid flow rates and fluid temperature in reference to feedback from patient temperature; to ensure abutment of the alluvia anterioris to the endometrium in a preferred orientation within the uterine cavity, such as the posterior fundal position; and, to maintain the fluidic patency of the intervillous space by means of a chorionic spacer.

In view of FIGS. 1A-1B, given the differential importance of ventilating the alluvia anterioris AA versus the alluvia posterioris AP, differential ventilation may be applied to these two different aspects of the gestational sac. For example, ventilating fluid preparations of limited content may be applied to the posterior aspect of the gestational sac to conserve costs, while reserving preparations of plenary content for the anterior aspect. This makes increasing sense as the difference increases with development.

The arts of cardiovascular perfusion and organ transplantation are related to the invention. Further modification of the ventilating fluid will be appreciated by one skilled in the arts of hematology, culture media preparation, cardiovascular perfusion, dialysis, organ transplantation, biochemistry, endocrinology, metabolism, immunology, and nutrition.

M. Miscellaneous Ventilation Issues

FIG. 29 is a graph of intervillous oxygen tension measurements adapted from Tuuli et al., "Review: Oxygen and Trophoblast Biology—A Source of Controversy," Placenta, Vol. 32, Suppl. 2, 2011, pp. S109-S118; FIG. 1, p. S110. The measurements relate to the oxygen tension of the intervillous space during pregnancy as a function of gestational age. The oxygen tension measurements ($pO_2$) are depicted as means, minimum, and maximum values in the intervillous space over different gestational age ranges from five in utero studies. The range of ages covered by available data is sparse, accounting for less than half of gestation, and the amount of data available for covered regions is scant, especially in early gestation.

Referring to FIG. 29, the literature reports a rise in the oxygen tension of the intervillous space at a gestational age of around 12 weeks LNMP (10 weeks CCA). The literature theorizes the rise corresponds to a transition between the plasma filtrate and whole blood stages. Maximum values at the peak of the rise are in the 70-75 mm Hg range. But by the end of pregnancy, oxygen tension has diminished considerably. The latter effect may be due to the baby having a heavier draw on available oxygen near term compared to at the onset of the whole blood stage.

For decades the prior art has engaged in what is termed in vitro perfusion of the human placenta. See Challier et al., "In Vitro Perfusion of Human Placenta. V. Oxygen Consumption," American Journal of Obstetrics and Gynecology, Vol. 126, No. 2, 1976, pp. 261-265. According to this practice, after cutting the umbilical cord and delivering the afterbirth, the placenta is preserved and perfused in vitro. At term, the placenta is partitioned into 15-20 cotyledons (10-40 is a broader estimate). Typically, a single cotyledon is selected for perfusion with an oxygenated perfusate. Perfusate values such as oxygen tension are detected to shed light on metabolism in the placenta, for example by probing or sampling the perfusate in the intervillous space or as outflow.

Associated with each cotyledon is at least one highly branched chorionic villus that stands like a tree on the chorionic plate, including as many as 1-5 trees; in this disclosure this is called a villus tree, also known as a villous tree. At the base of the tree, blood vessels in the villus tree join with those in the chorionic plate, which in turn join with those of the umbilical cord. In dual perfusion experiments, one circuit circulates a first perfusate in the intervillous space, while a separate circuit circulates a second perfusate in vessels of an underlying region of the chorionic plate.

Challier et al. experimented with different perfusates, including whole blood, a modified Earle's buffered salt solution to which red blood cells were added, and a modified Earle's buffered salt solution without red blood cells. Based on a variety of experiments, they observed "the rate of release of $O_2$ from hemoglobin and diffusion from the red blood cell might have limited the available $O_2$" in the surrounding plasma/solution. See Challier et al., supra; p. 265, column 1. In other words, due to rapid consumption of oxygen by the placenta at term, the plasma is not in a state of equilibrium with the oxygen content of its red blood cells. Thus it appears the baby's active uptake of oxygen is able to exceed the kinetics of oxygen release and diffusion from maternal red blood cells.

Here the observation of Challier et al. is taken to imply oxygen tension readings may be higher by an artifactual amount when oxygen is being rapidly consumed and samples are allowed to equilibrate before readings are taken. For example, Quilligan et al. found a mean oxygen tension of 42.0 mm Hg in the intervillous space within several weeks of term delivery. See Quilligan et al., "Oxygen Tension in the Intervillous Space," American Journal of Obstetrics and Gynecology, Vol. 88, No. 5, 1964, pp. 572-

577. But since their readings were obtained from samples collected by syringe, which allows the samples time to equilibrate before measurement, then in view of Challier et al. the true oxygen tension in the intervillous space was likely lower than reported.

It is noted for clarity that the oxygen tension of the blood is a measure of the immediate oxygen content of the plasma portion of the blood. So with the baby rapidly pulling oxygen out of the plasma portion of whole maternal blood, the tension in the plasma can drop even though ample amounts of oxygen remain stored in red blood cells to eventually replenish the plasma with oxygen. Put another way, the kinetics of consumption can exceed the kinetics of replenishment.

Thus, when red blood cells are involved, readings obtained without a lag time, e.g., using an oxygen sensor probe inserted into the intervillous space, offer direct readings of oxygen tension; otherwise, the measured tension may have to be lowered by an estimated amount to determine the true tension of oxygen as it is present in the intervillous space. In any case, the true oxygen tension is the preferred quantity to consider as a parameter of incubation.

However, when red blood cells are not involved, equilibration time is not an issue. In such cases, the choice of technology and method may be varied. For example, when determining benchmark values for oxygen tension in absence of red blood cells, a bench-top blood gas analyzer relying on collected samples may offer more accuracy and precision than an oxygen sensor probe taking direct readings in the intervillous space. See Hwang et al., "Evaluation of the Paratrend Multi-Analyte Sensor for Potential Utilization in Long-Duration Automated Cell Culture Monitoring," Biomedical Microdevices, Vol. 6, No. 3, 2004, pp. 241-249.

Normal arterial oxygen tension for the mother's blood ranges from 80-100 mm Hg. Red blood cells serve as oxygen reservoirs to maintain the oxygen tension in the surrounding plasma despite consumption of oxygen by the tissues. But with the red blood cells filtered out, the oxygen tension of the plasma filtrate will decline as oxygen is consumed by the tissues.

During the plasma filtrate stage, some consumption of oxygen will occur in the distal portion of the spiral arteries as the plasma filtrate emerges. But initially the oxygen tension of the filtrate is expected to be that of the whole blood from which it is extruded. Once in the intervillous space, the oxygen tension in the plasma filtrate will continue to decline, reaching an average value by mixing. The oxygen-depleted plasma then returns to the mother via her endometrial venules.

Referring to FIG. 4, for clarity it is noted that the issue of maintaining a low oxygen tension during the plasma filtrate stage does not literally regard the oxygen tension of the ventilating fluid VF in the fluid reservoir 4 per se. Instead, it literally regards the oxygen tension in the intervillous space, with emphasis on the alluvia anterioris.

For a given rate of oxygen uptake, the longer the time a given unit of plasma filtrate spends in contact with the tissues of the intervillous space, the greater the depletion of its oxygen content, and vice versa. Longer times and, hence, greater depletion are provided by slower flow rates, and vice versa. For a given flow rate, shorter times are provided by shorter fluid path lengths taken between arterial and venous ports in the intervillous space, and vice versa.

As a note on terminology, with respect to oxygen tension, some distinction is needed among the terms physiologic, hypoxic, normoxic, hyperoxic, and superoxic. Hypoxia, normoxia, hyperoxia, and superoxia refer to hypoxic, normoxic, hyperoxic, and superoxic states, respectively. Physiologic oxygen tension refers to normal, non-pathological oxygen tension, also called normoxic tension, from normmeaning normal. Hypoxic means below normal oxygen tension, and hyperoxic means above normal oxygen tension. Superoxic means hyperoxic, but carries with it an added connotation of being high enough above normal oxygen tension to threaten pathological conditions.

The literature reports the baby develops in a relative state of "hypoxia" during the plasma filtrate stage; but this is misleading. It is clearer to say the baby develops in conditions which are "normoxic" for the baby but which are hypoxic with respect to the mother. This distinction is important when dealing with incubation parameters of oxygen tension, which are monitored with respect to physiologic values for the baby. In this disclosure, the prefixes matern(o)- and concept(o)- are used in relation to the mother and baby, respectively; to give an example of use, in the plasma filtrate stage the baby develops in a state of conceptonormoxia which is maternohypoxic.

As an added note on terminology, in this disclosure conceptal and conceptally are used in reference to the conceptus, in likeness to maternal and maternally; to give an example of use, in the plasma filtrate stage the baby develops in a state of conceptal normoxia and maternal hypoxia. But in reference to conception, conceptional is preferred. Concept is the direct anglicized version of the Latin conceptus, but in this disclosure conceptant is recommended instead, in likeness to infant, and the associated period of life is conceptancy.

A number of advantages are contemplated to employing a ventilating fluid formulated on the basis of a physiological buffered salt solution, and particularly without red blood cells added. Red blood cells render the fluid opaque and are subject to breakdown (hemolysis). Whole blood and blood plasma contain coagulation factors that will clog or befoul devices unless suppressed or removed; prolonged use of heparin to suppress coagulation may have adverse affects. Compared to physiologic solutions, the viscosity of blood and blood plasma may be higher than optimal for some microfluidic applications. There is a limit to how much blood or blood plasma can be collected from the mother without burdening her system, especially after surgery. Donor blood and blood plasma present risks of pathogens and incompatibility. Blood products require special handling, preparation, and preservation techniques.

But in experiments with the in vitro perfusion of the human placenta, when dealing with the placenta's high demand for oxygen at or near term, the prior art has found it difficult to supply physiological amounts of oxygen in the intervillous space using buffered salt solutions at a normoxic oxygen tension in absence of red blood cells. Instead, when omitting an addition of red blood cells, the prior art has employed buffered salt solutions having a superoxic oxygen tension to satisfy the oxygen demands while maintaining flow rates that are not so high as to threaten mechanical damage to the chorionic villi.

In contrast to the prior art, Soydemir et al. have adapted the in vitro perfusion of the human placenta to perfusates having physiologic oxygen tensions associated with normal pregnancy. See Soydemir et al., "Adapting In Vitro Dual Perfusion of the Human Placenta to Soluble Oxygen Tensions Associated with Normal and Pre-Eclamptic Pregnancy," Laboratory Investigation, Vol. 91, No. 2, 2011, pp. 181-189. Although they are not concerned with providing life support for a baby (the baby has been delivered and the umbilical cord cut), they disclose (p. 181, column 2) that an advantage of perfusing the placenta with perfusates having a normoxic tension is that "not only may superoxia be damaging to the organ, but also there is now a considerable body of evidence that oxygen can regulate many placental functions . . . " To perfuse a cotyledon with a buffered salt solution lacking red blood cells and having a normoxic oxygen tension yet which satisfies oxygen demands while maintaining flow rates that are not so high as to threaten mechanical damage to the chorionic villi, Soydemir et al. disclose a modification of the prior art by increasing to 22 a number of arterial cannulae (catheters) placed in the intervillous space and staggering their vertical depth, wherein the distal end of each cannula is cut at an angle. Ibid.; FIG. 1, pp. 182-183.

FIG. 30 is a side cross-sectional view of a cotyledon being perfused according to the art of Soydemir et al., with only two of their 22 cannulae being shown. See Soydemir et al., supra; FIG. 1(b), pp. 182-183. The baby has already been delivered and the umbilical cord has been cut. The purpose of their experimental setup is to investigate the physiology and metabolism of the placenta at or near term.

As shown in FIG. 30, a cotyledon is lobular fluidic compartment forming an incomplete partition around a chorionic villus tree; the tree is highly branched, contains numerous villi, and stems from the chorionic plate; though the tree is depicted here with merely a few branches, in actuality the branching forms a swamp of numerous fiber-like strands in the fluid of the intervillous space; other trees of various sizes may be contained by the same cotyledon. The partition formed by the cotyledon is bounded superiorly and circumferentially by the trophoblastic shell, forming a dome at the top and a septum SEP at the sides; but the partition is incomplete because the septum SEP does not extend all the way down to the chorionic plate. Villus trees may be anchored superiorly to the dome as shown, which is typical for at least one tree in the cotyledon, or laterally to the septum SEP, or unanchored.

The literature reports the likely precursors of future septa are observed within a few weeks after the start of implantation. Although the mechanism by which the septa form to produce cotyledons remains speculative, the cotyledons will have reached their definitive form within a month or so after the onset of the whole blood stage. The presumption is the cotyledons organize fluid flow. Yet the literature reports true septa are not found in abdominal pregnancies. Thus they are likely not essential and may not be able to form on their own outside the uterus.

Referring to FIG. 30, according to the art of Soydemir et al. only arterial cannulae 72-A are employed in the intervillous space; no venous cannulae are employed in the intervillous space. In operation, an oxygenated perfusate is urged from a roller pump 73 and emerges from the tips of the arterial cannulae 72-A into the intervillous space, where it circulates until exiting through venous ports 74-V remaining as remnants of maternal venules at the top of the cotyledon. Although Soydemir et al. disclose a total of 22 arterial cannulae for perfusing the intervillous space of a single cotyledon, only two are shown in FIG. 30. The cannulae 72-A are inserted into the intervillous space from the top side of the cotyledon to alternate depths of approximately 1 cm and 2 cm beneath the trophoblastic shell, as shown. The cannulae are made of polyethylene having innner and outer diameters of 0.58 mm and 0.96 mm, respectively. A single arterial port is provided by the tip of each cannula 72-A, which is cut at a diagonal angle; the cannulae are otherwise solid-walled along the rest of their lengths.

As will be appreciated in view of FIG. 30, a limitation of the art of Soydemir et al. is that a fluid path taken by the perfusate in traveling from arterial to venous ports in the intervillous space is not shortened in length by increasing the number of arterial cannulae. For example, the path taken by the perfusate emerging from the longer of the two cannulae shown will be on the order of over 2 cm in length as the fluid emerges from the tip of the cannula 72-A, which serves as the arterial port, and travels the intervillous space until exiting the venous port 74-V at the top of the cotyledon; also noted is that the path taken by the perfusate emerging from the shorter of the cannulae may be even longer since, as shown, first it will travel downward before being directed back up and out.

The importance of fluid path length will be appreciated by analogy to a piece of photographic paper traveling on a conveyor belt in a lighted area from first to second darkrooms. For a given speed of the conveyor belt, the longer the distance between the darkrooms, the greater the exposure of the paper. In this analogy, exposure of the paper is analogous to oxygen being consumed from the perfusate by exposure to the chorionic villi; the first and second darkrooms are analogous to the arterial and venous ports provided respectively by the tips of the cannulae 72-A and the remnants of maternal venules 74-V; the perfusate flow rate is analogous to the speed of the conveyor belt; and, the length of the conveyor belt is analogous to the fluid path length traveled by the perfusate in going from arterial to venous ports. Thus, to limit oxygen depletion in the perfusate at a given flow rate, the fluid path length should be kept short.

However, as will be appreciated in view of FIG. 30, a limitation of the art of Soydemir et al. is that adding additional cannulae does not shorten the fluid path length. The root of the problem is their art does not provide venous ports within the intervillous space; instead, they rely exclusively on venous ports 74-V provided in the dome wall of the cotyledon.

Noted is that in this disclosure the term ventilating fluid is used distinctly from the term perfusate. There are a couple of reasons for this. One is that not all perfusates are ventilating; to be ventilating, the perfusate must be capable of satisfying the baby's needs of fluidic ventilation. The other is that not all ventilating fluid is a perfusate per se; for example, the ventilating fluid may also take the form of a semi-solid or gel as opposed to a liquid per se.

As shown in an exemplary FIG. 31, the invention overcomes the limitations of the prior art and the art of Soydemir et al. by providing both arterial and venous ports within the intervillous space to establish a short fluid path length between arterial and venous ports. Advantageously, the short fluid path length limits an amount of oxygen depletion experienced by a ventilating fluid as it travels from arterial to venous ports. Thus, by limiting the amount oxygen depletion experienced by the fluid as it travels the intervillous space, the ventilating fluid can be formulated on the basis of a physiological buffered salt solution without adding red blood cells.

Recalling the analogy to the photographic paper, inasmuch as fluid path length is shorter according to the present invention, then for a given flow rate there will be less depletion of oxygen in the fluid as it travels between arterial and venous ports according to the invention than according to the art of Soydemir et al. Advantageously, less depletion means a predetermined oxygen tension range can be maintained over the course of exposure even when employing a fluid with limited oxygen content, such as a buffered salt solution without red blood cells. Thus the inventive approach allows more flexibility in formulating the fluid than the art of Soydemir et al.

Similarly, for equal depletion of oxygen in the fluid, which is likened to equal light exposure in the photographic paper analogy, the corresponding flow rate will be slower according to the invention due to a shorter fluid path length than according to the art of Soydemir et al., even though the amount of exposure (oxygen depletion) is the same. Advantageously, slower flow rates reduce mechanical damage to the chorionic villi. Thus the inventive approach makes it easier to limit intervillous flow rates than the art of Soydemir et al.

Recalling the photographic paper analogy, for clarity it is noted that the approach of Soydemir et al. is like placing 22 conveyor belts side by side. When using only a few arterial cannulae (few conveyor belts), they found the oxygen concentration measured between cannulae (between conveyor belts) is very low. See Soydemir et al., supra; p. 187, column 1. Adding more cannulae increases the lateral concentration between conveyor belts; put another way, it reduces the gradient of lateral depletion by concentrating the number of conveyor belts. But to reduce exposure (oxygen depletion) along each conveyor belt, it is necessary to reduce exposure time. To reduce exposure time, either the flow rate can be increased, or the length of the conveyor belt (fluid path length) can be decreased. Thus the invention teaches shortening the path length by placing arterial and venous ports within the intervillous space to shorten the distance between them.

FIG. 31 is a side cross-sectional view of a cotyledon being ventilated to provide a baby with fluidic ventilation according to the invention; the baby has been delivered with the spacesuit intact and the umbilical cord has not been cut. Referring to FIG. 31, an arterial catheter CTH-A and a venous catheter CTH-V are inserted parallel to each other and perpendicular to the chorionic plate from the top side of the cotyledon to a full depth in the intervillous space. In operation, a ventilating fluid is urged from a ventilator via an arterial line 75-A through the arterial catheter CTH-A; the fluid emerges from a series of arterial fluid ports 76-A disposed along a length of the arterial catheter CTH-A within the intervillous space; in turn, the fluid travels to corresponding venous fluid ports 76-V disposed along a length of the venous catheter CTH-V within the intervillous space and is returned to the ventilator via a venous line 75-V. Though shown facing the viewer in FIG. 31 for drawing convenience, the shortest fluid path length is provided when opposing arterial and venous ports face each other.

Recalling the photographic paper analogy, in FIG. 31 each of the arrows indicating fluid flow between respective arterial and venous ports 76-A, 76-V is analogous to one of a number of conveyor belts, and a distance between the arterial and venous ports is analogous to a length of the conveyor belt, corresponding to a fluid path length between ports. In the example of FIG. 31, the fluid path length between adjacent arterial and venous ports 76-A, 76-V has been nominally set to approximately 1 cm by spacing the arterial and venous catheters CTH-A, CTH-V apart laterally by a distance of 1 cm, as shown. Other predetermined spacing may also be employed.

In the example of FIG. 31, catheter portions making contact with the baby's spacesuit are preferably made of glass; nominally, the arterial catheter CTH-A has inner and outer diameters of 0.7 mm and 1.0 mm, respectively, and arterial ports 76-A are formed by 0.7 mm diameter holes and are spaced apart 3 mm on center, and the dimensions of the venous catheter CTH-V may be the same. For reduced flow resistance, the flow diameter of the venous catheter may be greater than that of the arterial catheter, and the sum of the cross-sectional areas of the venous ports may also be greater. To reduce clogging, venous ports may be larger; to promote filtering, venous ports may be smaller, albeit more numerous to reduce flow resistance.

Although only one arterial and one venous catheter are shown in FIG. 31 with a one-to-one correspondence between them, any number or correspondence of catheters including both arterial and venous ports within the intervillous space may be arrayed in predetermined patterns for optimized flow in the intervillous space. Although fluid flow is shown emerging from arterial ports perpendicular to the arterial catheter, other angles of emergence are possible; although stream flow from holes forming arterial ports is shown, arterial ports may be adapted to urging fluid to flow in streams or diffusely, including out of holes, rings, grooves, or nozzles. Although separate catheters for arterial and venous flow are shown in FIG. 31, arterial and venous fluid lines and ports may be disposed on the same catheter in various patterns, an example being shown in FIG. 14.

Referring to FIG. 31, catheters may be placed in the intervillous space vertically as shown (perpendicular to the chorionic plate). Alternatively, they may be coiled around the villus tree, placed horizontally under the septum SEP (parallel to the surface of the chorionic plate), or placed horizontally after piercing the septum under guidance.

Referring to FIG. 31, inasmuch as the venous catheter CTH-V is sufficiently capable of withdrawing all of the ventilating fluid being introduced by the arterial catheter CTH-A, there will be no need to maintain the fluidic patency of the venous ports 74-V remaining as remnants of maternal venules at the top of the cotyledon. Instead, these may be covered or plugged. Alternatively, the trophoblastic shell may be removed, including the septa. Although only one cotyledon is shown in FIG. 31, the rest are similarly ventilated according to the invention; that is to say, the alluvia anterioris is ventilated as a whole.

For half a century the prior art has sought to develop what is termed "extracorporeal support" for premature newborns whose lungs are too undeveloped to survive by breathing. See Schoberer et al., "Fifty Years of Work on the Artificial Placenta: Milestones in the History of Extracorporeal Support of the Premature Newborn," Artificial Organs, Vol. 36, No. 6, 2012, pp. 512-516. The main work has been done using animals as a model. This has involved circulating oxygenated blood through the body in combination with parenteral nutrition.

But in view of the teaching of the invention, a limitation of such work appears to be the elimination of the placenta from the circuit. For rather than being merely a source of oxygen, nutrition, and manufactured compounds, the placenta is an organ responsive to feedback concerning the formal body's physiological state and metabolism. For this reason, even after the umbilical cord has been cut, either the baby's placenta, or one discarded by a donor at birth, should be kept in the circuit and fluidically ventilated according to the invention. For this purpose, the vessels of the umbilical cord, where it inserts into the chorion, may be cannulated and the placenta added to the extracorporeal circuit either in series or in parallel. Or the placenta may be relied upon on its own, though perhaps with the aid of pumps to improve umbilical flow through the chorion; pumps will be especially important when the donor placenta is from a baby who was much further along in development. Eventually, it may be possible to discern the feedback response mechanisms of the placenta by way of differential monitoring of the components of inflow and outflow into the chorion from the umbilical vessels. By emulating such mechanisms, it may then be possible to modify the blood accordingly in a circuit that leaves out the placenta. But until then it seems preferable to keep the placenta in the circuit. In a reciprocal way, babies in the inventive incubators struggling to thrive in their spacesuits may be further provided with extracorporeal assistance.

FIG. 32 is a schematic diagram of the intervillous space, illustrating several options of fluid being delivered and withdrawn from the intervillous space via an intrauterine ventilator. Referring to FIG. 32, a maternal ventilation circuit 77 is formed by the mother passing maternal ventilation through the intervillous space IVS from arterial ports A' to venous ports V' as provided by her endometrial arterioles and venules, respectively.

In general, the intrauterine ventilator can add or subtract fluid from the intervillous space, depending on the setup, whether in net or equal amounts. To add fluid, an arterial supply line 78 delivers fresh ventilating fluid via arterial ports A" in a ventilation catheter; to subtract fluid, a venous return line 79 withdraws waste fluid via venous ports V" using either the same or different catheter. For equal amounts, such that a net contribution of fluid to the intervillous space by the intrauterine ventilator is zero, the arterial supply line 78 provides the same amount of fluid as is withdrawn by the venous return line 79. For net positive amounts, such that more fluid is delivered than returned to the ventilator, a net amount of fluid provided by the arterial supply line 78 takes a maternal return path 80 via maternal venules A'; the added fluid is then relieved from the mother's system by urination or dialysis. For net negative amounts, more fluid is withdrawn by the venous return line 79 than is supplied by the ventilator; the fluid lost by the mother can be replenished with an IV drip system.

To give an example of a net positive supply, during the whole blood stage, ventilating fluid formulated based on a buffered salt solution can be delivered by the arterial supply line 78, but with no venous return line 79; instead, the excess fluid is taken up by maternal venules V' according to the maternal return path 80; in one formulation, the buffered salt solution has a hyperoxic tension, which averages in by mixing with maternal ventilation to maintain physiologic levels in the intervillous space.

In general, selected contents of the ventilating fluid supplied by an intrauterine ventilator may be concentrated over physiologic values for dilution to physiologic values by mixing with maternal ventilation in the intervillous space. In such cases, the ventilating fluid should be dispersed by a ventilation catheter in the intervillous space in a manner that promotes mixing with maternal ventilation. For example, a short fluid path directed as a stream between arterial and venous ports will promote less mixing than a long path directed diffusely; similarly, one stream will promote less mixing than two streams totaling the same volume as the first.

In this disclosure, a ventilation catheter having only arterial ports is called an A-type catheter; one having only venous ports is called a V-type catheter; and, one having both arterial and venous ports is called an A/V-type catheter.

An A-type catheter may be placed over the alluvia anterioris by itself, so that venous return is accomplished by the mother; a V-type catheter or transcervical access port may be added for additional drainage. Similarly, a V-type catheter may be placed over the alluvia anterioris by itself, for example to encourage arterial flow from the mother or to clear debris.

Fluid in an A-type catheter may be urged in a manner of continuous, intermittent, pulsating, or reciprocating (to-and-fro) flow. In the case of reciprocating flow, a venous stroke draws less fluid back than is pushed forward by an arterial stroke, so as to provide a net movement of fluid in the arterial direction. Fluid in V-type catheters may be similarly urged but in the opposite direction.

A plurality of A/V-type ventilation catheters may be provided to cover an area of the gestational sac. A-type and V-type catheters may be provided in alternation; for example, an A-type catheter centrally bisecting the alluvia anterioris may be sided on opposite sides by two V-type catheters in a parallel configuration.

FIGS. 7, 10, and 13 show a ventilation catheter CTH serving the alluvia anterioris; but the posterior may also be ventilated or provided with a drainage (venous) catheter.

Referring to FIG. 4, an oxygen sensor placed in the intervillous space of the alluvia anterioris may be used to provide feedback on the oxygen tension of the intervillous space. If the oxygen tension of ventilating fluid VF in the intervillous space is below a predetermined optimal value, the rate of flow can be increased by means of the regulator 6, or the oxygen tension of the fluid VF in the reservoir 4 can be increased. Vice versa, if the oxygen tension in the intervillous space is above optimal, the rate of flow can be decreased, or the oxygen tension in the reservoir 4 can be decreased. It is preferable to shield the oxygen sensor from direct flow emerging from an arterial port, in this case tubing 7, so that an average value after mixing is obtained. A plurality of oxygen sensors may be used to detect average values and regional distributions.

Rather than placing a sensor directly within the intervillous space, the oxygen tension may also be monitored by sampling fluid from a venous port. For example, referring to FIG. 4, venous fluid may be sampled from fluid exit port 10. However, though not shown in FIG. 4, it is preferable to sample oxygen tension via a sensor placed within the intervillous space of the alluvia anterioris or via venous fluid withdrawn from a venous port in fluidic communication with the intervillous space of the alluvia anterioris. Referring to FIG. 13, fluid in the intervillous space may be sampled and monitored by means of a proximally disposed sensor in communication with a catheter channel for withdrawing venous fluid, which in the case of the catheter of FIG. 14 is either of the two side channels 35-V.

In a one-pass disposable ventilation scheme, such as shown in FIG. 4, to reduce an amount of ventilating fluid used in the course of incubation so as to conserve costs, a slow rate of fluid flow allows the baby to more fully consume vital substances in the ventilating fluid while maintaining a rate of flow needed to remove wastes and prevent toxic buildup. However, the slower the flow rate, the greater the depletion of oxygen; thus, when employing slow flow rates in a non-recirculating scheme, formulas for the ventilating fluid that are optimized for anaerobic metabolism are preferred to minimize reliance on oxygen. (More precisely, recalling the photographic paper analogy, it is longer exposure times that offer the greater depletion of the ventilating fluid.)

FIG. 14 shows arterial ports 34-A adapted to streaming flow; alternatively, arterial ports may be adapted to other patterns of flow, e.g., diffuse (spraying) flow. FIG. 14 shows arterial ports 34-A disposed only on one side of a catheter CTH; this is in keeping with uses where the side with no ports is in proximity to a wall such as the uterine wall or chorionic plate. But in general ports may be disposed on various sides, depending on use.

The reported fluid pressure in the intervillous space is on the order of 10 mm Hg above atmospheric pressure. Since this is within atmospheric variations, it appears unlikely that an ambient pressure of fluid in the inventive incubators will need to be elevated with respect to that of a surrounding room.

Although venous flow in the maternal body is normally not less than atmospheric pressure, in some cases suction flow may be applied to a venous flow line or port according to the invention.

Catheters may be attached or molded into an ATC. For example, ventilation catheters may be attached to the bottom half of the ATC, along with chorionic spacers, to facilitate an accurate arrangement of the catheters when placing the baby in the capsule; loose distal ends of the catheters may be tucked into the top half along with the baby as the halves are joined.

Distal sections of a catheter may be disposed with preset curvatures to match those of an ATC or the uterus so the catheter will rest easily in place. This will help prevent the catheter from buckling, impacting the chorionic plate, or getting pinched off as it bends around a tortuous path such as where the catheter bends at the anatomical internal os of the cervix (see FIG. 7). Sections of a catheter may be reinforced or mechanically adapted to predetermined shapes or bending according to the art.

The design and placement of catheters and other devices in the uterine cavity should take into account growth, so chorionic villi will not be strangled, cut, or occluded as the baby grows. In general, loops and bends around the chorionic villi are to be avoided. Avoiding loops and bends will also be of aid for devices scheduled for removal. But if loops or bends around the chorionic villi or other potential sources of constriction are unavoidable, devices may be scheduled for degradation in whole or in part in advance of constriction; for example, they may be provided with fusible links that degrade to obliterate such obstacles before growth-related constriction can occur.

For example, referring to FIG. 15 a hole in the chorionic spacer CS is sized to permit the catheter CTH to slip freely therethrough as the baby grows, and it also aids removal of the catheter. Another embodiment of a chorionic spacer takes the form of a coiled spring threaded around one or more chorionic villi; but the spring is scheduled to degrade before growth-related constriction of the chorionic villi can occur.

One way to moderate incubator conditions is in reference to predetermined values for each parameter being monitored and maintained; typically, such values will be acquired from studies of normal physiologic ranges. Another way is to monitor expressed factors or biological markers which serve as indicia for adjusting conditions. For example, the baby may express a factor which is known from studies to indicate hypoxia when detected in predetermined quantities or concentrations; in turn, a computer processor responsive to a sensor detecting such an indicium may signal an oxygenator to raise oxygen tension in the intervillous space; similarly, a marker indicating oxidative stress may signal a need to reduce oxygen tension.

It is premature to rule out the possibility that oxygen tensions above or below physiologic are also compatible with incubation according to the present invention. Thus, although incubation at physiologic oxygen tensions is contemplated in view of FIGS. 28 and 29 and related data, other oxygen levels may also be compatible with life. However, as shown in FIG. 27, peak levels in the risk of birth defects indicate the need to reduce an amount of stress being induced during heightened periods of teratogenic susceptibility, including oxidative stress. For this reason, it is likely that low levels of oxygen will be preferred during these periods.

The human placenta is described as a "nutrient sensor" that adapts to optimize the transfer of nutrients after sensing the nutrients supplied by the mother. This includes changes in the expression density and transport activity of transport systems disposed in the walls of the placenta. See Larqué et al., "Placental Transfer of Fatty Acids and Fetal Implications," The American Journal of Clinical Nutrition, Vol. 94, Suppl., 2011, pp. 1908S-1913S; Magnusson-Olsson et al., "Effect of Maternal Triglycerides and Free Fatty Acids on Placental LPL in Cultured Primary Trophoblast Cells and in a Case of Maternal LPL Deficiency," American Journal of Physiology—Endocrinology, and Metabolism, Vol. 293, No. 1, 2007, pp. E24-E30; and, Lager, "Cytokines and Lipids in Pregnancy: Effects on Developmental Programming and Placental Nutrient Transport," Ph.D. Thesis, University of Gothenburg, Sweden, 2010.

Since changes in the density and expression of transport systems take time, the baby may experience "transplant shock" during the meantime if transferred between environments differing radically in content. To give a speculative example, an incubation diet rich in free fatty acids (bound to albumin) may leave the baby unprepared to thrive off of maternal triglycerides (incorporated into lipoprotein particles) upon transfer to the uterus; if so, it would make sense to incubate the baby with a ventilation formula including triglycerides in order to build up the expression and activity of the corresponding transport systems prior to transfer so as to reduce the potential for transplant shock. At any rate, further research is needed to elucidate the functions and mechanisms of transport across the placenta. Advantageously, in an incubator according to the invention, these and other such matters of nutrition, physiology, endocrinology, and metabolism will be easily and safely elucidated by clinical studies in which variables of the ventilating fluid are controlled and changes in variables are monitored over time.

N. Open Access Alluvial Incubator

FIG. 33 is a side cross-sectional view of an exemplary embodiment of an open access alluvial incubator 81 according to the invention.

Referring to FIG. 33, the open access incubator 81 comprises: enclosure walls 82 forming an enclosure having sidewalls and a flooring for an alluvial baby B and a removable cover 83 for an open top to access the baby B therein; a microfluidic ventilator 84 to circulate first and second ventilating fluids VF1, VF2 within the enclosure; a bidirectional ventilation head VH-A/V for use within the enclosure to fluidically ventilate an alluvia anterioris with the first ventilating fluid VF1 via first arterial and venous catheter lines 85-A, 85-V connected to the ventilator 84, wherein a presenting face of the ventilation head VH-A/V has a chorionic spacer CS protruding therefrom to maintain a predetermined minimum distance of spacing between the presenting face and a chorionic plate, and wherein a first temperature sensor T1 is disposed on a distal end of the chorionic spacer CS to monitor patient temperature in contact with the chorionic plate via a first sensor line 86 connected to the ventilator 84; second arterial and venous catheter lines 87-A, 87-V connected to the ventilator 84 to circulate the second ventilating fluid VF2 within the enclosure, wherein the second fluid VF2 fills the enclosure to cover the baby B inside; a second temperature sensor T2, being in contact with the second fluid VF2 within the enclosure to monitor a temperature of the second fluid VF2 via a second sensor line 88 connected to the ventilator 84; and, catheter and sensor line connectors 89, 90 passing through the enclosure walls 82 to connect the ventilator 84 to the enclosure.

Not shown in FIG. 33 are a cradle support for the baby B within the enclosure walls 82; an imaging device to visualize the baby B in the incubator 81; monitor screens and display panels in communication with incubator systems to display incubator conditions, settings, and images; audio speakers in communication with incubator systems to audibly indicate incubator conditions, settings, and alarms; means of remote data transfer to remotely monitor and control incubator systems; and, an electrical power supply for incubator systems.

Also not shown in FIG. 33 is means to pass instructions to a computer associated with the ventilator 84 to enable an operator to control incubator systems electronically; exemplary means includes a touch screen, control panel, keyboard, or computer terminal. To give an example, the operator may use the touch screen to instruct the ventilator 84 to maintain the temperature of the second ventilating fluid VF2 within the incubator enclosure (i.e., ambient temperature) at a desired setting of 37.0±0.2° C. as monitored by the second temperature sensor T2. In one embodiment, to accomplish this task the ventilator 84 heats or cools the second fluid VF2 by a computed increment based on feedback from the second temperature sensor T2 as the second fluid VF2 is urged into the incubator enclosure via the second arterial catheter line 87-A; exemplary heating and cooling means, e.g., thermostatic reservoirs, are disclosed in my incorporated teachings.

To give another example, the operator may use the touch screen to instruct the ventilator 84 to maintain the baby's temperature (which can differ from the ambient temperature setting) at a desired setting of 37.0±0.1° C. as monitored by the first temperature sensor T1. In one embodiment of a thermoregulation scheme, the ventilator 84 accomplishes this task as follows: while urging the first ventilating fluid VF1 to flow from the ventilation head VH-A/V at a predetermined optimal flow rate, and while maintaining the temperature of the second ventilating fluid VF2 within the incubator enclosure (i.e., ambient temperature) within a predetermined optimal range: if the baby's temperature is higher than the desired setting, the ventilator 84 cools the first fluid VF1 by a computed increment as it is urged to the ventilation head VH-A/V via the first arterial catheter line 85-A; conversely, if the baby's temperature is lower than the desired setting, the ventilator 84 heats the first fluid VF1 by a computed increment. Other thermoregulation schemes will be appreciated in view of my incorporated teachings.

FIG. 34 is a side perspective view of an exemplary bidirectional ventilation head VH-A/V according to the incubator of FIG. 33. Referring to FIG. 34 in view of FIG. 33, the presenting face 91 of the ventilation head VH-A/V is disposed with arterial and venous ports 92-A, 92-V; a diameter and curvature of the presenting face 91 are preferably sized to ventilate the entire alluvia anterioris; the first temperature sensor T1 protrudes from the distal end of the chorionic spacer CS to touch against the chorionic plate over the umbilical cord; and, a conduit 93 is provided to house a length of the catheter and sensor lines 85-A, 85-V, 86 proceeding from a back of the ventilation head VH-A/V. With respect to anatomy, typically the umbilical cord inserts centrally into the alluvia anterioris (central insertion), rather than off-center (eccentric insertion), near its edge (marginal insertion), or outside its border (velamentous insertion); with central insertion, the temperature sensor T1 and its chorionic spacer CS will be positioned at or near the center of the ventilation head VH-A/V, as shown.

Referring to FIG. 34, shown is an exemplary hexagonal packing structure of arterial and venous ports 92-A, 92-V, the ports lying flush with the presenting face 91, the arterial ports 92-A outnumbering venous ports 92-V by 2-to-1, and the sum of the cross-sectional areas of the venous ports 92-V exceeding that of the arterial ports 92-A by 3-to-2. Many other packing structures, elevations, correspondences, and relative sizes may be employed among ports. For example, each arterial port may be elevated as a short catheter extension protruding from the presenting face, with an opening at its distal end. To give another example, in the manner of FIG. 31 arterial and venous ports may be disposed on an array of catheters protruding from the presenting face of a ventilation head. Although in FIG. 33 one ventilation head is shown covering the alluvia anterioris, several ventilation heads may be combined to cover the alluvia anterioris, especially for large babies. For example, referring to FIG. 31 individual ventilation heads of corresponding sizes may be employed to serve respective cotyledons.

FIG. 35 is a side cross-sectional view of a modification of the bidirectional ventilation head VH-A/V shown in FIGS. 33 and 34. Referring to FIG. 35, to improve the isolation of the first ventilating fluid VF1 from the surrounding second ventilating fluid VF2, a flexible curtain 94 is disposed circumferentially around the ventilation head VH-A/V. A proximal edge of the curtain 94 is attached over a side edge 95 of the ventilation head VH-A/V. For maximum fluidic isolation, a distal edge of the curtain 94 abuts the chorionic plate. The operator may use a probe to guide the curtain around the chorionic villi.

Referring to FIG. 33, the ventilation head VH-A/V may be mounted to a sidewall or flooring of the enclosure, including in a manner permitting stationary, swivel-type, or extensible movement of the head VH-A/V.

Although the second ventilating fluid VF2 is shown being urged into and out of the enclosure via a single pair of arterial and venous catheter lines 87-A, 87-V, in practice a plurality of arterial and venous catheter lines 87-A, 87-V are employed. Although the second ventilating fluid VF2 is shown being urged into and out of the enclosure via simple connectors 89, in practice flow nozzles are attached to the connectors 89 to direct the fluid VF2 to circulate within the enclosure.

Although a single second temperature sensor T2 is shown for monitoring the temperature of the second ventilating fluid VF2, a plurality may be employed to detect temperature differences as a measure of how well the fluid VF2 is being circulated.

In addition to flow nozzles, a mechanical circulator may also be employed according to the art to circulate the second ventilating fluid VF2 within the enclosure.

The ventilator 84 may be responsive to a fluid fill sensor to monitor and maintain a fluid level of the second ventilating fluid VF2 within the enclosure. For example, after introducing the baby B into the enclosure, the operator may use the touch screen to signal the ventilator 84 to bring the second ventilating fluid VF2 up to a predetermined fill level.

The enclosure flooring may have a drain controlled by a valve responsive to the ventilator 84. For example, if the fill sensor detects a fluid level nearing overflow, the valve can be opened to release fluid. Or for example, when introducing an instrument into the enclosure, the operator may use the touch screen to signal the ventilator 84 to drain fluid in an amount to offset a volume to be displaced by the instrument.

Noted is that although a spillway port may be disposed in the sidewalls near the top of the enclosure to relieve overflow, compared to a flooring drain an air space left by the port and an associated drainage conduit may reduce an isolation of the enclosure as is needed to reduce pathogen exposure.

To purge air and to circulate clean air of a predetermined composition and temperature within void spaces remaining at the top of the enclosure with the cover 83 on, air lines of an airflow system may be attached to the top of the enclosure above a fluid fill line via the cover 83 or enclosure walls 82.

A temperature sensor may be included at the distal end of arterial catheter lines before the point where fluid emerges; this will give the ventilator 84 feedback on changes in temperature taking place over the course of the lines.

Except for temperature, it will generally be more convenient to monitor venous fluid after it has returned to the ventilator 84. Another exception occurs for blood gas sensors in view of a high rate of oxygen consumption combined with red blood cells, in which case proximal monitoring of the venous return will reflect equilibrated values rather than actual values in the intervillous space.

Although the first temperature sensor T1 only monitors patient temperature, additional sensors may be employed to distinctly monitor the temperature and temperature distribution of the intervillous space.

Referring to FIG. 33, the incubator 81 further includes a cradle support for the baby B. A first exemplary cradle support is provided by a forceps to hold the baby B; for example, the forceps or other clasping instrument may be mounted on a sidewall or flooring of the enclosure, including in a manner permitting fixed, swivel-type, or extensible operation; alternatively, the forceps or other clasping instrument may be attached to the ventilation head VH-A/V. For example, the forceps may clasp the baby B from the sides. The forceps may lock rigidly to hold the baby B or its opening may yield in an elastic manner over a limited range as the baby B grows.

A second exemplary cradle support is provided by one or more straps to hold the baby B against the ventilation head VH-A/V; for example, the straps may be elastic and stretch around the baby B to be hooked onto the ventilation head VH-A/V, which though not shown may provided with a set of pegs on its sides for receiving the straps.

Referring to FIGS. 33 and 34, generally speaking the operator introduces the baby B into the incubator 81 by hand, forceps, or other instrument. After orienting the alluvia anterioris against the presenting face 91 of the ventilation head VH-A/V, the operator applies the forceps or straps of the cradle support to cradle the baby B. To remove or reposition the baby B, the operator releases or adjusts the forceps or straps of the cradle support.

In the case of hospice or ongoing care, a portion of the posterior aspect of the gestational sac may be surgically opened or removed by the operator. Referring to FIG. 33, in such a case the second ventilating fluid VF2 may be replaced with fluid analogous to chorionic or amniotic fluid, depending on whether the amnion is breached as well as the chorion. See FIGS. 1A-1B and 2B. Referring to FIG. 35, in such a case the flow curtain 94 may be further adapted to wrap around an inferior (umbilical) side of the alluvia anterioris for isolation; in turn, a forceps or clamp may be employed to press upon the wrapped inferior side so that a superior (presenting) side of the alluvia anterioris abuts the ventilation head VH-A/V. With the alluvia anterioris wrapped and clamped to the ventilation head VH-A/V, then rather than requiring further support the baby's formal body may be left to dangle from the umbilical cord.

Alternatively, in the case of hospice or ongoing care the posterior of the gestational sac may be opened, cut, and inverted in such a way that the cut edge is pulled over the side edge 95 of the ventilation head VH-A/V to provide isolation. A clamp may be employed to secure the cut edge to the ventilation head VH-A/V. Further clamping may be employed to ensure the presenting side of the alluvia anterioris evenly abuts the ventilation head VH-A/V.

FIG. 36 is a side cross-sectional view of a variation of the FIG. 4 incubator. In the FIG. 4 incubator, arterial flow emerges from the tubing 7 and ventilates the baby B in the incubator bag 8 before going out the fluid exit port 10 in the bottom. In the FIG. 36 incubator, a similar incubator bag 96 is employed, but in this case a bidirectional ventilation head VH-A/V is employed instead of a single tubing to ventilate the baby B. Referring to FIG. 36, reminiscent of a shower cap, an opening 97 sized to admit the baby B at the top of the incubator bag 96 draws close by an elastic band around the conduit 93 at the back of the ventilation head VH-A/V. As shown, the baby B is cradled by the incubator bag 96 up against the ventilation head VH-A/V with the alluvia anterioris abutted thereto. A venous catheter 98-V proceeds within the incubator bag 96 from a connector on the ventilation head VH-A/V to enable ventilation of the alluvia posterioris via venous ports 99-V disposed in a distal end of the venous catheter 98-V; alternatively, a fluid exit port may be disposed in a bottom of the FIG. 36 incubator bag 96 in likeness to the fluid exit port 10 of the FIG. 4 incubator bag 8. To maintain fluidic patency, an inner wall of the incubator bag 96 may be disposed with raised bumps in the manner of a chorionic spacer.

Rather than containing a separate incubator within, a workspace according to the invention may also serve as an open access alluvial incubator in its own right, particularly on a temporary basis, for example during surgery or when prepping the baby for transfer to the mother's uterus. Here such a workspace is called a workspace incubator. In the workspace incubator, rather than being completely submerged under fluid, the baby is at least partly exposed to air in the workspace, although in general at least an alluvia anterioris is misted, sprayed, showered with, or submerged in a ventilating fluid. The temperature, humidity, and gaseous content of the air are controlled within a workspace enclosure. The baby rests on a table or cradle support within the workspace or is held by the operator.

To give an example of a cradle support which is based on the ventilation head VH-A/V shown in FIG. 34, with its presenting face facing up a ventilation head may be adapted to form a cradle support for a baby to rest on, with the alluvia anterioris facing down to receive fluidic ventilation therefrom. In this example, the air of the workspace enclosure surrounds the alluvia posterioris and is maintained at a temperature of ~37° C. and relative humidity of 95-100%; the air has an oxygen composition accorded to the baby's development-specific requirements. The alluvia posterioris may be kept moist with ventilating fluid by periodic misting or by covering the baby with a moistened blanket which is changed periodically.

The workspace incubator presents unique thermoregulatory challenges. For example, for a given temperature of the ventilating fluid, there will be less heat transfer of the baby's endogenous body heat when misting or spraying the alluvia anterioris than when the alluvia anterioris is showered or submerged. Also, depending on humidity and warmth, there is a potential for the baby to experience evaporative cooling, unlike when fully submerged. Thus it is important to monitor patient temperature and to moderate thermoregulatory parameters of the workspace environment accordingly.

To take the baby's temperature, a temperature sensor may be placed in contact with the chorionic plate over the umbilical cord; non-contact thermometry or thermography may also be practical in some cases. To regulate patient temperature based on feedback from patient temperature readings, a variety of incubation parameters can be modulated, for example: an ambient temperature of the air; a flow rate of the air passing in contact with the baby; an ambient temperature of the ventilating fluid; a flow rate of the ventilating fluid passing in contact with the baby; an amount of warmth provided by radiant heat lamps; an amount of heat insulation provided by a cover or blanket placed over the baby; an amount of heat dissipation provided by a heat sink surface in contact with the baby; and, a metabolic fueling of the baby's endogenous heat production. See U.S. Pat. No. 9,056,039; claims 1 and 2.

In the workspace incubator, when the gestational sac is breached, e.g., during surgery, the amnion or formal body is irrigated with fluid analogous to chorionic or amniotic fluid, depending on whether the amnion is breached as well as the chorion. Ventilating fluid is supplied in the workspace by a fluidic ventilator; other fluids to irrigate or wash the baby may be supplied by fluid reservoirs in combination with means for urging fluid such as a roller pump. Fluid lines, filters, ventilation heads, nozzles, and other fluidic accessories may be provided in the workspace for operator convenience in ventilating, irrigating, and washing the patient. Prewarmed fluids may also be supplied for manual misting or spraying via handheld spray bottles. The workspace is provided with drainage and means of fluid aspiration to remove fluid from the workspace.

If the humidity of the workspace is high enough to condense vapor on the baby, it should be kept in mind that the air vapor will not have the same nutrient composition as the ventilating fluid with which the baby is being misted or sprayed. Thus, when misting or spraying the alluvia anterioris in the open access workspace, it is generally preferable for the humidity of the air not to be so high as to condense on the baby. For short periods, a moistened baby may be able to survive within the workspace without additional fluidic ventilation based on the temperature, humidity, and oxygen content of the air; but even so, the alluvia anterioris should at least be periodically irrigated with a physiological buffered salt solution even in absence of a ventilating fluid or else toxicity from the baby's accumulated wastes will build up to a critical level.

The workspace is provided with an air circulator; however, the baby should be shielded from draft or else an effect on flow-related heat dissipation and evaporation must be taken into account. To reduce contamination by particulate matter, the workspace should employ clean room technology or at least a laminar flow hood.

The sterility of the workspace is critical. In general, keeping the baby free of infection is especially critical for patients destined for transfer; otherwise the infection may spread to the mother after transfer.

7. Miscellaneous Notes

A. Anatomy and Physiology

For drawing convenience, FIG. 1B shows an abrupt transition between the alluvia anterioris AA and the alluvia posterioris AP. But in early development, arterioles and venules in the chorionic plate over a broad area may communicate physiologically with the formal body via the umbilical cord, which is also called the body stalk at this stage. Thus a more general guidance is that fluidic ventilation should be preferentially applied to regions of the gestational sac in proportion to the prominence of their chorionic villi.

Although FIG. 1A shows substantially the whole body of a baby B almost seven weeks after fertilization, the trophoblastic shell is missing. In contrast, FIG. 37 shows the whole body of same baby B including the trophoblastic shell TS.

Referring to FIG. 6, when the baby B is delivered from the uterine tube UT, much of the trophoblastic shell TS will likely separate from any chorionic villi that are anchored to it, being adherent to the uterine tube UT, as shown. When the trophoblastic shell TS is entirely removed, the baby B will then have the appearance shown in FIG. 1A. In contrast, FIG. 37 shows the whole body of the baby B including the trophoblastic shell TS, without any maternal tissue.

The trophoblastic shell TS represents the outermost extremity of the baby's peripheral body. In addition, the baby sends out a dispersion of free cells, mainly to modify the vasculature of the uterus. However, FIG. 37 represents the full extent of the baby's continuous body at this stage. In other words, FIG. 37 reflects the full continuous extent of what a conceptus looks like at this stage.

FIG. 2B shows the baby's peripheral body (spacesuit S) at the same stage as FIG. 37, except in FIG. 2B the trophoblastic shell TS is absent. However, the full extent of the baby's spacesuit S includes the trophoblastic shell TS, as shown in FIG. 37.

FIG. 38 is a side cross-sectional view of the whole body of a baby B a little over 12 weeks after fertilization. Referring to FIG. 38, there are key differences compared with FIG. 37: the amnion has fused with the chorion, so instead of separate chorionic and amniotic cavities for fluid there is just the one amniotic cavity for amniotic fluid; the intervillous space of the alluvia posterioris has been obliterated due to its chorionic villi having atrophied between a sandwiching together of the trophoblastic shell and chorionic plate; and, the intervillous space IVS of the alluvia anterioris AA has taken on a discoid appearance, in contrast to the concentric appearance of the intervillous space shown in FIG. 37 which spans the entire circumference of the chorionic plate from anterior to posterior. See also FIGS. 1B, 2B, and 8.

Referring to FIGS. 37 and 38 in view of FIGS. 2B and 8, an anatomical structure formed by the chorionic plate and trophoblastic shell TS in their bounding of the intervillous space IVS does not appear to be named in the literature; in this disclosure it is called the hemochorial bladder. According to its function, the hemochorial bladder is filled with a circulation of maternal ventilation to fluidically ventilate the baby. Here, three stages of the hemochorial bladder are identified in order as the sinusoidal, concentric, and discoid stages.

The spacesuit first becomes visible ~2 days before hatching as a single fluid-filled membrane called the chorion (Greek "membrane"). At this stage, misnomered the inner cell mass, the baby's formal body abuts the interior wall of the chorion at one side; later the umbilical cord will form between the formal body and the chorion. The hemochorial bladder appears shortly after implantation, as sinuses form in the chorion and fill with an exudate of maternal blood; this represents the sinusoidal stage. Noting in FIG. 37 that the chorionic plate and trophoblastic shell TS are concentrically arranged, this represents the concentric stage of the hemochorial bladder. In contrast, FIG. 38 represents the discoid stage; noted is that cotyledons form in this stage as septa become prominent.

The chorionic plate, chorionic villi, and trophoblastic shell are all included under the term chorion. The trophoblastic shell may also be called the chorionic shell or the upper plate of the chorion. At implantation, at first there are no villi and the chorion consists of a single membrane rather than upper and lower plates.

The word placenta (Latin "flat cake") refers literally to the discoid appearance of the hemochorial bladder at term, which appears as a flat cake; this is sometimes referred to as the true or definitive placenta. Present-day usage is varied, and may refer to the definitive placenta, any extent of the chorion covered with villi, or even the entire afterbirth. With revised knowledge concerning the genetic identity of tissues has come a tendency to refer to the placenta as a "fetomaternal" organ or unit, given that upon delivery its exterior surface is covered with maternal tissue shed from the endometrium. See FIG. 31, showing a distinction between the tissues of the baby and mother associated with a cotyledon after delivery at or near term. In contrast, the meaning of the term "spacesuit" reflects the full extent of the baby's peripheral body, without any inclusion of maternal tissue; noted is that the meaning is literal within its fluidic context.

The hemochorial bladder may also be called the hemocyst (hemo-+Greek kystis bladder); the adjective is hemocystic. The hemocyst is what authors refer to as the fetal part of the placenta.

Also called the gestation sac, the gestational sac refers to the chorion and later to the chorion and amnion once they have fused together. In this disclosure, it has been said that a baby is fluidically ventilated by circulating a ventilating fluid over the outside of the gestational sac; but in view of FIGS. 37 and 38, once the hemochorial bladder has formed, for clarity it is noted that this especially means circulating the ventilating fluid within the sinuses or intervillous space of the hemochorial bladder and not merely over the outside of the trophoblastic shell TS.

The exterior of the trophoblastic shell is the presenting face of the baby's body making contact with the mother. Noted is that before implantation the chorion may also be called the trophoblastic shell; but once upper and lower chorionic plates form, only the outermost is to be called the trophoblastic shell.

Referring to FIGS. 37 and 38, during pregnancy endometrial arterioles, venules, and glands communicate fluidically with the intervillous space IVS via corresponding openings in the trophoblastic shell TS. But if the baby is delivered with the trophoblastic shell intact, then access must be gained to the intervillous space in order to fluidically ventilate the baby; for example, the trophoblastic shell can be removed or, as shown in FIG. 31, the trophoblastic shell and any adherent maternal tissue can be penetrated by microfluidic instruments. If the baby is reimplanted with the trophoblastic shell intact over the alluvia anterioris, then the intervillous space should remain catheterized via an intrauterine ventilator until the trophoblastic shell is able to establish fluidic communication with the endometrial arterioles, venules, and glands.

At the histological level, the trophoblastic shell meshes to an extent with the endometrium to which it is abutted, and the affected endometrial tissues are designed to be shed with the trophoblastic shell. But as shown in FIG. 6, in the case of implantation outside the uterine cavity, the trophoblastic shell TS may separate from its anchoring villi to remain adherent to the affected organ, which in this case is the uterine tube UT. But in pregnancy transfers where the baby is delivered from the endometrium, the trophoblastic shell may be more likely to remain intact along with any adherent maternal tissue being shed.

The anatomical distinction between arteries and veins is that arteries carry blood being pumped away from the heart, and veins carry blood back to the heart. The usual case is that arterial blood is oxygenated (red) and venous blood is deoxygenated (blue). But there are two exceptions. Once the baby is born and starts breathing air, pulmonary arteries carry deoxygenated (blue) blood being pumped away from the heart to the lungs, and pulmonary veins carry oxygenated (red) blood from the lungs back to the heart. And before the baby starts breathing air, an umbilical artery carries deoxygenated (blue) blood being pumped away from the heart to the chorion, and two umbilical veins carry oxygenated (red) blood back to the heart from the chorion.

The umbilical artery and the arteries and arterioles of the chorionic plate and chorionic villi contain deoxygenated (waste) blood, and the umbilical veins and the veins and venules of the chorionic plate and chorionic villi contain oxygenated (fresh) blood. Here this is called the chorionic circulation, or the conceptual circulation of the hemochorial bladder. Noted is that some babies have one umbilical vein instead of two. In contrast to the chorionic circulation, endometrial spiral arterioles supply the intervillous space with oxygenated (fresh) blood or plasma, and endometrial venules withdraw the deoxygenated (waste) blood or plasma from the intervillous space. Here this is called the intervillous circulation, or the maternal circulation of the hemochorial bladder. The maternal circulation of the hemochorial bladder also includes exudates and glandular secretions circulating in the chorionic sinuses or intervillous space.

Thus it will be appreciated that the hemochorial bladder serves the same physiological function as the lungs with respect to oxygenating blood, except whereas the lungs are ventilated in a gaseous atmosphere, the hemochorial bladder is ventilated in a fluidic atmosphere. In other words, the lungs experience gas-phase ventilation, whereas the hemochorial bladder experiences liquid-phase ventilation. This explains the rationale for using the term fluidic "ventilation" during gestation, as well as related terms such as fluidic "ventilator."

B. Non-Concepticidal Abortion

Despite being widely used in medical and legal literature, abortion is not a medical or scientific term; rather, it is an ambiguous euphemism having diverse historical meaning. In the early 20$^{th}$ century, the pregnant woman was often called the abortion and she was said to be the one who was aborted (e.g., "whoever aborts a woman"). In more recent times, performance of a procedure to terminate a pregnancy is called the abortion, and the baby is said to be aborted.

Abortion itself is a very general term. For example, a space mission can be aborted; but the abortion should not include the killing of the astronaut onboard the spacecraft.

The medical and scientific term for the killing of a conceptus is concepticide (conceptus+-cide); the adjective is concepticidal. This term leaves no ambiguity. For example, some may debate whether killing a conceptus before implantation is an abortion, but either way it is clearly an act of concepticide.

As one skilled in the art of forensic medicine will appreciate, such as a medical examiner or coroner, the coroner is not concerned about when life begins; instead, the coroner is concerned about how life ended. Thus, having ruled out natural, accidental, and self-inflicted causes of death, the coroner is left with "homicide" as the only possible determination. In the case of a conceptus, the act of homicide is specifically termed concepticide.

With the advent of the present invention comes the prospect of performing an "abortion" of a sort that would not be ruled homicide by the coroner. This is in likeness to aborting a space mission without harming the astronaut. In other words, according to the inventive means of nondestructive ectopic pregnancy management, the cause of any death that may ensue should either be natural or accidental, rather than homicide.

From this it will be appreciated by one skilled in the arts of law and medicine that an abortion, even if necessary to save the life of the mother, is never legally or medically permissible, unless it is a non-concepticidal procedure, which means it is performed with such care and skill that any death the conceptus may suffer will be ruled natural or accidental, rather than homicide. Thus the invention teaches a means of non-homicidal abortion.

C. Conceptiatrics

It is my hope that the present teaching, along with my incorporated teachings, will spark acceptance of a medical specialty of the conceptus, which I call conceptiatrics.

What is claimed is:

1. A nondestructive method of ectopic pregnancy management for a baby who is not yet ready to breathe air, comprising:
    (a) surgically delivering the baby alive from an ectopic pregnancy site within a maternal body with a gestational sac intact;
    (b) transferring the baby to an alluvial incubator with the gestational sac intact;
    (c) incubating the baby in the alluvial incubator with the gestational sac intact;
    (d) enclosing the baby in an absorbable transfer capsule with the gestational sac intact; and,
    (e) implanting the enclosed baby in a uterine cavity.

2. The method of claim 1, wherein an alluvial ventilator fluidically ventilates the baby while performing steps (a), (b), (c), (d), or (e) or at any time during the ectopic pregnancy management.

3. The method of claim 2, wherein a ventilating liquid having a predetermined development-specific composition and oxygen tension is employed to fluidically ventilate the baby via the alluvial ventilator.

4. The method of claim 3, wherein the alluvial ventilator is configured to fluidically ventilate at least an alluvia anterioris.

5. The method of claim 4, wherein the baby is implanted in the uterine cavity with the alluvia anterioris oriented in a posterior fundal position.

6. The method of claim 5, wherein the baby is implanted in the uterine cavity transcervically through a dilated cervix.

7. The method of claim 6, wherein a chorionic spacer, ventilation catheter, optical probe, sensory probe, electrode, or transducer is introduced into the uterine cavity.

8. The method of claim 7, wherein the absorbable transfer capsule is employed as a vehicle for introducing the chorionic spacer, ventilation catheter, optical probe, sensory probe, electrode, or transducer into the uterine cavity with the baby.

9. The method of claim 8, wherein the absorbable transfer capsule degrades within minutes, hours, days, or weeks of being introduced into the uterine cavity to leave at least the alluvia anterioris abutted to an endometrial lining of the uterine cavity.

10. The method of claim 9, wherein a spacer, filler, or expanding member is placed between an alluvia posterioris and a wall of the uterine cavity, between a posterior wall of the absorbable transfer capsule and a wall of the uterine cavity, or between the alluvia posterioris and a posterior wall of the absorbable transfer capsule, whereby the baby is bolstered in the uterine cavity or capsule to promote abutment of the alluvia anterioris to the endometrial lining of the uterine cavity.

11. An absorbable transfer capsule for an implantable baby having an intact gestational sac, comprising: an enclosure for the baby made of at least one absorbable material, the enclosure being sized to the baby and configured for placement of the baby within the enclosure, for entry of the enclosure into a uterine cavity, and for protection of the baby within the enclosure, the at least one absorbable material being disposed to at least partial degradation within a predetermined period of time after introduction into the uterine cavity, the enclosure having a micropump or ventilation catheter to circulate a ventilating liquid within an intervillous space and being configured to degrade after introduction into the uterine cavity to release the baby from the enclosure for implantation or reimplantation.

12. The capsule of claim 11, wherein the enclosure forms a structure selected from the group consisting of a hard shell capsule, soft shell capsule, bag capsule, balloon capsule, straw capsule, and cartridge capsule.

13. The capsule of claim 12, wherein the hard shell capsule has at least two joinable halves to enclose the baby therein.

14. The capsule of claim 12, wherein the soft shell capsule has at least one slit disposed in enclosure walls having an elasticity and flexibility, the at least one slit being sized to admit entry of the baby into the enclosure, whereby the walls fold back about the at least one slit when placing the baby inside the enclosure and then close back over the baby once the walls are released.

15. The capsule of claim 12, wherein the straw capsule has capped ends to hold the baby and a quantity of the ventilating liquid inside the enclosure.

16. The capsule of claim 12, wherein the cartridge capsule, being formed of a series of absorbable layers using layer-based microfabrication techniques, has a microcradle disposed in the layers including a cover layer to hold the baby and a quantity of the ventilating liquid inside the enclosure.

17. The capsule of claim 12, further including disposed therein or attached thereto at least one apparatus selected from the group consisting of an alluvial ventilator in fluidic communication with the ventilation catheter to ventilate the baby in the enclosure, a chorionic spacer to maintain fluidic patency within the intervillous space, a hydrogel micropump or osmotic micropump to ventilate the baby in the enclosure, a reservoir to hold a liquid media, an echogenic structure to guide an operator under ultrasound, a pinch guard comprising a flexible and absorbable strip provided as a barrier to prevent a pinching of the baby when joining enclosure halves, a probe to sense or view a condition, an electrode to detect or emit a signal, and a transducer to detect or emit a signal.

18. The capsule of claim 12, wherein the at least one absorbable material contains hyaluronan.

19. The capsule of claim 12, wherein the at least one absorbable material contains glycoprotein, starch, glycogen, or alginate.

20. The capsule of claim 11, wherein the enclosure forms a structure, wherein said structure is a first capsule, a second capsule, a third capsule, a fourth capsule, a fifth capsule, a sixth capsule, or a seventh capsule, wherein:

the first capsule comprises: the enclosure, forming a rigid structure and having two joinable enclosure halves to enclose the baby therein, the halves being formed of a water-soluble thermoplastic poly(vinyl alcohol) polymer;

the second capsule comprises: the enclosure, forming a rigid structure and having two joinable enclosure halves to enclose the baby therein, the halves being formed of a water-soluble thermoplastic poly(vinyl alcohol) polymer, and further having a coating to delay the at least partial degradation of the enclosure for an additional predetermined period of time;

the third capsule comprises: the enclosure, forming a rigid structure and having two joinable enclosure halves to enclose the baby therein, the halves being formed of a water-soluble thermoplastic poly(vinyl alcohol) polymer, and further having a coating to delay the at least partial degradation of the enclosure for an additional predetermined period of time, wherein the coating comprises reconstituted silk protein fibroin having been purified to remove all traces of silk protein sericin, the fibroin having a crystallinity prepared by physical temperature-controlled water vapor annealing and which crystallinity is proportional to an enzyme degradation rate of the coating, whereby the at least partial degradation of the enclosure is delayed by minutes, hours, days, or weeks;

the fourth capsule comprises: the enclosure, forming a soft structure and having flexible walls to enclose the baby therein, the walls being formed of a thin film or of a non-woven fibrous mat having a predetermined porosity;

the fifth capsule comprises: the enclosure, forming a soft structure and having flexible walls to enclose the baby therein, the walls being formed of a non-woven fibrous mat having a predetermined porosity, wherein the non-woven fibrous mat comprises an electrospun hyaluronan or alginate;

the sixth capsule comprises: the enclosure, forming a soft structure and having flexible walls to enclose the baby therein, the walls being formed of a non-woven fibrous mat having a predetermined porosity, wherein the non-woven fibrous mat comprises an electrospun hyaluronan or alginate, and wherein the non-woven fibrous mat is adapted to being hydrated with a solution containing cells, substances to promote implantation, or nutrients for the baby; and, the seventh capsule comprises: the enclosure, forming a soft structure and having flexible walls to enclose the baby therein, the walls being formed of a thin film, wherein the thin film comprises a thermoplastic starch blended with an aqueous solution of poly(vinyl alcohol).

21. The capsule of claim 11, further including at least one source of alluvial ventilation selected from the group consisting of:
an alluvial ventilator disposed externally to a maternal body and configured to communicate fluidically with the enclosure transcervically via the ventilation catheter;
enclosure walls disposed to a sequential degradation to expose an alluvia anterioris to an endometrial lining of the uterine cavity prior to an alluvia posterioris; and,
a self-contained system disposed within the enclosure for circulating the ventilating liquid.

22. The capsule of claim 11, further including at least one source of the alluvial ventilation selected from the group consisting of:
enclosure walls having a predetermined porosity or at least one hole disposed therein to establish fluidic communication between the gestational sac and a supply of maternal ventilation;
a quantity of the ventilating liquid contained within the enclosure;
a pabulum contained within the enclosure;
a cell scaffold configured to receive maternal cells on enclosure walls;
a fluid reservoir contained within the enclosure for circulating the ventilating liquid; and,
a nutrient for the baby disposed within the at least one absorbable material.

23. The capsule of claim 11, wherein enclosure walls or degrading enclosure walls release at least one beneficial substance for the baby or a mother of the baby.

24. The capsule of claim 11, wherein the enclosure has the micropump.

25. The capsule of claim 11, wherein the enclosure has the ventilation catheter.

26. The capsule of claim 11, wherein the enclosure has the micropump and the ventilation catheter.

27. An alluvial incubator, comprising: an enclosure to maintain an alluvial infant in an environment of controlled temperature, oxygen, hydration, feeding, and waste removal, the enclosure, having a cradle support for the infant, an alluvial ventilator configured to circulate a ventilating liquid within an intervillous space, and a temperature probe adapted to being placed against an outside wall of a chorionic plate to detect an infant temperature.

28. The alluvial incubator of claim 27, wherein the temperature probe is adapted to being placed against the outside wall of the chorionic plate over a chorionic insertion site of an umbilical cord to detect the infant temperature.

29. A nondestructive method of ectopic pregnancy management for a baby who is not yet ready to breathe air, comprising:
(a) surgically delivering the baby alive from an ectopic pregnancy site within a maternal body with a gestational sac intact;
(b) transferring the baby with the gestational sac intact to an alluvial incubator having an alluvial ventilator to circulate a ventilating liquid against the gestational sac;
(c) incubating the baby in the alluvial incubator with the gestational sac intact; and,
(d) implanting the baby in a uterine cavity with the gestational sac intact.

30. The method of claim 29, wherein the baby is fluidically ventilated via a ventilation catheter or ventilation head while performing steps (a), (b), (c), or (d) or at any time during the ectopic pregnancy management.

31. A nondestructive method of ectopic pregnancy management for a baby who is not yet ready to breathe air, comprising:
(a) surgically delivering the baby alive from an ectopic pregnancy site within a maternal body with a gestational sac intact;
(b) enclosing the baby in an absorbable transfer capsule with the gestational sac intact; and,
(c) implanting the enclosed baby in a uterine cavity.

32. The method of claim 31, wherein an alluvial ventilator fluidically ventilates the baby while performing steps (a), (b), or (c) or at any time during the ectopic pregnancy management.

33. A nondestructive method of ectopic pregnancy management, comprising:
(a) surgically delivering a baby alive from an ectopic pregnancy site within a maternal body with at least an anterior aspect of a gestational sac intact;
(b) transferring the baby with at least the anterior aspect of the gestational sac intact to an alluvial incubator having an alluvial ventilator to circulate a ventilating liquid against at least the anterior aspect of the gestational sac; and,
(c) incubating the baby in the alluvial incubator with at least the anterior aspect of the gestational sac intact.

34. The method of claim 33, wherein the baby is fluidically ventilated via a ventilation catheter or ventilation head while performing steps (a), (b), or (c) or at any time during the ectopic pregnancy management.

35. An alluvial incubator, comprising: a flexible bag configured to hold an alluvial infant and a prewarmed ventilating liquid, the bag containing or having disposed on an inside wall a chorionic spacer to maintain fluidic patency within an intervillous space, the bag having a first opening sized for entry of the infant therein, the first opening being adapted to attaching and sealing a distal end of a ventilator tubing thereto by clamping the bag around the tubing after entry of the infant into the bag, a proximal end of the tubing being attached to an alluvial ventilator configured to supply the infant in the bag with a fresh supply of the ventilating liquid, and the bag having a second opening for exit of the ventilating liquid therefrom.

36. The alluvial incubator of claim 35, further including a temperature probe adapted to being placed against an outside wall of a chorionic plate to detect an infant temperature.

37. An alluvial incubator, comprising: enclosure walls forming an enclosure for an alluvial baby having sidewalls, a flooring, and an open top having a removable cover configured for access to the baby therein; a fluidic ventilator to circulate first and second ventilating liquids within the enclosure; a bidirectional ventilation head for use within the enclosure to fluidically ventilate an alluvia anterioris with the first ventilating liquid via first arterial and venous catheter lines connected to the ventilator, wherein a presenting face of the ventilation head has a chorionic spacer protruding therefrom to maintain a predetermined minimum distance of spacing between the presenting face and a chorionic plate, and wherein a first temperature sensor is disposed on a distal end of the chorionic spacer to monitor a patient temperature in contact with the chorionic plate via a first sensor line connected to the ventilator; second arterial and venous catheter lines connected to the ventilator to circulate the second ventilating liquid within the enclosure, wherein the second liquid is configured to fill the enclosure to cover the baby inside; a second temperature sensor, being in contact with the second liquid within the enclosure to monitor a temperature of the second liquid via a second sensor line connected to the ventilator; catheter and sensor line connectors passing through the enclosure walls to connect the ventilator to the enclosure; a cradle support for the baby within the enclosure walls or a support for the alluvia anterioris when dangling the baby within the enclosure by an umbilical cord; an imaging device to visualize the baby within the enclosure; monitor screens and display panels in communication with incubator systems to display incubator conditions, settings, and images; audio speakers in communication with the incubator systems to audibly indicate alarms and the incubator conditions and settings; an electrical power supply for the incubator systems; and, a computer associated with the ventilator to enable an operator to control the incubator systems electronically via one or more peripheral devices.

38. The alluvial incubator of claim 37, wherein the ventilator maintains the second ventilating liquid within the enclosure at a preset temperature of $37.0\pm0.2°$ C. or maintains the patient temperature at a preset temperature of $37.0\pm0.1°$ C.

39. An alluvial incubator, comprising: an enclosure to maintain an alluvial infant in an environment of controlled temperature, humidity, and gaseous content, wherein the enclosure is configured to at least partially expose the infant to air within the enclosure, and wherein an oxygen content of the air is maintained at a predetermined development-specific partial pressure, the enclosure, having a fluidic ventilator configured to fluidically ventilate at least an alluvia anterioris.

40. The alluvial incubator of claim 39, further including a temperature probe adapted to being placed against an outside wall of a chorionic plate to detect an infant temperature.

41. In a nondestructive means of ectopic pregnancy management, a bidirectional ventilation head, comprising: a ventilation head housing having an anterior wall forming a presenting face,
the presenting face, having a diameter and curvature that are sized to an alluvia anterioris, being configured to fluidically ventilate the alluvia anterioris with streams of a ventilating liquid in arterial and venous flow directions via a series of arterial and venous fluid ports disposed in the anterior wall, and having a temperature sensor protruding from a distal end of a chorionic spacer that protrudes from the anterior wall,
wherein the temperature sensor is adapted to monitor a patient temperature by thermal contact with an outside wall of a chorionic plate over a chorionic insertion site of an umbilical cord, and
wherein a conduit proceeds from a posterior wall of the ventilation head housing to house arterial and venous catheter lines to provide fluidic communication with the arterial and venous fluid ports and to house a sensor line to provide sensory communication with the temperature sensor.

42. The bidirectional ventilation head of claim 41, wherein a flexible curtain is disposed circumferentially around the ventilation head housing, a proximal edge of the curtain being attached over a side edge of the ventilation head housing, whereby in operation a distal edge of the curtain abuts the chorionic plate to isolate from a surrounding fluid the ventilating liquid provided by the ventilation head.

43. The bidirectional ventilation head of claim 41, further including a set of pegs disposed on sides of the ventilation head housing and which pegs are adapted to receive one or more elastic straps for holding an alluvial baby against the presenting face of the ventilation head housing.

44. The bidirectional ventilation head of claim 41, wherein the arterial and venous fluid ports are disposed in a hexagonal packing structure, the arterial ports outnumber the venous ports by 2-to-1, or a sum of cross-sectional areas of the venous ports exceeds that of the arterial ports by 3-to-2.

45. In a nondestructive means of ectopic pregnancy management, a ventilation catheter system, comprising: arterial and venous catheter lines in fluidic communication with arterial and venous fluid ports configured to urge a ventilating liquid to circulate within an intervillous space via a fluidic ventilator, wherein the arterial and venous fluid ports are configured to be disposed within the intervillous space, and wherein opposing arterial and venous fluid ports are separated by a predetermined spacing distance, whereby a fluid path length of the ventilating liquid traveling between the opposing fluid ports within the intervillous space is determined by the spacing distance between the opposing fluid ports.

46. The ventilation catheter system of claim 45, wherein the opposing fluid ports are disposed in a ventilating segment of at least one bidirectional catheter or the spacing distance between the opposing fluid ports is one centimeter or less.

47. The ventilation catheter system of claim 46, wherein the ventilating segment of the at least one bidirectional catheter is configured to being placed within the intervillous space vertically or horizontally relative to a chorionic plate or coiled around a villous tree.

48. In a nondestructive means of ectopic pregnancy management, a ventilation catheter system, comprising: an arterial catheter and a venous catheter configured to being inserted into an intervillous space parallel to each other and perpendicular to a chorionic plate, and
a fluidic ventilator,
wherein a ventilating liquid is urged from the fluidic ventilator via an arterial line through the arterial catheter, the liquid emerging from a series of arterial fluid ports disposed along a length of the arterial catheter within the intervillous space, wherein the liquid travels to adjacent venous fluid ports disposed along a length of the venous catheter within the intervillous space and is returned to the ventilator via a venous line, and wherein a fluid path length of the ventilating liquid flowing between the adjacent arterial and venous fluid ports is preset according to a lateral distance of spacing between the catheters within the intervillous space.

49. The ventilation catheter system of claim 48, wherein the lateral distance of spacing between the catheters within the intervillous space is one centimeter or less.

50. In a nondestructive means of ectopic pregnancy management, a ventilation catheter, comprising: a flexible catheter body, a ventilating segment disposed on the catheter body, and an alluvial ventilator, the catheter body having at least one lumen for fluid flow disposed therein and being adapted to placement within an intervillous space to circulate a ventilating liquid, and further having a sealed distal end, a proximal end adapted to fluidic communication with the alluvial ventilator to urge the ventilating liquid, the ventilating segment being defined by having a series of fluid ports disposed along a length of the catheter body to admit fluidic communication between the intervillous space and the at least one lumen, wherein the ventilating segment is sized and configured for ventilating a predetermined area within the intervillous space.

51. The ventilation catheter of claim 50, wherein a distal portion of the catheter body is attached to an absorbable transfer capsule.

52. In a nondestructive means of ectopic pregnancy management, a bidirectional ventilation catheter, comprising: a flexible catheter body, having at least two lumens for fluid flow disposed therein and being adapted to placement within an intervillous space to circulate a ventilating liquid, at least one of the lumens serving an arterial flow direction and at least one of the lumens serving a venous flow direction, and further having a sealed distal end, a proximal end adapted to fluidic communication with an alluvial ventilator to urge the ventilating liquid, and a ventilating segment, the segment being defined by having a series of arterial and venous fluid ports disposed along a length of the catheter body to admit fluidic communication between the intervillous space and the at least two lumens serving respective flow directions, wherein the ventilating segment is sized and configured for ventilating a predetermined area within the intervillous space.

53. The bidirectional ventilation catheter of claim 52, wherein the at least two lumens include a central lumen and two side lumens and the central lumen serves the venous flow direction and the two side lumens serve the arterial flow direction or the central lumen serves the arterial flow direction and the two side lumens serve the venous flow direction.

54. In a nondestructive means of ectopic pregnancy management, a chorionic spacer, comprising: a structural member sized and configured to maintain a predetermined minimum distance of spacing in an intervillous space between a chorionic plate and a wall external to an alluvial infant and to maintain fluidic patency within the intervillous space against compression forces exerted between the wall and the chorionic plate.

55. The chorionic spacer of claim 54, wherein the structural member consists of a ring adapted to slidably receive a ventilation catheter therethrough.

56. In a nondestructive means of ectopic pregnancy management, a microfluidic delivery forceps, comprising: a delivery forceps having blades with microfluidic ports for liquid outlet and inlet disposed therein in communication with a network of microfluidic channels, whereby the forceps is configured to fluidically ventilate an alluvial infant contained therein via a ventilation catheter attached to the forceps.

57. An alluvial ventilator, comprising: a ventilation catheter or ventilation head, a chorionic spacer configured to maintain fluidic patency within an intervillous space in proximity to the ventilation catheter or ventilation head, a reservoir for a ventilating liquid, and a circulator configured to circulate the ventilating liquid at a controlled temperature and rate of flow within the intervillous space in a manner of fluidic ventilation via the ventilation catheter or ventilation head, the circulator, further including a pump to urge the ventilating liquid and a regulator to control at least a rate of flow.

58. The alluvial ventilator of claim 57, wherein the ventilation catheter comprises a flexible tubing having at least one fluid port disposed therein or attached thereto to deliver or withdraw a quantity of the ventilating liquid in fluidic communication with the circulator.

59. An absorbable transfer capsule for an implantable baby having an intact gestational sac, comprising: an enclosure for the baby made of at least one absorbable material, the enclosure being sized to the baby and configured for placement of the baby within the enclosure, for entry of the enclosure into a uterine cavity, and for protection of the baby within the enclosure, the at least one absorbable material being disposed to at least partial degradation within a predetermined period of time after introduction into the uterine cavity, the enclosure being configured to degrade after introduction into the uterine cavity to release the baby from the enclosure for implantation or reimplantation and forming a structure selected from the group consisting of:

a soft shell capsule having at least one slit disposed in enclosure walls having an elasticity and flexibility, the at least one slit being sized to admit entry of the baby into the enclosure, whereby the walls fold back about the at least one slit when placing the baby inside the enclosure and then close back over the baby once the walls are released;

a straw capsule having capped ends to hold the baby and a ventilating liquid inside the enclosure; and, a cartridge capsule formed of a series of absorbable layers using layer-based microfabrication techniques and having a microcradle disposed in the layers including a cover layer to hold the baby and a ventilating liquid inside the enclosure.

60. The capsule of claim 59, wherein the soft shell capsule further includes a pabulum for the baby disposed within the enclosure in an intervillous space and the straw capsule further includes a filter to limit transit of the baby relative to the ventilating liquid.

61. The capsule of claim 60, wherein the straw capsule and cartridge capsule further include a hydrogel micropump or an osmotic micropump to urge the ventilating liquid within the enclosure.

62. The capsule of claim 59, wherein enclosure walls or degrading enclosure walls release at least one beneficial substance for the baby or a mother of the baby.

63. An absorbable intrauterine pregnancy capsule, comprising: an enclosure for a human egg or hatchling made of at least one absorbable material and containing a micropump and a filter, the filter being configured to limit transit of the egg or hatchling within the enclosure relative to a flow of a ventilating liquid within the enclosure, the micropump being configured to urge the ventilating liquid to flow over the egg or hatchling, and the at least one absorbable material being disposed to at least partial degradation within a predetermined period of time after introduction into a uterine cavity, the enclosure being configured to degrade after introduction into the uterine cavity to release the egg or hatchling from the enclosure for implantation.

64. The capsule of claim 63, wherein the micropump is a hydrogel micropump or an osmotic micropump.

65. The capsule of claim 64, wherein said enclosure comprises enclosure walls with holes sized to admit entry of male gametes to fertilize the egg within the enclosure.

66. The capsule of claim 64, wherein said enclosure has enclosure walls containing hyaluronan.

67. An alluvial incubator, comprising: an enclosure, a cradle, and a fluidic ventilator, the enclosure being configured to hold and support a baby with the cradle within the enclosure and which enclosure is filled with a ventilating liquid circulated within an intervillous space by the fluidic ventilator.

* * * * *